US009920310B2

(12) United States Patent
Anderson et al.

(10) Patent No.: US 9,920,310 B2
(45) Date of Patent: Mar. 20, 2018

(54) CATIONIC NEUROTOXINS

(71) Applicant: IPSEN BIOINNOVATION LIMITED, Abingdon, Oxfordshire (GB)

(72) Inventors: Dina Brady Anderson, Abingdon (GB); Gavin Stephen Hackett, Abingdon (GB); Sai Man Liu, Abingdon (GB)

(73) Assignee: Ipsen BioInnovation, Limited, Abingdon, Oxfordshire (GB)

( * ) Notice: Subject to any disclaimer, the term of this patent is extended or adjusted under 35 U.S.C. 154(b) by 5 days.

(21) Appl. No.: 14/903,458

(22) PCT Filed: Jul. 9, 2014

(86) PCT No.: PCT/GB2014/052097
§ 371 (c)(1),
(2) Date: Jan. 7, 2016

(87) PCT Pub. No.: WO2015/004461
PCT Pub. Date: Jan. 15, 2015

(65) Prior Publication Data
US 2016/0369256 A1 Dec. 22, 2016

(30) Foreign Application Priority Data

Jul. 9, 2013 (GB) .................................. 1312317.9

(51) Int. Cl.
*C07K 14/33* (2006.01)
*C12N 9/52* (2006.01)
*A61K 38/48* (2006.01)

(52) U.S. Cl.
CPC ............ *C12N 9/52* (2013.01); *A61K 38/4886* (2013.01); *A61K 38/4893* (2013.01); *C07K 14/33* (2013.01); *C12Y 304/24068* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 5,437,291 A | 8/1995 | Pasricha et al. |
| 5,670,484 A | 9/1997 | Binder |
| 5,714,469 A | 2/1998 | DeMarsh |
| 5,989,545 A | 11/1999 | Foster et al. |
| 6,063,768 A | 5/2000 | First |
| 6,113,915 A | 9/2000 | Aoki et al. |
| 6,139,845 A | 10/2000 | Donovan |
| 6,143,306 A | 11/2000 | Donovan |
| 6,261,572 B1 | 7/2001 | Donovan |
| 6,265,379 B1 | 7/2001 | Donovan |
| 6,299,893 B1 | 10/2001 | Schwartz et al. |
| 6,306,403 B1 | 10/2001 | Donovan |
| 6,319,505 B1 | 11/2001 | Aoki et al. |
| 6,337,075 B1 | 1/2002 | Donovan |
| 6,358,917 B1 | 3/2002 | Carruthers et al. |
| 6,358,926 B2 | 3/2002 | Donovan |
| 6,368,605 B1 | 4/2002 | Donovan |
| 6,395,513 B1 | 5/2002 | Foster et al. |
| 6,416,765 B1 | 7/2002 | Donovan |
| 6,423,319 B1 | 7/2002 | Brooks et al. |
| 6,458,365 B1 | 10/2002 | Aoki et al. |
| 6,461,617 B1 | 10/2002 | Shone et al. |
| 6,464,986 B1 | 10/2002 | Aoki et al. |
| 6,565,870 B1 | 5/2003 | Donovan |
| 6,620,415 B2 | 9/2003 | Donovan |
| 6,623,742 B2 | 9/2003 | Voet |
| 6,632,440 B1 | 10/2003 | Quinn et al. |
| 6,641,820 B1 | 11/2003 | Donovan |
| 6,683,049 B1 | 1/2004 | Aoki et al. |
| 6,740,321 B1 | 5/2004 | Donovan |
| 6,767,544 B2 | 7/2004 | Brooks et al. |
| 6,776,992 B2 | 8/2004 | Aoki et al. |
| 6,827,931 B1 | 12/2004 | Donovan |
| 6,838,434 B2 | 1/2005 | Voet |
| 6,869,610 B2 | 3/2005 | Aoki et al. |
| 6,872,397 B2 | 3/2005 | Aoki et al. |
| 6,962,703 B2 | 11/2005 | Foster et al. |
| 7,052,702 B1 | 5/2006 | Duggan et al. |
| 7,132,259 B1 | 11/2006 | Dolly et al. |
| 7,192,596 B2 | 3/2007 | Shone et al. |

(Continued)

FOREIGN PATENT DOCUMENTS

| | | |
|---|---|---|
| EP | 0 689 459 B1 | 12/2002 |
| WO | 94/21300 A2 | 9/1994 |

(Continued)

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Aoki, K. R., "A Comparison of the Safety Margins of Botulinum Neurotoxin Serotypes A, B, and F in Mice", Toxicon, No. 39, pp. 1815-1820, (2001).
Robertson, et al., "A General and Efficient Route for Chemical Aminoacylation of Transfer RNAs", J. Am. Chem. Soc., vol. 113, pp. 2722-2729, (1991).
Ellman, et al., "Biosynthetic Method for Introducing Unnatural Amino Acids Site-Specifically Into Proteins", Methods of Enzymology, vol. 202, pp. 301-336, (1991).
Chung, et al., "Probing the Structure and Mechanism of Ras Protein with an Expanded Genetic Code", Science, vol. 259, pp. 806-809, (1993).

(Continued)

*Primary Examiner* — Brian Gangle
(74) *Attorney, Agent, or Firm* — Hunton & Williams LLP

(57) ABSTRACT

The present invention provides an engineered clostridial toxin comprising at least one amino acid modification, wherein said at least one amino acid modification increases the isoelectric point (pI) of the engineered clostridial toxin to a value that is at least 0.2 pI units higher than the pI of an otherwise identical clostridial toxin lacking said at least one amino acid modification. Also provided are corresponding uses of the engineered clostridial toxin in therapy.

19 Claims, 4 Drawing Sheets

(56) References Cited

U.S. PATENT DOCUMENTS

| | | | |
|---|---|---|---|
| 2002/0010138 | A1 | 1/2002 | Aoki et al. |
| 2003/0211121 | A1 | 11/2003 | Donovan |
| 2004/0013692 | A1 | 1/2004 | Aoki et al. |
| 2004/0037852 | A1 | 2/2004 | Aoki et al. |
| 2004/0062776 | A1 | 4/2004 | Voet |
| 2004/0086531 | A1 | 5/2004 | Barron |
| 2004/0115139 | A1 | 6/2004 | Katz et al. |
| 2004/0126396 | A1 | 7/2004 | Aoki et al. |
| 2004/0151740 | A1 | 8/2004 | Aoki et al. |
| 2004/0175399 | A1 | 9/2004 | Schiffman |
| 2004/0180061 | A1 | 9/2004 | Donovan |
| 2004/0234532 | A1 | 11/2004 | First |
| 2005/0031648 | A1 | 2/2005 | Brin et al. |
| 2007/0166332 | A1 | 7/2007 | Steward et al. |
| 2011/0318385 | A1 | 12/2011 | Jackson et al. |

FOREIGN PATENT DOCUMENTS

| | | | |
|---|---|---|---|
| WO | 01/21213 | A2 | 3/2001 |
| WO | 02/08268 | A2 | 1/2002 |
| WO | 2006/027207 | A1 | 3/2006 |
| WO | 2006/114308 | A2 | 11/2006 |
| WO | 2010/120766 | A1 | 10/2010 |

OTHER PUBLICATIONS

Chung, et al., "Probing the Role of Loop 2 in Ras Function with Unnatural Amino Acids", Proc. Natl. Acad. Sci., vol. 90, pp. 10145-10149, (Nov. 1993).

Turcatti, et al., "Probing the Structure and Function of the Tachykinin Neurokinin-2 Receptor Through Biosynthetic Incorporation of Fluorescent Amino Acids at Specific Sites", J. Biol. Chem., vol. 271, No. 33, pp. 19991-19998, (1996).

Koide, et al., "Receptor-Binding Affinities of Human Epidermal Growth Factor Variants Having Unnatural Amino Acid Residues in Position 23", Biochemistry, vol. 33, No. 23, pp. 7470-7476, (1994).

Byrne, M. et al., "Purification, Potency, and Efficacy of the Botulinum Neurotoxin Type A Binding Domain from Pichia pastoris as a Recombinant Vaccine Candidate", Infection and Immunity, American Society for Microbiology, US, vol. 66, No. 10, Oct. 1, 1998, pp. 4817-4822.

International Search Report issued in PCT/GB2014/052097 (dated Oct. 7, 2014).

International Preliminary Report on Patententability issued in PCT/GB2014/052097 (dated Aug. 24, 2015).

* cited by examiner

| SXN/Batch | $t_{50}$ (mean min ± sem) |
|---|---|
| nBoNT/A1 | 52 ± 3 |
| Cat5v2(K1064H/N886K) | 49 ± 3 |
| Cat5v2(K1064H/N954K) | 48 ± 3 |
| Cat5v2(K1064H/N1025K) | 47 ± 3 |

CATIONIC NEUROTOXINS

The instant application contains a Sequence Listing which has been submitted electronically in ASCII format and is hereby incorporated by reference in its entirety. Said ASCII copy, created on Sep. 12, 2017, is named 58767_000934_SL.txt and is 84,004 bytes in size.

The present invention relates to engineered clostridial toxins comprising at least one amino acid modification, and the use of such engineered clostridial toxins in medicine and therapy.

Bacteria in the genus *Clostridia* produce highly potent and specific protein toxins, which can poison neurons and other cells to which they are delivered. Examples of such clostridial toxins include the neurotoxins produced by *C. tetani* (TeNT) and by *C. botulinum* (BoNT) serotypes A-G, as well as those produced by *C. baratii* and *C. butyricum*.

Among the clostridial toxins are some of the most potent toxins known. By way of example, botulinum neurotoxins have median lethal dose ($LD_{50}$) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

In nature, clostridial toxins are synthesised as a single-chain polypeptide that is modified post-translationally by a proteolytic cleavage event to form two polypeptide chains joined together by a disulphide bond. Cleavage occurs at a specific cleavage site, often referred to as the activation site, that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of clostridial toxins are non-cytotoxic proteases that cleave SNARE proteins.

In view of the ubiquitous nature of SNARE proteins, clostridial toxins such as botulinum toxin have been successfully employed in a wide range of therapies.

By way of example, we refer to William J. Lipham, Cosmetic and Clinical Applications of Botulinum Toxin (Slack, Inc., 2004), which describes the use of clostridial toxins, such as botulinum neurotoxins (BoNTs), BoNT/A, BoNT/B, BoNT/C$_1$, BoNT/D, BoNT/E, BoNT/F and BoNT/G, and tetanus neurotoxin (TeNT), to inhibit neuronal transmission in a wide variety of therapeutic and cosmetic applications—as an example, BOTOX™ is currently approved as a therapeutic for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder. In addition, clostridial toxin therapies are described for treating neuromuscular disorders (see U.S. Pat. No. 6,872,397); for treating uterine disorders (see US 2004/0175399); for treating ulcers and gastroesophageal reflux disease (see US 2004/0086531); for treating dystonia (see U.S. Pat. No. 6,319,505); for treating eye disorders (see US 2004/0234532); for treating blepharospasm (see US 2004/0151740); for treating strabismus (see US 2004/0126396); for treating pain (see U.S. Pat. No. 6,869,610, U.S. Pat. No. 6,641,820, U.S. Pat. No. 6,464,986, and U.S. Pat. No. 6,113,915); for treating fibromyalgia (see U.S. Pat. No. 6,623,742, US 2004/0062776); for treating lower back pain (see US 2004/0037852); for treating muscle injuries (see U.S. Pat. No. 6,423,319); for treating sinus headache (see U.S. Pat. No. 6,838,434); for treating tension headache (see U.S. Pat. No. 6,776,992); for treating headache (see U.S. Pat. No. 6,458,365); for reduction of migraine headache pain (see U.S. Pat. No. 5,714,469); for treating cardiovascular diseases (see U.S. Pat. No. 6,767,544); for treating neurological disorders such as Parkinson's disease (see U.S. Pat. No. 6,620,415, U.S. Pat. No. 6,306,403); for treating neuropsychiatric disorders (see US 2004/0180061, US 2003/0211121); for treating endocrine disorders (see U.S. Pat. No. 6,827,931); for treating thyroid disorders (see U.S. Pat. No. 6,740,321); for treating cholinergic influenced sweat gland disorders (see U.S. Pat. No. 6,683,049); for treating diabetes (see U.S. Pat. No. 6,337,075, U.S. Pat. No. 6,416,765); for treating a pancreatic disorder (see U.S. Pat. No. 6,261,572, U.S. Pat. No. 6,143,306); for treating cancers such as bone tumors (see U.S. Pat. No. 6,565,870, U.S. Pat. No. 6,368,605, U.S. Pat. No. 6,139,845, US 2005/0031648); for treating otic disorders (see U.S. Pat. No. 6,358,926, U.S. Pat. No. 6,265,379); for treating autonomic disorders such as gastrointestinal muscle disorders and other smooth muscle dysfunction (see U.S. Pat. No. 5,437,291); for treatment of skin lesions associated with cutaneous cell-proliferative disorders (see U.S. Pat. No. 5,670,484); for management of neurogenic inflammatory disorders (see U.S. Pat. No. 6,063,768); for reducing hair loss and stimulating hair growth (see U.S. Pat. No. 6,299,893); for treating downturned mouth (see U.S. Pat. No. 6,358,917); for reducing appetite (see US 2004/40253274); for dental therapies and procedures (see US 2004/0115139); for treating neuromuscular disorders and conditions (see US 2002/0010138); for treating various disorders and conditions and associated pain (see US 2004/0013692); for treating conditions resulting from mucus hypersecretion such as asthma and COPD (see WO 00/10598); and for treating non-neuronal conditions such as inflammation, endocrine conditions, exocrine conditions, immunological conditions, cardiovascular conditions, bone conditions (see WO 01/21213). All of the above publications are hereby incorporated by reference in their entirety.

The use of non-cytotoxic proteases such as clostridial toxins (e.g. BoNTs and TeNT) in therapeutic and cosmetic treatments of humans and other mammals is anticipated to expand to an ever-widening range of diseases and ailments that can benefit from the properties of these toxins.

To avoid systemic neurological effects, many clostridial toxin therapies utilise direct administration of the clostridial toxin therapeutic to a given target site (such as a target tissue). A problem when administering clostridial toxin-based therapeutics in this fashion is the spread of toxin away from the administration site and into surrounding tissue or systemic circulation. The diffusion of toxin away from the target tissue is believed to be responsible for undesirable side effects that in extreme cases may be life threatening. This can be a particular concern when using clostridial toxin therapeutics (such as BoNT therapeutics) at high doses, concentrations and injection volumes. Adverse effects associated with this problem that have been reported for commercial BoNT/A therapeutics include asthenia, generalised muscle weakness, diplopia, ptosis, dysphagia, dysphonia, dysarthria, urinary incontinence, and breathing difficulties. Swallowing and breathing difficulties can be life threatening and there have been reported deaths related to the spread of toxin effects.

There is therefore a need in the art for clostridial toxins which have properties of increased tissue retention at the site of administration, and which accordingly exhibit a reduction in diffusion away from the administration site, as compared to known clostridial toxins.

The present invention solves the above problem by providing engineered clostridial toxins, as specified in the claims.

In one aspect, the invention provides an engineered clostridial toxin comprising at least one amino acid modification, wherein said at least one amino acid modification increases the isoelectric point (pI) of the engineered clostridial toxin to a value that is at least 0.2 (for example, at least 0.2, 0.3, 0.4, 0.5, 0.6, 0.7, 0.8, 0.9 or 1) pI units higher than the pI of an otherwise identical clostridial toxin lacking said at least one amino acid modification. In one embodiment, said at least one amino acid modification increases the pI of the engineered clostridial toxin to a value that is at least 0.4 pI units higher than the pI of an otherwise identical clostridial toxin lacking said at least one amino acid modification. In one embodiment, said at least one amino acid modification increases the pI of the engineered clostridial toxin to a value that is at least 0.5 pI units higher than the pI of an otherwise identical clostridial toxin lacking said at least one amino acid modification. In one embodiment, said at least one amino acid modification increases the pI of the engineered clostridial toxin to a value that is at least 0.6 pI units higher than the pI of an otherwise identical clostridial toxin lacking said at least one amino acid modification. In one embodiment, said at least one amino acid modification increases the pI of the engineered clostridial toxin to a value that is at least 0.8 pI units higher than the pI of an otherwise identical clostridial toxin lacking said at least one amino acid modification. In one embodiment, said at least one amino acid modification increases the pI of the engineered clostridial toxin to a value that is at least 1 pI unit higher than the pI of an otherwise identical clostridial toxin lacking said at least one amino acid modification.

In one aspect, the invention provides an engineered clostridial toxin comprising at least one amino acid modification, wherein said at least one amino acid modification increases the isoelectric point (pI) of the engineered clostridial toxin to a value that is at least one pI unit higher than the pI of an otherwise identical clostridial toxin lacking said at least one amino acid modification.

In certain embodiments, the engineered clostridial toxin comprises at least 2, 3, 4, 5, 10, 15, 20, 25, 30, 35, 40, 45, 50, 55, 60, 65, 70, 75 or 80 amino acid modifications.

In certain embodiments, said at least one amino acid modification increases the pI of the engineered clostridial toxin to a value that is at least 2, 3, 4 or 5 pI units higher than the pI of an otherwise identical clostridial toxin lacking said at least one amino acid modification.

The present inventors have found that by increasing the pI of a clostridial toxin, for example, by at least 0.2 pI units, or 0.5 pI units, or one pI unit (through the introduction into the clostridial toxin protein of at least one amino acid modification), the resultant engineered clostridial toxin advantageously demonstrates properties of increased tissue retention and reduced diffusion away from sites of administration, while retaining abilities of target cell binding, translocation, and cleavage of target SNARE protein(s). Thus, the spread of clostridial toxin from the site of administration is significantly reduced, as compared to an otherwise identical clostridial toxin lacking said at least one amino acid modification.

The engineered clostridial toxins of the invention are suitable for use in any of the therapies described above, and advantageously may demonstrate a reduction in, or absence of, side effects compared to the use of known clostridial toxin therapeutics.

The increased tissue retention properties of the engineered clostridial toxins of the invention also provide increased potency and/or duration of action, and can allow for reduced dosages to be used compared to known clostridial toxin therapeutics (or increased dosages without any additional adverse effects), thus providing further advantages.

As discussed below in more detail, the increase in pI provided by the at least one amino acid modification means that an engineered clostridial toxin of the invention has, at a given pH, a net charge that is more positive than the net charge on an otherwise identical clostridial toxin lacking said at least one amino acid modification. Without wishing to be bound by any one theory, the present inventors believe that this increased positive charge allows the engineered clostridial toxins of the present invention to display longer tissue retention times at the site of administration due to favourable electrostatic interactions between the engineered clostridial toxin and anionic extracellular components (such as cell membranes and heparin sulphate proteoglycans) at the site of administration. These improved electrostatic interactions serve to reduce the diffusion of the engineered clostridial toxin away from the site of administration, thus improving tissue retention.

By way of example, the improved tissue retention properties of an engineered clostridial toxin of the invention may allow for (i) higher doses into individual muscles, such as the sternocleidomastoid, without spreading into nearby muscles in the neck to cause difficult swallowing, and (ii) higher total doses (to all muscles) in a single treatment, without spreading into the circulation and causing systemic effects such as difficult breathing. Advantages to patients may include more effective treatment of large muscles such as the sternocleidomastoid muscle, increased opportunity to inject several different muscles during each treatment, and possible longer duration of effective treatment (longer before re-treatment is necessary) because of higher dosing.

In one embodiment, an engineered clostridial toxin of the invention has, in use, a positive net charge (for example, when the engineered clostridial toxin, in use, is located at a desired administration site in a tissue).

The isoelectric point (pI) is a specific property of a given protein. As is well known in the art, proteins are made from a specific sequence of amino acids (also referred to when in a protein as amino acid residues). Each amino acid of the standard set of twenty has a different side chain (or R group), meaning that each amino acid residue in a protein displays different chemical properties such as charge and hydrophobicity.

These properties may be influenced by the surrounding chemical environment, such as the temperature and pH. The overall chemical characteristics of a protein will depend on the sum of these various factors.

Certain amino acid residues (detailed below) possess ionisable side chains that may display an electric charge depending on the surrounding pH. Whether such a side chain is charged or not at a given pH depends on the pKa of the relevant ionisable moiety, wherein pKa is the negative logarithm of the acid dissociation constant (Ka) for a specified proton from a conjugate base.

For example, acidic residues such as aspartic acid and glutamic acid have side chain carboxylic acid groups with pKa values of approximately 4.1 (precise pKa values may depend on temperature, ionic strength and the microenvironment of the ionisable group). Thus, these side chains exhibit a negative charge at a pH of 7.4 (often referred to as "physiological pH"). At low pH values, these side chains will become protonated and lose their charge.

Conversely, basic residues such as lysine and arginine have nitrogen-containing side chain groups with pKa values of approximately 10-12. These side chains therefore exhibit a positive charge at a pH of 7.4. These side chains will become de-protonated and lose their charge at high pH values.

The overall (net) charge of a protein molecule therefore depends on the number of acidic and basic residues present in the protein (and their degree of surface exposure) and on the surrounding pH. Changing the surrounding pH changes the overall charge on the protein. Accordingly, for every protein there is a given pH at which the number of positive and negative charges is equal and the protein displays no overall net charge. This point is known as the isoelectric point (pI). The isoelectric point is a standard concept in protein biochemistry with which the skilled person would be familiar.

The isoelectric point (pI) is therefore defined as the pH value at which a protein displays a net charge of zero. An increase in pI means that a higher pH value is required for the protein to display a net charge of zero. Thus, an increase in pI represents an increase in the net positive charge of a protein at a given pH. Conversely, a decrease in pI means that a lower pH value is required for the protein to display a net charge of zero. Thus, a decrease in pI represents a decrease in the net positive charge of a protein at a given pH.

Methods of determining the pI of a protein are known in the art and would be familiar to a skilled person. By way of example, the pI of a protein can be calculated from the average pKa values of each amino acid present in the protein. Alternatively, the pI of a protein can be determined experimentally using the technique of isoelectric focusing. This technique uses electrophoresis to separate proteins according to their pI. Isoelectric focusing is typically performed using a gel that has an immobilised pH gradient. When an electric field is applied, the protein migrates through the pH gradient until it reaches the pH at which it has zero net charge, this point being the pI of the protein.

The pI of a protein may be increased or decreased by altering the number of basic and/or acidic groups displayed on its surface. This can be achieved by modifying one or more amino acids of the protein. For example, an increase in pI may be provided by reducing the number of acidic residues, or by increasing the number of basic residues. Such amino acid modifications are discussed in more detail below.

Native (unmodified) clostridial toxins have a pI of approximately 5-6. Thus, at a pH of 7.4, native botulinum toxins possess a negative net charge. By way of example, the pI of BoNT/A is 6.4, and a BoNT/A molecule has a net charge at pH 7.4 of −8. These pI values are calculated as described above.

TABLE 1

| CLOSTRIDIAL TOXIN | pI |
|---|---|
| BoNT/A | 6.4 |
| BoNT/B | 5.3 |
| BoNT/C$_1$ | 5.5 |
| BoNT/D | 5.5 |
| BoNT/E | 6.0 |
| BoNT/F | 5.6 |
| BoNT/G | 5.2 |
| TeNT | 5.8 |

As described above, in one embodiment, an engineered clostridial toxin of the present invention comprises at least one amino acid modification, wherein said at least one amino acid modification increases the isoelectric point (pI) of the engineered clostridial toxin to a value that is at least 0.2 pI units higher than the pI of an otherwise identical clostridial toxin lacking said at least one amino acid modification.

Thus, in the context of the present invention, an increase in pI of 0.2 units in the context of an engineered BoNT/A clostridial toxin would be an increase in pI from 6.4 to 6.6.

As described above, in one embodiment, an engineered clostridial toxin of the present invention comprises at least one amino acid modification, wherein said at least one amino acid modification increases the isoelectric point (pI) of the engineered clostridial toxin to a value that is at least one pI unit higher than the pI of an otherwise identical clostridial toxin lacking said at least one amino acid modification.

Thus, in the context of the present invention, an increase in pI of 1 unit in the context of an engineered BoNT/A clostridial toxin would be an increase in pI from 6.4 to 7.4.

In one embodiment, said at least one amino acid modification increases the isoelectric point (pI) of the engineered clostridial toxin to a value that is at least two pI units higher than the pI of an otherwise identical clostridial toxin lacking said at least one amino acid modification.

In one embodiment, said at least one amino acid modification increases the isoelectric point (pI) of the engineered clostridial toxin to a value that is between 2 and 5 pI units higher than the pI of an otherwise identical clostridial toxin lacking said at least one amino acid modification.

In one embodiment, the engineered clostridial toxin has a pI of at least 6 (for example, at least 6, at least 7, at least 8, or at least 9).

In one embodiment, the engineered clostridial toxin has a pI of at least 7.

In one embodiment, the engineered clostridial toxin has a pI of between 6 and 10 (for example a pI of between 7 and 9, or a pI of between 8 and 9).

As discussed above, the engineered clostridial toxins of the present invention have increased tissue retention properties that also provide increased potency and/or duration of action, and can allow for reduced dosages to be used compared to known clostridial toxin therapeutics (or increased dosages without any additional effects). One way in which these advantageous properties (which represent an increase in the therapeutic index) may be defined is in terms of the Safety Ratio of the engineered clostridial toxin. In this regard, undesired effects of a clostridial toxin (caused by diffusion of the toxin away from the site of administration) can be assessed experimentally by measuring percentage bodyweight loss in a relevant animal model (e.g. a mouse, where loss of bodyweight is detected within seven days of administration). Conversely, desired on-target effects of a clostridial toxin can be assessed experimentally by Digital Abduction Score (DAS) assay, a measurement of muscle paralysis. The DAS assay may be performed by injection of 20 μl of clostridial toxin, formulated in Gelatin Phosphate Buffer, into the mouse gastrocnemius/soleus complex, followed by assessment of Digital Abduction Score using the method of Aoki (Aoki K R, Toxicon 39: 1815-1820; 2001). In the DAS assay, mice are suspended briefly by the tail in order to elicit a characteristic startle response in which the mouse extends its hind limbs and abducts its hind digits. Following clostridial toxin injection, the varying degrees of digit abduction are scored on a five-point scale (0=normal to 4=maximal reduction in digit abduction and leg extension).

The Safety Ratio of a clostridial toxin may then be expressed as the ratio between the amount of toxin required for a 10% drop in a bodyweight (measured at peak effect within the first seven days after dosing in a mouse) and the amount of toxin required for a DAS score of 2. High Safety Ratio scores are therefore desired, and indicate a toxin that is able to effectively paralyse a target muscle with little undesired off-target effects. An engineered toxin of the present invention has a Safety Ratio that is higher than the Safety Ratio of an equivalent unmodified (native) botulinum toxin.

Thus, in one embodiment, an engineered clostridial toxin of the present invention has a Safety Ratio of at least 8 (for example, at least 8, 9, 10, 15, 20, 25, 30, 35, 40, 45 or 50), wherein Safety Ratio is calculated as: dose of toxin required for −10% bodyweight change (pg/mouse) divided by DAS $ED_{50}$ (pg/mouse) [$ED_{50}$=dose required to produce a DAS score of 2].

In one embodiment, an engineered clostridial toxin of the present invention has a Safety Ratio of at least 10. In one embodiment, an engineered clostridial toxin of the present invention has a Safety Ratio of at least 15.

An engineered clostridial toxin of the present invention comprises at least one amino acid modification. Said at least one amino acid modification increases the pI of the clostridial toxin, as discussed above. In the context of the present invention, an amino acid modification is a modification of the amino acid sequence of a clostridial toxin. Such a modification may be effected by replacing one amino acid in the sequence with another (i.e. a substitution), by inserting a new amino acid into the sequence, or by deleting an amino acid of the sequence. Amino acids incorporated into an amino acid sequence in a protein are also referred to as amino acid residues.

The 20 standard amino acids found in proteins are as follows:

TABLE 2

| AMINO ACID | | | SIDE CHAIN |
|---|---|---|---|
| Aspartic acid | Asp | D | Charged (acidic) |
| Glutamic acid | Glu | E | Charged (acidic) |
| Arginine | Arg | R | Charged (basic) |
| Lysine | Lys | K | Charged (basic) |
| Histidine | His | H | Uncharged (polar) |
| Asparagine | Asn | N | Uncharged (polar) |
| Glutamine | Gln | Q | Uncharged (polar) |
| Serine | Ser | S | Uncharged (polar) |
| Threonine | Thr | T | Uncharged (polar) |
| Tyrosine | Tyr | Y | Uncharged (polar) |
| Methionine | Met | M | Uncharged (polar) |
| Tryptophan | Trp | W | Uncharged (polar) |
| Cysteine | Cys | C | Uncharged (polar) |
| Alanine | Ala | A | Uncharged (hydrophobic) |
| Glycine | Gly | G | Uncharged (hydrophobic) |
| Valine | Val | V | Uncharged (hydrophobic) |
| Leucine | Leu | L | Uncharged (hydrophobic) |
| Isoleucine | Ile | I | Uncharged (hydrophobic) |
| Proline | Pro | P | Uncharged (hydrophobic) |
| Phenylalanine | Phe | F | Uncharged (hydrophobic) |

The following amino acids are considered charged amino acids: aspartic acid (negative), glutamic acid (negative), arginine (positive), and lysine (positive).

At a pH of 7.4, the side chains of aspartic acid (pKa 3.1) and glutamic acid (pKa 4.1) have a negative charge, while the side chains of arginine (pKa 12.5) and lysine (pKa 10.8) have a positive charge. Aspartic acid and glutamic acid are referred to as acidic amino acid residues. Arginine and lysine are referred to as basic amino acid residues.

The following amino acids are considered uncharged, polar (meaning they can participate in hydrogen bonding) amino acids: asparagine, glutamine, histidine, serine, threonine, tyrosine, cysteine, methionine, tryptophan.

The following amino acids are considered uncharged, hydrophobic amino acids: alanine, valine, leucine, isoleucine, phenylalanine, proline, and glycine.

An increase in the pI of a clostridial toxin can be effected by introducing into the clostridial toxin one or more amino acid modifications that increases the ratio of positive to negative charges in the clostridial toxin.

In one embodiment, the at least one amino acid modification is selected from: an amino acid substitution, an amino acid insertion, and an amino acid deletion.

In an amino acid substitution, an amino acid residue that forms part of the clostridial toxin amino acid sequence is replaced with a different amino acid residue. The replacement amino acid residue may be one of the 20 standard amino acids, as described above.

Alternatively, the replacement amino acid in an amino acid substitution may be a non-standard amino acid (an amino acid that is not part of the standard set of 20 described above). By way of example, the replacement amino acid may be a basic non-standard amino acid, e.g. L-Ornithine, L-2-amino-3-guanidinopropionic acid, or D-isomers of Lysine, Arginine and Ornithine). Methods for introducing non-standard amino acids into proteins are known in the art, and include recombinant protein synthesis using E. coli auxotrophic expression hosts.

In an amino acid insertion, an additional amino acid residue (one that is not normally present) is incorporated into the clostridial toxin amino acid sequence, thus increasing the total number of amino acid residues in said sequence.

In an amino acid deletion, an amino acid residue is removed from the clostridial toxin amino acid sequence, thus reducing the total number of amino acid residues in said sequence.

Methods for modifying proteins by substitution, insertion or deletion of amino acid residues are known in the art. By way of example, amino acid modifications may be introduced by modification of a DNA sequence encoding a clostridial toxin. This can be achieved using standard molecular cloning techniques, for example by site-directed mutagenesis where short strands of DNA (oligonucleotides) coding for the desired amino acid(s) are used to replace the original coding sequence using a polymerase enzyme, or by inserting/deleting parts of the gene with various enzymes (e.g., ligases and restriction endonucleases). Alternatively a modified gene sequence can be chemically synthesised.

In one embodiment, the at least one amino acid modification is selected from: substitution of an acidic amino acid residue with a basic amino acid residue; substitution of an acidic amino acid residue with an uncharged amino acid residue; substitution of an uncharged amino acid residue with a basic amino acid residue; insertion of a basic amino acid residue; and deletion of an acidic amino acid residue.

In a preferred embodiment, the at least one amino acid modification is a substitution, which advantageously maintains the same number of amino acid residues in the clostridial toxin. In one embodiment, the substitution is selected from: substitution of an acidic amino acid residue with a basic amino acid residue, substitution of an acidic amino acid residue with an uncharged amino acid residue, and substitution of an uncharged amino acid residue with a basic amino acid residue. In one embodiment, the basic amino acid residue is a lysine residue or an arginine residue. In one embodiment, the basic amino acid residue is a lysine residue. In one embodiment, the basic amino acid residue is an arginine residue. In one embodiment, wherein the substitution is a substitution of an acidic amino acid residue with an uncharged amino acid residue, the acidic amino acid residue is replaced with its corresponding uncharged amide amino acid residue (i.e. aspartic acid is replaced with asparagine, and glutamic acid is replaced with glutamine).

An engineered clostridial toxin of the invention may comprise more than one amino acid modification. Thus, in one embodiment, the engineered clostridial toxin (as described above) comprises between 1 and 80 amino acid modifications (for example, between 1 and 70, between 1 and 60, between 1 and 50, between 4 and 40, between 4 and 30, between 5 and 40, between 5 and 30, or between 10 and 25 amino acid modifications). In one embodiment, the engineered clostridial toxin (as described above) comprises between 4 and 40 amino acid modifications. In one embodiment, the engineered clostridial toxin comprises at least 2, at least 3, at least 4, at least 5, or at least 10 amino acid modifications. In one embodiment, the engineered clostridial toxin comprises at least 4 amino acid modifications (for example, at least 4 amino acid substitutions). Each of said amino acid modifications is an amino acid modification as described above. Thus, each of said amino acid modifications contributes to the increase in pI of the engineered clostridial toxin (as compared to the pI of an otherwise identical clostridial toxin lacking said amino acid modifications).

Any clostridial toxin amino acid (i.e. amino acid residue) can be modified as described above, as long as the outcome of said modification is an increase in the clostridial toxin pI (as described above). However, the present inventors have identified subsets of clostridial toxin amino acids that are particularly suitable targets for modification.

Preferred target amino acids may possess certain qualities. By way of example, a preferred target amino acid may be: (i) a surface exposed amino acid; (ii) located outside of a clostridial toxin protein secondary structure; (iii) located in a clostridial toxin protein region that is non-essential for protein function; (iv) an amino acid whose identity is not conserved between clostridial toxin types, subtypes, or serotypes; (iv) an amino acid whose modification does not create a predicted ubiquitination site; or (v) any combination of the foregoing.

As discussed above, clostridial toxins are formed from two polypeptide chains, the heavy chain (H-chain), which has a molecular mass of approximately 100 kDa, and the light chain (L-chain), which has a molecular mass of approximately 50 kDa. The H-chain comprises a C-terminal targeting component (receptor binding domain or $H_C$ domain) and an N-terminal translocation component ($H_N$ domain).

In one embodiment, the at least one amino acid modification (as described above) is located in the clostridial toxin receptor binding domain ($H_C$ domain).

Examples of light chain reference sequences include:
Botulinum type A neurotoxin: amino acid residues 1-448
Botulinum type B neurotoxin: amino acid residues 1-440
Botulinum type $C_1$ neurotoxin: amino acid residues 1-441
Botulinum type D neurotoxin: amino acid residues 1-445
Botulinum type E neurotoxin: amino acid residues 1-422
Botulinum type F neurotoxin: amino acid residues 1-439
Botulinum type G neurotoxin: amino acid residues 1-441
Tetanus neurotoxin: amino acid residues 1-457

The above-identified reference sequences should be considered a guide, as slight variations may occur according to sub-serotypes. By way of example, US 2007/0166332 (hereby incorporated by reference in its entirety) cites slightly different clostridial sequences:
Botulinum type A neurotoxin: amino acid residues M1-K448
Botulinum type B neurotoxin: amino acid residues M1-K441
Botulinum type $C_1$ neurotoxin: amino acid residues M1-K449
Botulinum type D neurotoxin: amino acid residues M1-R445
Botulinum type E neurotoxin: amino acid residues M1-R422
Botulinum type F neurotoxin: amino acid residues M1-K439
Botulinum type G neurotoxin: amino acid residues M1-K446
Tetanus neurotoxin: amino acid residues M1-A457

Examples of clostridial toxin $H_C$ domain reference sequences include:
BoNT/A—N872-L1296
BoNT/B—E859-E1291
BoNT/$C_1$—N867-E1291
BoNT/D—S863-E1276
BoNT/E—R846-K1252
BoNT/F—K865-E1274
BoNT/G—N864-E1297
TeNT—I880-D1315

The $H_C$ domain of a clostridial toxin (such as a BoNT) comprises two distinct structural features that are referred to as the $H_{CC}$ and $H_{CN}$ domains. Amino acid residues involved in receptor binding are believed to be primarily located in the $H_{CC}$ domain.

In one embodiment, wherein the at least one amino acid modification (as described above) is located in the clostridial toxin receptor binding domain ($H_C$ domain), said at least one amino acid modification is located in the clostridial toxin $H_{CN}$ domain (also referred to as a translocation facilitating domain). In one embodiment, wherein the at least one amino acid modification (as described above) is located in the clostridial toxin receptor binding domain ($H_C$ domain), said at least one amino acid modification is located in the clostridial toxin $H_{CC}$ domain.

Examples of clostridial toxin $H_{CN}$ domain reference sequences include:
Botulinum type A neurotoxin: amino acid residues 872-1110
Botulinum type B neurotoxin: amino acid residues 859-1097
Botulinum type $C_1$ neurotoxin: amino acid residues 867-1111
Botulinum type D neurotoxin: amino acid residues 863-1098
Botulinum type E neurotoxin: amino acid residues 846-1085
Botulinum type F neurotoxin: amino acid residues 865-1105
Botulinum type G neurotoxin: amino acid residues 864-1105
Tetanus neurotoxin: amino acid residues 880-1127

The above sequence positions may vary slightly according to serotype/sub-type, and further examples of suitable (reference) clostridial toxin $H_{CN}$ domains include:
Botulinum type A neurotoxin: amino acid residues 874-1110
Botulinum type B neurotoxin: amino acid residues 861-1097
Botulinum type $C_1$ neurotoxin: amino acid residues 869-1111
Botulinum type D neurotoxin: amino acid residues 865-1098
Botulinum type E neurotoxin: amino acid residues 848-1085
Botulinum type F neurotoxin: amino acid residues 867-1105
Botulinum type G neurotoxin: amino acid residues 866-1105
Tetanus neurotoxin: amino acid residues 882-1127

In one embodiment, the at least one amino acid modification (as described above) is a modification of a surface exposed amino acid residue. Surface exposed amino acid residues are those present on the exterior of a folded protein and so accessible to the surrounding solvent, in contrast to those amino acid residues that are located in the interior of a folded protein. The degree of surface exposure of an amino acid residue and thus its exposure to the surrounding solvent depends on its position within the folded protein, and also on the conformation adopted by the protein. Modification of an amino acid residue with a high degree of surface exposure may therefore have a greater effect on the protein's isoelectric point than modification of an amino acid residue with a low degree of surface exposure. Methods for determining the degree of surface exposure of an amino acid residue are known in the art. By way of example, the computer program AreaIMol (part of the CCP4 suite of computer programs) can be used to calculate the degree of surface exposure of amino acid residues in a given protein. Surface exposed amino acid residues may also be identified by visual inspection of a protein crystal structure (such as provided by X-ray crystallography). In one embodiment, a surface exposed amino acid residue has a sum AreaIMol value of at least 40.

In one embodiment, the at least one amino acid modification comprises modification of an amino acid residue selected from: an aspartic acid residue, a glutamic acid residue, a histidine residue, a serine residue, a threonine residue, an asparagine residue, a glutamine residue, a cysteine residue, or a tyrosine residue. The present inventors have identified that amino acid residues from this group (negatively charged residues and polar residues) represent particularly suitable targets for modification according to the present invention. Without wishing to be bound by any one theory, the present inventors believe that amino acid residues in this group appear on the surface of a clostridial toxin with a greater frequency than the hydrophobic residues not listed.

In one embodiment, wherein the amino acid modification comprises modification of an amino acid residue selected from an aspartic acid residue, a glutamic acid residue, a histidine residue, a serine residue, a threonine residue, an asparagine residue, a glutamine residue, a cysteine residue, or a tyrosine residue (as described above), the amino acid residue is substituted with a lysine residue or an arginine residue. Thus, in one embodiment, a negatively charged residue or a polar residue is substituted with a positively charged residue, thus increasing the ratio of positive to negative charges and increasing the pI of the clostridial toxin.

In one embodiment, the at least one amino acid modification (as described above) comprises modification of an asparagine amino acid residue or a glutamine amino acid residue (both uncharged, polar residues). In one embodiment, the asparagine or glutamine amino acid residue is substituted with a lysine residue or an arginine residue (both positively charged residues). In one embodiment, the asparagine or glutamine amino acid residue is substituted with a lysine residue. In one embodiment, the asparagine or glutamine amino acid residue is substituted with an arginine residue.

Asparagine and glutamine residues are advantageously suitable for modification as they are polar, form only weak dipole interactions with other residues, and constitute 14% of a typical clostridial toxin molecule (such as BoNT/A).

In one embodiment, the engineered clostridial toxin is a BoNT/A. A reference BoNT/A sequence has the UniProtKB Accession Number P10845.

The present inventors have identified certain amino acids that represent preferred targets for amino acid modification in a BoNT/A clostridial toxin.

In one embodiment, wherein the engineered clostridial toxin is a BoNT/A, said engineered BoNT/A comprises a modification of at least one (for example, at least 1, 2, 3, 4, 5, 10, 15, 20 or 25) amino acid(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086, and GLN 1229; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 10, 15, 20, or 25) amino acid(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086, and GLN 1229; and said amino acid modification(s) increase(s) the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 10, 15, 20, or 25) amino acid(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086, and GLN 1229; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 10, 15, or 20) amino acid(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, and ASP 1086; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 10, 15, 20, 25, or 30) amino acid(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086, ASN 1188, ASP 1213, GLY 1215, ASN 1216, GLN 1229, ASN 1242, ASN 1243, SER 1274, and THR 1277; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 10, 15, 20, 25, or 30) amino acid(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086, ASN 1188, ASP 1213, GLY 1215, ASN 1216, GLN 1229, ASN 1242, ASN 1243, SER 1274, and THR 1277; and said amino acid modification(s) increase(s) the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 10, 15, 20, 25, or 30) amino acid(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086, ASN 1188, ASP 1213, GLY 1215, ASN 1216, GLN 1229, ASN 1242, ASN 1243, SER 1274, and THR 1277; and said amino acid modification(s) increase(s) the isoelectric point (pI) of the engineered BoNT/A to a value that is at least 1 pI unit higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 886, ASN 930, SER 955, GLN 991, ASN 1026, ASN 1052, or GLN 1229; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 886, ASN 930, SER 955, GLN 991, ASN 1026, ASN 1052, or GLN 1229; and said amino acid modification(s) increase(s) the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 886, ASN 930, SER 955, GLN 991, ASN 1026, ASN 1052, or GLN 1229; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 886, ASN 930, SER 955, GLN 991, ASN 1026, ASN 1052, or GLN 1229; and said amino acid modifications increase the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 886, ASN 930, SER 955, GLN 991, ASN 1026, ASN 1052, or GLN 1229; and said amino acid modifications increase the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 886, ASN 930, SER 955, GLN 991, ASN 1026, ASN 1052, or GLN 1229; and said amino acid modifications increase the isoelectric point (pI) of the engineered BoNT/A to a value that is at least one pI unit higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 930, ASN 954, SER 955, GLN 991, ASN 1026, ASN 1052, or GLN 1229; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 930, ASN 954, SER 955, GLN 991, ASN 1026, ASN 1052, or GLN 1229; and said amino acid modification(s) increase(s) the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 930, ASN 954, SER 955, GLN 991, ASN 1026, ASN 1052, or GLN 1229; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 930, ASN 954, SER 955, GLN 991, ASN 1026, ASN 1052, or GLN 1229; and said amino acid modifications increase the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 930, ASN 954, SER 955, GLN 991, ASN 1026, ASN 1052, or GLN 1229; and said amino acid modifications increase the isoelectric point (pI) of the engineered BoNT/A to a value that is at least 0.5 (for example, at least 0.5, 0.6, 0.7, 0.8, 0.9 or 1) pI unit higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 930, ASN 954, SER 955, GLN 991, ASN 1026, ASN 1052, or GLN 1229; and said amino acid modifications increase the isoelectric point (pI) of the engineered BoNT/A to a value that is at least one pI unit higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 930, SER 955, GLN 991, ASN 1025, ASN 1026, ASN 1052, or GLN 1229; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 930, SER 955, GLN 991, ASN 1025, ASN 1026, ASN 1052, or GLN 1229; and said amino acid modification(s) increase(s) the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, or 6) amino acid(s) selected from: ASN 930, SER 955, GLN 991, ASN 1025, ASN 1026, ASN 1052, or GLN 1229; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 930, SER 955, GLN 991, ASN 1025, ASN 1026, ASN 1052, or GLN 1229; and said amino acid modifications increase the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 930, SER 955, GLN 991, ASN 1025, ASN 1026, ASN 1052, or GLN 1229; and said amino acid modifications increase the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following seven amino acids: ASN 930, SER 955, GLN 991, ASN 1025, ASN 1026, ASN 1052, or GLN 1229; and said amino acid modifications increase the isoelectric point (pI) of the engineered BoNT/A to a value that is at least one pI unit higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 6 or 7) amino acid(s) selected from: ASN 1188, ASP 1213, GLY 1215, ASN 1216, ASN 1242, ASN 1243, SER 1274, THR 1277; and said amino acid modification(s) increase(s) the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 6 or 7) amino acid(s) selected from: ASN 1188, ASP 1213, GLY 1215, ASN 1216, ASN 1242, ASN 1243, SER 1274, THR 1277; and said amino acid modification(s) increase(s) the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 6 or 7) amino acid(s) selected from: ASN 1188, ASP 1213, GLY 1215, ASN 1216, ASN 1242, ASN 1243, SER 1274, THR 1277; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue.

In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following eight amino acids: ASN 1188, ASP 1213, GLY 1215, ASN 1216, ASN 1242, ASN 1243, SER 1274, THR 1277; and said amino acid modifications increase the isoelectric point (pI) of the engineered BoNT/A to a value that is at least 0.2 (for example, at least 0.2, 0.3, 0.4, 0.5, 0.6, 0.7, 0.8, 0.9 or 1) pI units higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following eight amino acids: ASN 1188, ASP 1213, GLY 1215, ASN 1216, ASN 1242, ASN 1243, SER 1274, THR 1277; and said amino acid modifications increase the isoelectric point (pI) of the engineered BoNT/A to a value that is at least 0.5 (for example, at least 0.5, 0.6, 0.7, 0.8, 0.9 or 1) pI units higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of the following eight amino acids: ASN 1188, ASP 1213, GLY 1215, ASN 1216, ASN 1242, ASN 1243, SER 1274, THR 1277; and said amino acid modifications increase the isoelectric point (pI) of the engineered BoNT/A to a value that is at least one pI unit higher than the pI of an otherwise identical BoNT/A lacking said amino acid modifications. In one embodiment said modification comprises substitution of the amino acid with a lysine residue or an arginine residue. In one embodiment, said modification comprises substitution of the amino acid with a lysine residue. In one embodiment, said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 6, or all 7) amino acid(s) selected from: ASN 930, SER 955, GLN 991, ASN 1026, ASN 1052, HIS 1064, and GLN 1229; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment said modification comprises substitution of the amino acid with a lysine residue. In one embodiment said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 6, 7, 8, 9, 10, or all 11) amino acid(s) selected from: ASN 886, ASN 930, ASN 954, SER 955, GLN 991, ASN 1026, ASN 1052, HIS 1064, ASN 1080, ASN 1147, and GLN 1229; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/A, said engineered BoNT/A comprises a modification of at least one (for example, at least 1, 2, 3, 4, 5, 6, 7, 8, 9, 10, 11, 12, or all 13) amino acid(s) selected from: ASN 886, ASN 905, ASN 930, ASN 954, SER 955, GLN 991, ASN 1025, ASN 1026, ASN 1052, HIS 1064, ASN 1080, ASN 1147, and GLN 1229; and said amino acid modification(s) increase(s) the isoelectric point (pI) of the engineered BoNT/A to a value that is at least one pI unit higher than the pI of an otherwise identical BoNT/A lacking said amino acid modification(s). In one embodiment said modification comprises substitution of the amino acid with a lysine residue or an arginine residue. In one embodiment said modification comprises substitution of the amino acid with a lysine residue. In one embodiment said modification comprises substitution of the amino acid with an arginine residue.

In one embodiment, the engineered clostridial toxin is a BoNT/B. A reference BoNT/B sequence has the UniProtKB Accession Number P10844.

The present inventors have identified certain amino acids that represent preferred targets for amino acid modification in a BoNT/B clostridial toxin.

In one embodiment, wherein the engineered clostridial toxin is a BoNT/B, said engineered BoNT/B comprises a modification of at least one (for example, at least 1, 2, 3, 4, 5, 10, 15, 20, or 25) amino acid selected from: ASN 873, ASN 874, GLU 892, ASP 895, ASN 906, ASP 940, ASN 948, GLU 949, ASN 958, ASN 959, ASN 979, ASN 990, GLU 993, ASP 994, GLU 997, ASN 1012, ASN 1019, ASP 1030, ASP 1047, ASP 1049, GLU 1065, GLU 1072, GLN 1176, GLU 1189, GLU 1252, and ASN 1273; and said amino acid modification(s) increase(s) the isoelectric point (pI) of the engineered BoNT/B to a value that is at least 0.2

(for example, at least 0.2, 0.3, 0.4, 0.5, 0.6, 0.7, 0.8, 0.9 or 1) pI units higher than the pI of an otherwise identical BoNT/B lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/B, said engineered BoNT/B comprises a modification of at least one (for example, at least 1, 2, 3, 4, 5, 10, 15, 20, or 25) amino acid selected from: ASN 873, ASN 874, GLU 892, ASP 895, ASN 906, ASP 940, ASN 948, GLU 949, ASN 958, ASN 959, ASN 979, ASN 990, GLU 993, ASP 994, GLU 997, ASN 1012, ASN 1019, ASP 1030, ASP 1047, ASP 1049, GLU 1065, GLU 1072, GLN 1176, GLU 1189, GLU 1252, and ASN 1273; and said amino acid modification(s) increase(s) the isoelectric point (pI) of the engineered BoNT/B to a value that is at least 0.5 (for example, at least 0.5, 0.6, 0.7, 0.8, 0.9 or 1) pI units higher than the pI of an otherwise identical BoNT/B lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/B, said engineered BoNT/B comprises a modification of at least one (for example, at least 1, 2, 3, 4, 5, 10, 15, 20, or 25) amino acid selected from: ASN 873, ASN 874, GLU 892, ASP 895, ASN 906, ASP 940, ASN 948, GLU 949, ASN 958, ASN 959, ASN 979, ASN 990, GLU 993, ASP 994, GLU 997, ASN 1012, ASN 1019, ASP 1030, ASP 1047, ASP 1049, GLU 1065, GLU 1072, GLN 1176, GLU 1189, GLU 1252, and ASN 1273; and said amino acid modification(s) increase(s) the isoelectric point (pI) of the engineered BoNT/B to a value that is at least one pI unit higher than the pI of an otherwise identical BoNT/B lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, the engineered clostridial toxin is a BoNT/C$_1$. A reference BoNT/C$_1$ sequence has the UniProtKB Accession Number P18640.

The present inventors have identified certain amino acids that represent preferred targets for amino acid modification in a BoNT/C$_1$ clostridial toxin.

Thus, in one embodiment, wherein the engineered clostridial toxin is a BoNT/C$_1$, said engineered BoNT/C$_1$ comprises a modification of at least one (for example, at least 1, 2, 3, 4, 5, 10, or 15) amino acid selected from: ASN 881, ASP 898, GLU 916, GLU 927, ASN 952, ASN 964, ASN 965, ASN 984, GLU 985, ASP 986, ASP 996, ASN 1000, GLU 1036, ASN 1041, ASP 1062, ASP 1064, GLU 1079, and ASP 1081; and said amino acid modification(s) increase(s) the isoelectric point (pI) of the engineered BoNT/C$_1$ to a value that is at least 0.2 (for example, at least 0.2, 0.3, 0.4, 0.5, 0.6, 0.7, 0.8, 0.9 or 1) pI units higher than the pI of an otherwise identical BoNT/C$_1$ lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

Thus, in one embodiment, wherein the engineered clostridial toxin is a BoNT/C$_1$, said engineered BoNT/C$_1$ comprises a modification of at least one (for example, at least 1, 2, 3, 4, 5, 10, or 15) amino acid selected from: ASN 881, ASP 898, GLU 916, GLU 927, ASN 952, ASN 964, ASN 965, ASN 984, GLU 985, ASP 986, ASP 996, ASN 1000, GLU 1036, ASN 1041, ASP 1062, ASP 1064, GLU 1079, and ASP 1081; and said amino acid modification(s) increase(s) the isoelectric point (pI) of the engineered BoNT/C$_1$ to a value that is at least 0.5 (for example, at least 0.5, 0.6, 0.7, 0.8, 0.9 or 1) pI units higher than the pI of an otherwise identical BoNT/C$_1$ lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/C$_1$, said engineered BoNT/C$_1$ comprises a modification of at least one (for example, at least 1, 2, 3, 4, 5, 10, or 15) amino acid selected from: ASN 881, ASP 898, GLU 916, GLU 927, ASN 952, ASN 964, ASN 965, ASN 984, GLU 985, ASP 986, ASP 996, ASN 1000, GLU 1036, ASN 1041, ASP 1062, ASP 1064, GLU 1079, and ASP 1081; and said amino acid modification(s) increase(s) the isoelectric point (pI) of the engineered BoNT/C$_1$ to a value that is at least one pI unit higher than the pI of an otherwise identical BoNT/C$_1$ lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, the engineered clostridial toxin is a BoNT/D. A reference BoNT/D sequence has the UniProtKB Accession Number P19321.

The present inventors have identified certain amino acids that represent preferred targets for amino acid modification in a BoNT/D clostridial toxin.

In one embodiment, wherein the engineered clostridial toxin is a BoNT/D, said engineered BoNT/D comprises a modification of at least one (for example, at least 1, 2, 3, 4, 5, 10, 15, or 20) amino acid selected from: ASN 877, ASP 893, ASN 894, ASN 898, ASN 920, ASN 945, ASN 948, GLU 957, GLN 958, ASN 959, ASN 968, ASN 979, GLU 1030, ASP 1031, ASP 1033, GLU 1047, GLU 1051, ASN 1052, GLU 1066, and GLN 1122; and said amino acid modification(s) increase(s) the isoelectric point (pI) of the engineered BoNT/D to a value that is at least 0.2 (for example, at least 0.2, 0.3, 0.4, 0.5, 0.6, 0.7, 0.8, 0.9 or 1) pI units higher than the pI of an otherwise identical BoNT/D lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/D, said engineered BoNT/D comprises a modification of at least one (for example, at least 1, 2, 3, 4, 5, 10, 15, or 20) amino acid selected from: ASN 877, ASP 893, ASN 894, ASN 898, ASN 920, ASN 945, ASN 948, GLU 957, GLN 958, ASN 959, ASN 968, ASN 979, GLU 1030, ASP 1031, ASP 1033, GLU 1047, GLU 1051, ASN 1052, GLU 1066, and GLN 1122; and said amino acid modification(s) increase(s) the isoelectric point (pI) of the engineered BoNT/D to a value that is at least 0.5 (for example, at least 0.5, 0.6, 0.7, 0.8, 0.9 or 1) pI units higher than the pI of an otherwise identical BoNT/D lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/D, said engineered BoNT/D comprises a modification of at least one (for example, at least 1, 2, 3, 4, 5, 10, 15, or 20) amino acid selected from: ASN 877, ASP 893, ASN 894, ASN 898, ASN 920, ASN 945, ASN 948, GLU 957, GLN 958, ASN 959, ASN 968, ASN 979, GLU 1030, ASP 1031, ASP 1033, GLU 1047, GLU 1051, ASN 1052, GLU 1066, and GLN 1122; and said amino acid modification(s) increase(s) the isoelectric point (pI) of the engineered BoNT/D to a value that is at least one pI unit higher than the pI of an otherwise identical BoNT/D lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, the engineered clostridial toxin is a BoNT/E. A reference BoNT/E sequence has the UniProtKB Accession Number Q00496.

The present inventors have identified certain amino acids that represent preferred targets for amino acid modification in a BoNT/E clostridial toxin.

In one embodiment, wherein the engineered clostridial toxin is a BoNT/E, said engineered BoNT/E comprises a modification of at least one (for example, at least 1, 2, 3, 4, 5, 10, 15, 20, or 25) amino acid selected from: ASN 859, ASP 860, ASN 892, ASP 893, ASP 904, ASP 909, ASN 928, ASN 932, ASN 934, ASN 935, GLU 936, ASP 945, ASN 946, ASN 947, ASN 966, ASN 976, ASN 979, ASN 981, ASP 985, GLN 1014, ASN 1019, ASN 1022, ASP 1027, ASN 1035, and ASN 1140; and said amino acid modification(s) increase(s) the isoelectric point (pI) of the engineered BoNT/E to a value that is at least 0.2 (for example, at least 0.2, 0.3, 0.4, 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/E, said engineered BoNT/E comprises a modification of at least one (for example, at least 1, 2, 3, 4, 5, 10, 15, 20, or 25) amino acid selected from: ASN 859, ASP 860, ASN 892, ASP 893, ASP 904, ASP 909, ASN 928, ASN 932, ASN 934, ASN 935, GLU 936, ASP 945, ASN 946, ASN 947, ASN 966, ASN 976, ASN 979, ASN 981, ASP 985, GLN 1014, ASN 1019, ASN 1022, ASP 1027, ASN 1035, and ASN 1140; and said amino acid modification(s) increase(s) the isoelectric point (pI) of the engineered BoNT/E to a value that is at least 0.5 (for example, at least 0.5, 0.6, 0.7, 0.8, 0.9 or 1) pI units higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/E, said engineered BoNT/E comprises a modification of at least one (for example, at least 1, 2, 3, 4, 5, 10, 15, 20, or 25) amino acid selected from: ASN 859, ASP 860, ASN 892, ASP 893, ASP 904, ASP 909, ASN 928, ASN 932, ASN 934, ASN 935, GLU 936, ASP 945, ASN 946, ASN 947, ASN 966, ASN 976, ASN 979, ASN 981, ASP 985, GLN 1014, ASN 1019, ASN 1022, ASP 1027, ASN 1035, and ASN 1140; and said amino acid modification(s) increase(s) the isoelectric point (pI) of the engineered BoNT/E to a value that is at least one pI unit higher than the pI of an otherwise identical BoNT/E lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, the engineered clostridial toxin is a BoNT/F. A reference BoNT/F sequence has the UniProtKB Accession Number YP_001390123.

The present inventors have identified certain amino acids that represent preferred targets for amino acid modification in a BoNT/F clostridial toxin.

In one embodiment, wherein the engineered clostridial toxin is a BoNT/F, said engineered BoNT/F comprises a modification of at least one (for example, at least 1, 2, 3, 4, 5, 10, 15, or 20) amino acid selected from: ASN 879, ASP 896, ASN 922, ASN 923, ASN 928, ASN 947, ASN 950, ASN 952, ASN 953, GLU 954, ASN 963, ASN 964, ASN 965, ASN 987, GLN 997, ASN 1037, ASP 1040, ASP 1045, ASN 1055, and ASP 1056; and said amino acid modification(s) increase(s) the isoelectric point (pI) of the engineered BoNT/F to a value that is at least 0.2 (for example, at least 0.2, 0.3, 0.4, 0.5, 0.6, 0.7, 0.8, 0.9 or 1) pI units higher than the pI of an otherwise identical BoNT/F lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/F, said engineered BoNT/F comprises a modification of at least one (for example, at least 1, 2, 3, 4, 5, 10, 15, or 20) amino acid selected from: ASN 879, ASP 896, ASN 922, ASN 923, ASN 928, ASN 947, ASN 950, ASN 952, ASN 953, GLU 954, ASN 963, ASN 964, ASN 965, ASN 987, GLN 997, ASN 1037, ASP 1040, ASP 1045, ASN 1055, and ASP 1056; and said amino acid modification(s) increase(s) the isoelectric point (pI) of the engineered BoNT/F to a value that is at least 0.5 (for example, at least 0.5, 0.6, 0.7, 0.8, 0.9 or 1) pI unit higher than the pI of an otherwise identical BoNT/F lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/F, said engineered BoNT/F comprises a modification of at least one (for example, at least 1, 2, 3, 4, 5, 10, 15, or 20) amino acid selected from: ASN 879, ASP 896, ASN 922, ASN 923, ASN 928, ASN 947, ASN 950, ASN 952, ASN 953, GLU 954, ASN 963, ASN 964, ASN 965, ASN 987, GLN 997, ASN 1037, ASP 1040, ASP 1045, ASN 1055, and ASP 1056; and said amino acid modification(s) increase(s) the isoelectric point (pI) of the engineered BoNT/F to a value that is at least one pI unit higher than the pI of an otherwise identical BoNT/F lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, the engineered clostridial toxin is a BoNT/G. A reference BoNT/G sequence has the UniProtKB Accession Number Q60393.

The present inventors have identified certain amino acids that represent preferred targets for amino acid modification in a BoNT/G clostridial toxin.

In one embodiment, wherein the engineered clostridial toxin is a BoNT/G, said engineered BoNT/G comprises a modification of at least one (for example, at least 1, 2, 3, 4, 5, 10, or 15) amino acid selected from: ASP 900, ASN 909, ASN 910, GLU 912, ASN 913, ASN 945, ASN 947, GLU 956, ASN 965, ASP 966, ASN 986, ASN 1001, ASN 1038, ASP 1040, ASN 1046, ASP 1057, GLU 1073, ASN 1075, and ASN 1090; and said amino acid modification(s) increase(s) the isoelectric point (pI) of the engineered BoNT/G to a value that is at least 0.2 (for example, at least 0.2, 0.3, 0.4, 0.5, 0.6, 0.7, 0.8, 0.9 or 1) pI units higher than the pI of an otherwise identical BoNT/G lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/G, said engineered BoNT/G comprises a modification of at least one (for example, at least 1, 2, 3, 4, 5, 10, or 15) amino acid selected from: ASP 900, ASN 909, ASN 910, GLU 912, ASN 913, ASN 945, ASN 947, GLU 956, ASN 965, ASP 966, ASN 986, ASN 1001, ASN 1038, ASP 1040, ASN 1046, ASP 1057, GLU 1073, ASN 1075, and ASN 1090; and said amino acid modification(s) increase(s) the isoelectric point (pI) of the engineered BoNT/G to a value that is at least 0.5 (for example, at least 0.5, 0.6, 0.7, 0.8, 0.9 or 1) pI units higher than the pI of an otherwise identical BoNT/G lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a BoNT/G, said engineered BoNT/G comprises a modification of at least one (for example, at least 1, 2, 3, 4, 5, 10, or 15) amino acid selected from: ASP 900, ASN 909, ASN 910, GLU 912, ASN 913, ASN 945, ASN 947, GLU 956, ASN 965, ASP 966, ASN 986, ASN 1001, ASN 1038, ASP 1040, ASN 1046, ASP 1057, GLU 1073, ASN 1075, and ASN 1090; and said amino acid modification(s) increase(s) the isoelectric point (pI) of the engineered BoNT/G to a value that is at least one pI unit higher than the pI of an otherwise identical BoNT/G lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, the engineered clostridial toxin is a TeNT. A reference TeNT sequence has the UniProtKB Accession Number P04958.

The present inventors have identified certain amino acids that represent preferred targets for amino acid modification in a TeNT clostridial toxin.

In one embodiment, wherein the engineered clostridial toxin is a TeNT, said engineered TeNT comprises a modification of at least one (for example, at least 1, 2, 3, 4, 5, 10, or 15) amino acid selected from: ASN 893, ASP 894, ASP 911, ASN 919, ASN 927, ASN 928, GLU 929, GLN 968, ASN 972, GLU 973, GLU 1010, ASP 1018, ASN 1079, ASN 1080, ASN 1081, and ASN 1097; and said amino acid modification(s) increase(s) the isoelectric point (pI) of the engineered TeNT to a value that is at least 0.2 (for example, at least 0.2, 0.3, 0.4, 0.5, 0.6, 0.7, 0.8, 0.9 or 1) pI unit higher than the pI of an otherwise identical TeNT lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a TeNT, said engineered TeNT comprises a modification of at least one (for example, at least 1, 2, 3, 4, 5, 10, or 15) amino acid selected from: ASN 893, ASP 894, ASP 911, ASN 919, ASN 927, ASN 928, GLU 929, GLN 968, ASN 972, GLU 973, GLU 1010, ASP 1018, ASN 1079, ASN 1080, ASN 1081, and ASN 1097; and said amino acid modification(s) increase(s) the isoelectric point (pI) of the engineered TeNT to a value that is at least 0.5 (for example, at least 0.5, 0.6, 0.7, 0.8, 0.9 or 1) pI unit higher than the pI of an otherwise identical TeNT lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

In one embodiment, wherein the engineered clostridial toxin is a TeNT, said engineered TeNT comprises a modification of at least one (for example, at least 1, 2, 3, 4, 5, 10, or 15) amino acid selected from: ASN 893, ASP 894, ASP 911, ASN 919, ASN 927, ASN 928, GLU 929, GLN 968, ASN 972, GLU 973, GLU 1010, ASP 1018, ASN 1079, ASN 1080, ASN 1081, and ASN 1097; and said amino acid modification(s) increase(s) the isoelectric point (pI) of the engineered TeNT to a value that is at least one pI unit higher than the pI of an otherwise identical TeNT lacking said amino acid modification(s). In one embodiment said modification comprises substitution of the amino acid with a lysine residue or an arginine residue. In one embodiment, said modification comprises substitution of the amino acid with a lysine residue. In one embodiment said modification comprises substitution of the amino acid with an arginine residue.

The present invention is suitable for application to many different varieties of clostridial toxin. Thus, in the context of the present invention, the term "clostridial toxin" embraces toxins produced by C. botulinum (botulinum neurotoxin serotypes A, B, C$_1$, D, E, F and G), C. tetani (tetanus neurotoxin), C. butyricum (botulinum neurotoxin serotype E), and C. baratii (botulinum neurotoxin serotype F), as well as modified clostridial toxins or derivatives derived from any of the foregoing. The term "clostridial toxin" also embraces botulinum neurotoxin serotype H.

Botulinum neurotoxin (BoNT) is produced by C. botulinum in the form of a large protein complex, consisting of BoNT itself complexed to a number of accessory proteins. There are at present eight different classes of botulinum neurotoxin, namely: botulinum neurotoxin serotypes A, B, C$_1$, D, E, F, G, and H, all of which share similar structures and modes of action. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are absorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/ vesicle-associated membrane protein (VAMP); BoNT/C$_1$, BoNT/A and BoNT/E cleave the synaptosomal-associated protein of 25 kDa (SNAP-25); and BoNT/C$_1$ cleaves syntaxin.

Tetanus toxin is produced in a single serotype by C. tetani. C. butyricum produces BoNT/E, while C. baratii produces BoNT/F.

The term "clostridial toxin" is also intended to embrace modified clostridial toxins and derivatives thereof, including but not limited to those described below. A modified clostridial toxin or derivative may contain one or more amino acids that has been modified as compared to the native (unmodified) form of the clostridial toxin, or may contain one or more inserted amino acids that are not present in the native (unmodified) form of the clostridial toxin. By way of example, a modified clostridial toxin may have modified amino acid sequences in one or more domains relative to the native (unmodified) clostridial toxin sequence. Such modifications may modify functional aspects of the toxin, for example biological activity or persistence. Thus, in one embodiment, the engineered clostridial toxin of the invention is an engineered modified clostridial toxin, or an engineered modified clostridial toxin derivative, or an engineered clostridial toxin derivative.

A modified clostridial toxin may have one or more modifications in the amino acid sequence of the heavy chain (such as a modified H$_C$ domain), wherein said modified heavy chain binds to target nerve cells with a higher or lower affinity than the native (unmodified) clostridial toxin. Such modifications in the H$_C$ domain can include modifying residues in the ganglioside binding site of the H$_C$ domain or in the protein (SV2 or synaptotagmin) binding site that alter binding to the ganglioside receptor and/or the protein receptor of the target nerve cell. Examples of such modified clostridial toxins are described in WO 2006/027207 and WO 2006/114308, both of which are hereby incorporated by reference in their entirety.

A modified clostridial toxin may have one or more modifications in the amino acid sequence of the light chain, for example modifications in the substrate binding or catalytic domain which may alter or modify the SNARE protein specificity of the modified LC. Examples of such modified clostridial toxins are described in WO 2010/120766 and US 2011/0318385, both of which are hereby incorporated by reference in their entirety.

A modified clostridial toxin may comprise one or more modifications that increases or decreases the biological activity and/or the biological persistence of the modified clostridial toxin. For example, a modified clostridial toxin may comprise a leucine- or tyrosine-based motif, wherein said motif increases or decreases the biological activity and/or the biological persistence of the modified clostridial toxin. Suitable leucine-based motifs include xDxxxLL, xExxxLL, xExxxLL, and xExxxLM (wherein x is any amino acid). Suitable tyrosine-based motifs include Y-x-x-Hy (wherein Hy is a hydrophobic amino acid). Examples of modified clostridial toxins comprising leucine- and tyrosine-based motifs are described in WO 2002/08268, which is hereby incorporated by reference in its entirety.

The term "clostridial toxin" is intended to embrace hybrid and chimeric clostridial toxins. A hybrid clostridial toxin comprises at least a portion of a light chain from one clostridial toxin or subtype thereof, and at least a portion of a heavy chain from another clostridial toxin or clostridial toxin subtype. In one embodiment the hybrid clostridial toxin may contain the entire light chain of a light chain from one clostridial toxin subtype and the heavy chain from another clostridial toxin subtype. In another embodiment, a chimeric clostridial toxin may contain a portion (e.g. the binding domain) of the heavy chain of one clostridial toxin subtype, with another portion of the heavy chain being from another clostridial toxin subtype. Similarly or alternatively, the therapeutic element may comprise light chain portions from different clostridial toxins. Such hybrid or chimeric clostridial toxins are useful, for example, as a means of delivering the therapeutic benefits of such clostridial toxins to patients who are immunologically resistant to a given clostridial toxin subtype, to patients who may have a lower than average concentration of receptors to a given clostridial toxin heavy chain binding domain, or to patients who may have a protease-resistant variant of the membrane or vesicle toxin substrate (e.g., SNAP-25, VAMP and syntaxin). Hybrid and chimeric clostridial toxins are described in U.S. Pat. No. 8,071,110, which publication is hereby incorporated by reference in its entirety. Thus, in one embodiment, the engineered clostridial toxin of the invention is an engineered hybrid clostridial toxin, or an engineered chimeric clostridial toxin.

The term "clostridial toxin" is intended to embrace re-targeted clostridial toxins. In a re-targeted clostridial toxin, the clostridial toxin is modified to include an exogenous ligand known as a Targeting Moiety (TM). The TM is selected to provide binding specificity for a desired target cell, and as part of the re-targeting process the native binding portion of the clostridial toxin (e.g. the $H_C$ domain, or the $H_{CC}$ domain) may be removed. Re-targeting technology is described, for example, in: EP-B-0689459; WO 1994/021300; EP-B-0939818; U.S. Pat. No. 6,461,617; U.S. Pat. No. 7,192,596; WO 1998/007864; EP-B-0826051; U.S. Pat. No. 5,989,545; U.S. Pat. No. 6,395,513; U.S. Pat. No. 6,962,703; WO 1996/033273; EP-B-0996468; U.S. Pat. No. 7,052,702; WO 1999/017806; EP-B-1107794; U.S. Pat. No. 6,632,440; WO 2000/010598; WO 2001/21213; WO 2006/059093; WO 2000/62814; WO 2000/04926; WO 1993/15766; WO 2000/61192; and WO 1999/58571; all of which are hereby incorporated by reference in their entirety. Thus, in one embodiment, the engineered clostridial toxin of the invention is an engineered re-targeted clostridial toxin.

The present invention also embraces clostridial toxins that have a non-native protease cleavage site. In such clostridial toxins, the native protease cleavage site (also known as the activation site, as described above) is modified or replaced with a protease cleavage site that is not native to that clostridial toxin (i.e. an exogenous cleavage site). Such a site will require an exogenous protease for cleavage, which allows for improved control over the timing and location of cleavage events. Non-native protease cleavage sites that may be employed in clostridial toxins include:

| | |
|---|---|
| Enterokinase | (DDDDK↓) (SEQ ID NO: 11) |
| Factor Xa | (IEGR↓/IDGR↓) (SEQ ID NO: 12) |
| TEV (Tobacco Etch virus) | (ENLYFQ↓G) (SEQ ID NO: 13) |
| Thrombin | (LVPR↓GS) (SEQ ID NO: 14) |
| PreScission | (LEVLFQ↓GP) (SEQ ID NO: 15). |

Additional protease cleavage sites include recognition sequences that are cleaved by a non-cytotoxic protease, for example by the light chain of a clostridial neurotoxin. These include the SNARE (e.g. SNAP-25, syntaxin, VAMP) protein recognition sequences that are cleaved by non-cytotoxic proteases such as the light chain of a clostridial neurotoxin. Clostridial toxins comprising non-native protease cleavage sites are described in U.S. Pat. No. 7,132,259, EP 1206554-B2 and US 2007/0166332, all of which are hereby incorporated by reference in their entirety. Also embraced by the term protease cleavage site is an intein, which is a self-cleaving sequence. The self-splicing reaction is controllable, for example by varying the concentration of reducing agent present.

The present invention also embraces clostridial toxins comprising a "destructive cleavage site". In said clostridial toxins, a non-native protease cleavage site is incorporated into the clostridial toxin, at a location chosen such that cleavage at said site will decrease the activity of, or inactivate, the clostridial toxin. The destructive protease cleavage site can be susceptible to cleavage by a local protease, in the event that the clostridial toxin, following administration, migrates to a non-target location. Suitable non-native protease cleavage sites include those described above. Clostridial toxins comprising a destructive cleavage site are described in WO 2010/094905 and WO 2002/044199, both of which are hereby incorporated by reference in their entirety.

The engineered clostridial toxins of the present invention, especially the light chain component thereof, may be PEGylated—this may help to increase stability, for example duration of action of the light chain component. PEGylation is particularly preferred when the light chain comprises a BoNT/A, B or $C_1$ protease. PEGylation preferably includes the addition of PEG to the N-terminus of the light chain component. By way of example, the N-terminus of a light chain may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is hereby incorporated by reference in its entirety.

The engineered clostridial toxins of the present invention may be free from the complexing proteins that are present in a naturally occurring clostridial toxin complex.

An engineered clostridial toxin of the present invention may also comprise a limited number of non-standard amino acids. Thus, in addition to the 20 standard amino acids, non-standard amino acids (such as 4-hydroxyproline, 6-N-methyl lysine, 2-aminoisobutyric acid, isovaline and α-methyl serine) may be substituted for amino acid residues of the engineered clostridial toxins of the present invention. A limited number of non-conservative amino acids, amino acids that are not encoded by the genetic code, and unnatural amino acids may be substituted for clostridial polypeptide amino acid residues. The engineered clostridial toxins of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994.

The engineered clostridial toxins of the present invention can be produced using recombinant nucleic acid technologies. Thus, in one embodiment, an engineered clostridial toxin (as described above) is a recombinant engineered clostridial toxin.

In another aspect, the present invention provides a nucleic acid (for example, a DNA) comprising a nucleic acid sequence encoding an engineered clostridial toxin as described above. In one embodiment, the nucleic acid sequence is prepared as part of a DNA vector comprising a promoter and a terminator.

In a preferred embodiment, the vector has a promoter selected from:

| Promoter | Induction Agent | Typical Induction Condition |
| --- | --- | --- |
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

In another preferred embodiment, the vector has a promoter selected from:

| Promoter | Induction Agent | Typical Induction Condition |
| --- | --- | --- |
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |
| T5-lac operator | IPTG | 0.2 mM (0.05-2.0 mM) |

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

The DNA construct of the present invention is preferably designed in silico, and then synthesised by conventional DNA synthesis techniques.

The above-mentioned nucleic acid sequence information is optionally modified for codon-biasing according to the ultimate host cell (e.g. E. coli) expression system that is to be employed.

In one embodiment, the nucleic acid sequence encoding an engineered clostridial toxin as described above is a nucleic acid sequence having at least 70% (for example, at least 75, 80, 85, 90, 95, 97, 98 or 99%) sequence identity to a nucleic acid sequence selected from SEQ ID NOs: 3, 5, 7 and 9.

In one aspect, the present invention provides a nucleic acid sequence having at least 70% (for example, at least 75, 80, 85, 90, 95, 97, 98 or 99%) sequence identity to a nucleic acid sequence selected from SEQ ID NOs: 3, 5, 7 and 9. In one embodiment, the nucleic acid sequence has at least 90% sequence identity to a nucleic acid sequence selected from SEQ ID NOs: 3, 5, 7 and 9.

The present invention also provides polypeptides encoded by nucleic acid sequences as described above. Thus, in one aspect, the present invention provides a polypeptide comprising an amino acid sequence having at least 70% (for example, at least 75, 80, 85, 90, 95, 97, 98 or 99%) sequence identity to an amino acid sequence selected from SEQ ID NOs: 4, 6, 8 and 10. In one embodiment, the amino acid sequence has at least 90% sequence identity to an amino acid sequence selected from SEQ ID NOs: 4, 6, 8 and 10.

In one embodiment, the engineered clostridial toxin of the invention is an engineered BoNT/A as described above, and said engineered BoNT/A comprises (or consists of) an amino acid sequence having at least 70% (for example, at least 75, 80, 85, 90, 95, 97, 98, 99, 99.5 or 99.9%) sequence identity to an amino acid sequence selected from SEQ ID NOs: 4, 6, 8 and 10.

In one embodiment, the engineered clostridial toxin of the invention is an engineered BoNT/A as described above, and said engineered BoNT/A comprises (or consists of) the amino acid sequence of SEQ ID NO: 4, 6, 8 or 10.

In one aspect, the invention provides a polypeptide comprising (or consisting of) the amino acid sequence of SEQ ID NO: 4, 6, 8 or 10.

In one aspect, the invention provides a nucleic acid encoding an engineered clostridial toxin as described above, wherein said nucleic acid comprises a nucleic acid sequence having at least 70% (for example, at least 75, 80, 85, 90, 95, 97, 98, 99, 99.5 or 99.9%) sequence identity to a nucleic acid sequence selected from SEQ ID NOs: 3, 5, 7 and 9. In one embodiment, the nucleic acid comprises (or consists of) the nucleic acid sequence of SEQ ID NO: 3, 5, 7 or 9.

In one aspect, the invention provides a nucleic acid comprising (or consisting of) the nucleic acid sequence of SEQ ID NO: 3, 5, 7 or 9.

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

In one aspect, the present invention provides a method of producing a single-chain engineered clostridial toxin protein having a light chain and a heavy chain, the method comprising expressing a nucleic acid (said nucleic acid being as described above) in a suitable host cell, lysing the host cell to provide a host cell homogenate containing the single-chain engineered clostridial toxin protein, and isolating the single-chain engineered clostridial toxin protein.

In another aspect, the present invention provides a method of activating an engineered clostridial toxin, the method comprising providing a single-chain engineered clostridial toxin protein obtainable by the method of producing a single-chain engineered clostridial toxin protein as described above, contacting the polypeptide with a protease that cleaves the polypeptide at a recognition site (cleavage site) located between the light chain and heavy chain, thereby converting the polypeptide into a di-chain polypeptide wherein the light chain and heavy chain are joined together by a disulphide bond.

The engineered clostridial toxins of the invention may be used to prevent or treat certain medical or cosmetic diseases and conditions. Thus, in a further aspect, the present invention provides an engineered clostridial toxin as described above, for use in medicine.

In a related aspect, the present invention provides an engineered clostridial toxin as described above, for use in the prevention or treatment of a disease or condition selected from: strabismus, blepharospasm, squint, dystonia (e.g. spasmodic dystonia, oromandibular dystonia, focal dystonia, tardive dystonia, laryngeal dystonia, limb dystonia, cervical dystonia), torticollis (e.g. spasmodic torticollis), beauty therapy (cosmetic) applications benefiting from cell/muscle incapacitation (via SNARE down-regulation or inactivation), neuromuscular disorder or condition of ocular motility (e.g. concomitant strabismus, vertical strabismus, lateral rectus palsy, nystagmus, dysthyroid myopathy), writer's cramp, blepharospasm, bruxism, Wilson's disease, tremor, tics, segmental myoclonus, spasms, spasticity due to chronic multiple sclerosis, spasticity resulting in abnormal bladder control, animus, back spasm, charley horse, tension headaches, levator pelvic syndrome, spina bifida, tardive dyskinesia, Parkinson's disease, stuttering, hemifacial spasm, eyelid disorder, cerebral palsy, focal spasticity, spasmodic colitis, neurogenic bladder, anismus, limb spasticity, tics, tremors, bruxism, anal fissure, achalasia, dysphagia, lacrimation, hyperhydrosis, excessive salivation, excessive gastrointestinal secretions, muscle pain (e.g. pain from muscle spasms), headache pain (e.g. tension headache), brow furrows, skin wrinkles, cancer, uterine disorders, urogenital disorders, urogenital-neurological disorders, chronic neurogenic inflammation, and a smooth muscle disorder.

In use, the present invention employs a pharmaceutical composition, comprising an engineered clostridial toxin, together with at least one component selected from a pharmaceutically acceptable carrier, excipient, adjuvant, propellant and/or salt.

The engineered clostridial toxins of the present invention may be formulated for oral, parenteral, continuous infusion, inhalation or topical application. Compositions suitable for injection may be in the form of solutions, suspensions or emulsions, or dry powders which are dissolved or suspended in a suitable vehicle prior to use.

In the case of an engineered clostridial toxin that is to be delivered locally, the engineered clostridial toxin may be formulated as a cream (e.g. for topical application), or for sub-dermal injection.

Local delivery means may include an aerosol, or other spray (e.g. a nebuliser). In this regard, an aerosol formulation of an engineered clostridial toxin enables delivery to the lungs and/or other nasal and/or bronchial or airway passages.

Engineered clostridial toxins of the invention may be administered to a patient by intrathecal or epidural injection in the spinal column at the level of the spinal segment involved in the innervation of an affected organ.

A preferred route of administration is via laproscopic and/or localised, particularly intramuscular, injection.

The dosage ranges for administration of the engineered clostridial toxins of the present invention are those to produce the desired therapeutic effect. It will be appreciated that the dosage range required depends on the precise nature of the engineered clostridial toxin or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages (per kg weight of patient) are in the range 0.0001-1 ng/kg, preferably 0.0001-0.5 ng/kg, more preferably 0.002-0.5 ng/kg, and particularly preferably 0.004-0.5 ng/kg. The unit dosage can vary from less than 1 picogram to 30 ng, but typically will be in the region of 0.01 to 1 ng per dose, which may be administered daily or preferably less frequently, such as weekly or six monthly. A particularly preferred dosing regimen is based on 0.05 ng of engineered clostridial toxin as the 1× dose. In this regard, preferred dosages are in the range 1×-100× (i.e. 0.05-5 ng).

Fluid dosage forms are typically prepared utilising the engineered clostridial toxin and a pyrogen-free sterile vehicle. The engineered clostridial toxin, depending on the vehicle and concentration used, can be either dissolved or suspended in the vehicle. In preparing solutions the engineered clostridial toxin can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Administration in accordance with the present invention may take advantage of a variety of delivery technologies including microparticle encapsulation, viral delivery systems or high-pressure aerosol impingement.

LIST OF FIGURES

FIG. 2A depicts the percentage of SNAP-25 cleaved in rat embryonic spinal cord neurons (eSCN) by Cat5v2(K1064H/N954K) as compared to that by nBoNT/A1.

FIG. 2B depicts the percentage of SNAP-25 cleaved in rat embryonic spinal cord neurons (eSCN) 4 Cat5v2(K1064H/N886K) as compared to that by nBoNT/A1.

FIG. 2C depicts the percentage of SNAP-25 cleaved in rat embryonic spinal cord neurons (eSCN) 4 Cat5v2(K106411/K1025K) as compared to that cleaved by nBoNT/A1.

Figures 2A, 2B:
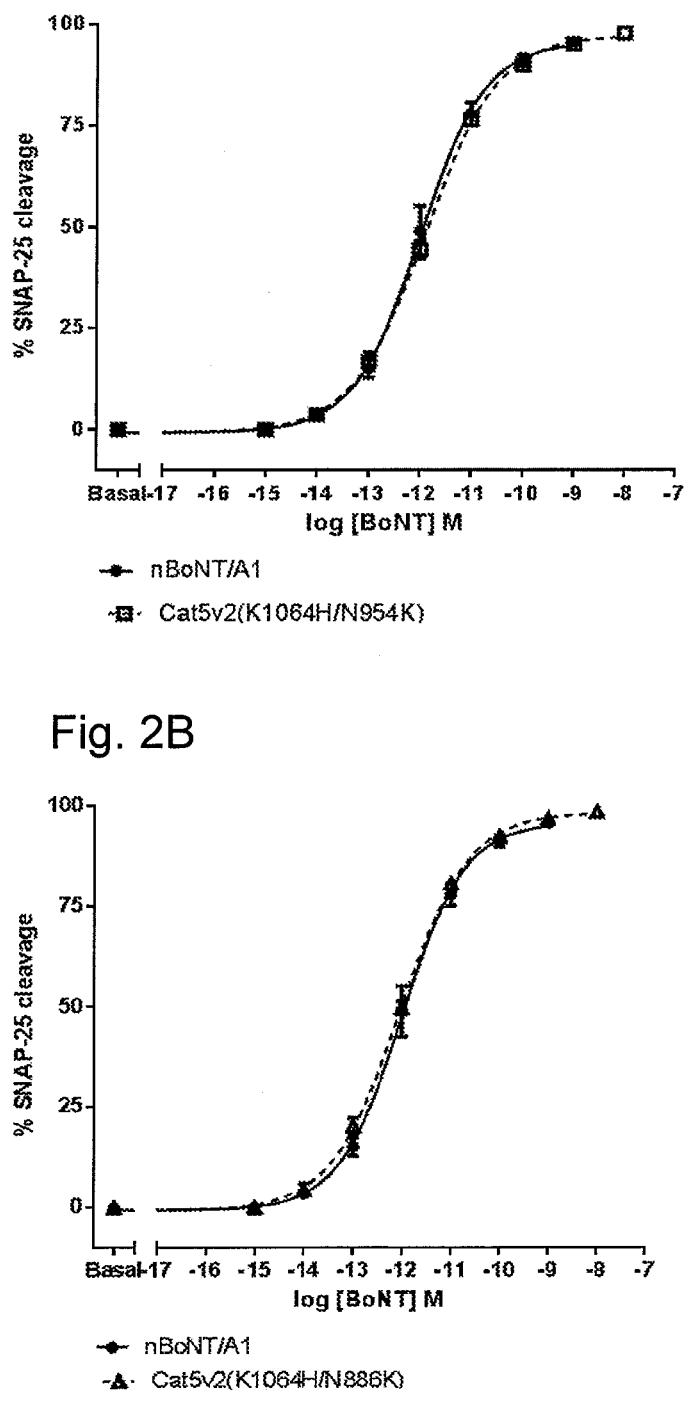
Figures 2C, 2D:
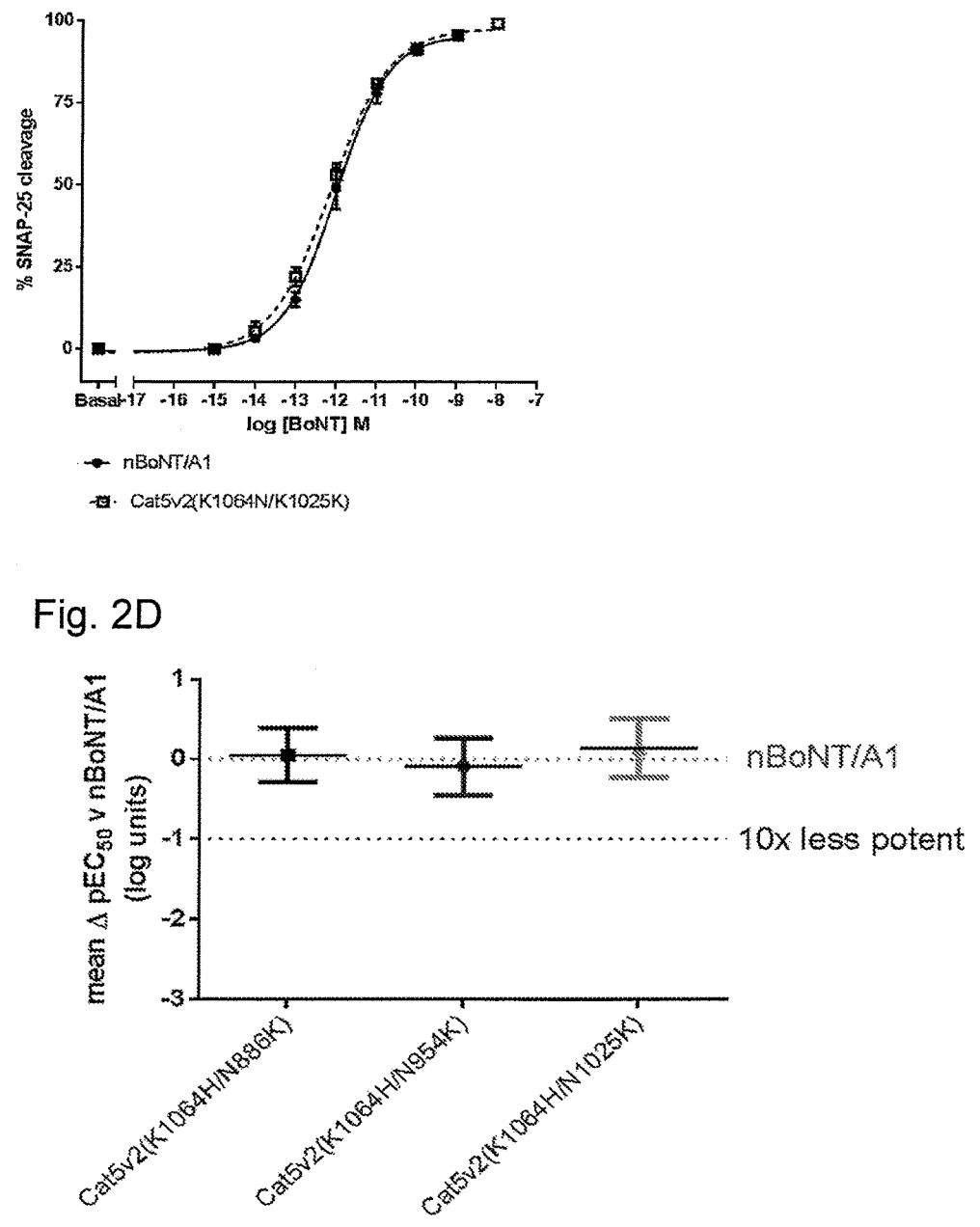
Figure 1:
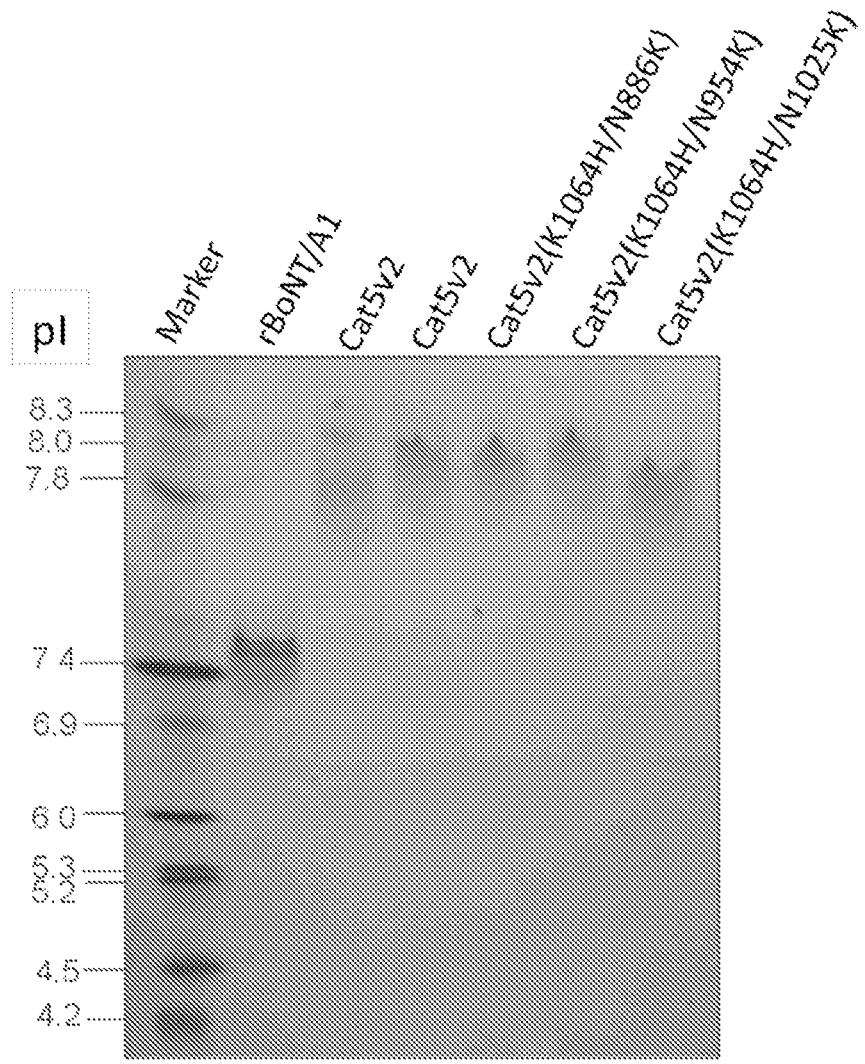
FIG. 1 depicts an isoelectric focusing (IEF) gel comparing the pI of rBoNT/A1 with that of Cat5v2, Cat5v2(K1064H/N954K), Cat5v2(K1064H/N886K), and Cat5v2 (K106411/N1025K).

FIG. 2D depicts the relative potency of Cat5v2(K1064H/N954K), Cat5v2(K1064H/N886K), and Cat5v2(K1064H/N1025K), relative to nBoNT/A1 (List Biological Laboratories) in the rat eSCN SNAP25 cleavage potency assay. Briefly, rat embryonic spinal cord neurons were cultured for three weeks and treated with Cat5v4 for 24 hours before Western blotting with SNAP-25 specific antibody. The data is mean±SEM from three independent experiments in triplicate. Each point corresponds to an individual batch and is a mean of 3 independent $pEC_{50}$ determinations based on an 8-point concentration response curve (CRC). Each concentration in the CRC was assessed in triplicate. Potency comparisons are made to a mean of List batches, pooled data n=24. Data are mean±SEM of n=3 batches per Cat5v4.

FIG. 3 depicts the respective potencies (t50) of nBoNT/A1, Cat5v2(K1064H/N954K), Cat5v2(K1064H/N886K), and Cat5v2(K106411/N1025K). in the mouse phrenic nerve hemi-diaphragm assay (mPNHD). In the assay mouse phrenic nerve hemi-diaphragm tissue was incubated with Cat5v4 or native BoNT/A1 and diaphragm contractile force was recorded until the contraction was no longer detectable or after 140 minutes. Each point corresponds to independent determinations. The t50 value is the time required to inhibit the contractile force of the mouse hemi-diaphragm by 50%.

SEQUENCES

SEQ ID NO: 1. BoNT/A1 nucleic acid sequence.
ATGCCATTCGTCAACAAGCAATTCAACTACAAAGA

CCCAGTCAACGGCGTCGACATCGCATACATCAAG

ATTCCGAACGCCGGTCAAATGCAGCCGGTTAAGGC

TTTTAAGATCCACAACAAGATTTGGGTTATCCCG

GAGCGTGACACCTTCACGAACCCGGAAGAAGGCGA

TCTGAACCCGCCACCGGAAGCGAAGCAAGTCCCT

GTCAGCTACTACGATTCGACGTACCTGAGCACGGA

TAACGAAAAAGATAACTACCTGAAAGGTGTGACC

AAGCTGTTCGAACGTATCTACAGCACGGATCTGGG

TCGCATGCTGCTGACTAGCATTGTTCGCGGTATC

CCGTTCTGGGGTGGTAGCACGATTGACACCGAACT

GAAGGTTATCGACACTAACTGCATTAACGTTATT

CAACCGGATGGTAGCTATCGTAGCGAAGAGCTGAA

TCTGGTCATCATTGGCCCGAGCGCAGACATTATC

CAATTCGAGTGCAAGAGCTTTGGTCACGAGGTTCT

GAATCTGACCCGCAATGGCTATGGTAGCACCCAG

TACATTCGTTTTTCGCCGGATTTTACCTTCGGCTT

TGAAGAGAGCCTGGAGGTTGATACCAATCCGTTG

CTGGGTGCGGGCAAATTCGCTACCGATCCGGCTGT

CACGCTGGCCCATGAACTGATCCACGCAGGCCAC

CGCCTGTACGGCATTGCCATCAACCCAAACCGTGT

GTTCAAGGTTAATACGAATGCATACTACGAGATG

AGCGGCCTGGAAGTCAGCTTCGAAGAACTGCGCAC

CTTCGGTGGCCATGACGCTAAATTCATTGACAGC

TTGCAAGAGAATGAGTTCCGTCTGTACTACTATAA

CAAATTCAAAGACATTGCAAGCACGTTGAACAAG

GCCAAAAGCATCGTTGGTACTACCGCGTCGTTGCA

GTATATGAAGAATGTGTTTAAAGAGAAGTACCTG

CTGTCCGAGGATACCTCCGGCAAGTTTAGCGTTGA

TAAGCTGAAGTTTGACAAACTGTACAAGATGCTG

ACCGAGATTTACACCGAGGACAACTTTGTGAAATT

CTTCAAAGTGTTGAATCGTAAAACCTATCTGAAT

TTTGACAAAGCGGTTTTCAAGATTAACATCGTGCC

GAAGGTGAACTACACCATCTATGACGGTTTTAAC

CTGCGTAACACCAACCTGGCGGCGAACTTTAACGG

TCAGAATACGGAAATCAACAACATGAATTTCACG

AAGTTGAAGAACTTCACGGGTCTGTTCGAGTTCTA

-continued

TAAGCTGCTGTGCGTGCGCGGTATCATCACCAGC

AAAACCAAAAGCCTGGACAAAGGCTACAACAAGGC

GCTGAATGACCTGTGCATTAAGGTAAACAATTGG

GATCTGTTCTTTTCGCCATCCGAAGATAATTTTAC

CAACGACCTGAACAAGGGTGAAGAAATCACCAGC

GATACGAATATTGAAGCAGCGGAAGAGAATATCAG

CCTGGATCTGATCCAGCAGTACTATCTGACCTTT

AACTTCGACAATGAACCGGAGAACATTAGCATTGA

GAATCTGAGCAGCGACATTATCGGTCAGCTGGAA

CTGATGCCGAATATCGAACGTTTCCCGAACGGCAA

AAAGTACGAGCTGGACAAGTACACTATGTTCCAT

TACCTGCGTGCACAGGAGTTTGAACACGGTAAAAG

CCGTATCGCGCTGACCAACAGCGTTAACGAGGCC

CTGCTGAACCCGAGCCGTGTCTATACCTTCTTCAG

CAGCGACTATGTTAAGAAAGTGAACAAAGCCACT

GAGGCCGCGATGTTCCTGGGCTGGGTGGAACAGCT

GGTATATGACTTCACGGACGAGACGAGCGAAGTG

AGCACTACCGACAAAATTGCTGATATTACCATCAT

TATCCCGTATATTGGTCCGGCACTGAACATTGGC

AACATGCTGTACAAAGACGATTTTGTGGGTGCCCT

GATCTTCTCCGGTGCCGTGATTCTGCTGGAGTTC

ATTCCGGAGATTGCGATCCCGGTGTTGGGTACCTT

CGCGCTGGTGTCCTACATCGCGAATAAGGTTCTG

ACGGTTCAGACCATCGATAACGCGCTGTCGAAACG

TAATGAAAAATGGGACGAGGTTTACAAATACATT

GTTACGAATTGGCTGGCGAAAGTCAATACCCAGAT

CGACCTGATCCGTAAGAAAATGAAAGAGGCGCTG

GAGAATCAGGCGGAGGCCACCAAAGCAATTATCAA

CTACCAATACAACCAGTACACGGAAGAAGAGAAG

AATAACATTAACTTCAATATCGATGATTTGAGCAG

CAAGCTGAATGAATCTATCAACAAAGCGATGATC

AATATCAACAAGTTTTTGAATCAGTGTAGCGTTTC

GTACCTGATGAATAGCATGATTCCGTATGGCGTC

AAACGTCTGGAGGACTTCGACGCCAGCCTGAAAGA

TGCGTTGCTGAAATACATTTACGACAATCGTGGT

ACGCTGATTGGCCAAGTTGACCGCTTGAAAGACAA

AGTTAACAATACCCTGAGCACCGACATCCCATTT

CAACTGAGCAAGTATGTTGATAATCAACGTCTGTT

GAGCACTTTCACCGAGTATATCAAAAACATCATC

AATACTAGCATTCTGAACCTGCGTTACGAGAGCAA

-continued
TCATCTGATTGATCTGAGCCGTTATGCAAGCAAG
ATCAACATCGGTAGCAAGGTCAATTTTGACCCGAT
CGATAAGAACCAGATCCAGCTGTTTAATCTGGAA
TCGAGCAAAATTGAGGTTATCCTGAAAAACGCCAT
TGTCTACAACTCCATGTACGAGAATTTCTCCACC
AGCTTCTGGATTCGCATCCCGAAATACTTCAACAG
CATTAGCCTGAACAACGAGTATACTATCATCAAC
TGTATGGAGAACAACAGCGGTTGGAAGGTGTCTCT
GAACTATGGTGAGATCATTTGGACCTTGCAGGAC
ACCCAAGAGATCAAGCAGCGCGTCGTGTTCAAGTA
CTCTCAAATGATCAACATTTCCGATTACATTAAT
CGTTGGATCTTCGTGACCATTACGAATAACCGTCT
GAATAACAGCAAGATTTACATCAATGGTCGCTTG
ATCGATCAGAAACCGATTAGCAACCTGGGTAATAT
CCACGCAAGCAACAACATTATGTTCAAATTGGAC
GGTTGCCGCGATACCCATCGTTATATCTGGATCAA
GTATTTCAACCTGTTTGATAAAGAACTGAATGAG
AAGGAGATCAAAGATTTGTATGACAACCAATCTAA
CAGCGGCATTTTGAAGGACTTCTGGGGCGATTAT
CTGCAATACGATAAGCCGTACTATATGCTGAACCT
GTATGATCCGAACAAATATGTGGATGTCAATAAT
GTGGGTATTCGTGGTTACATGTATTTGAAGGGTCC
GCGTGGCAGCGTTATGACGACCAACATTTACCTG
AACTCTAGCCTGTACCGTGGTACGAAATTCATCAT
TAAGAAATATGCCAGCGGCAACAAAGATAACATT
GTGCGTAATAACGATCGTGTCTACATCAACGTGGT
CGTGAAGAATAAAGAGTACCGTCTGGCGACCAAC
GCTTCGCAGGCGGGTGTTGAGAAAATTCTGAGCGC
GTTGGAGATCCCTGATGTCGGTAATCTGAGCCAA
GTCGTGGTTATGAAGAGCAAGAACGACCAGGGTAT
CACTAACAAGTGCAAGATGAACCTGCAAGACAAC
AATGGTAACGACATCGGCTTTATTGGTTTCCACCA
GTTCAACAATATTGCTAAACTGGTAGCGAGCAAT
TGGTACAATCGTCAGATTGAGCGCAGCAGCCGTAC
TTTGGGCTGTAGCTGGGAGTTTATCCCGGTCGAT
GATGGTTGGGGCGAACGTCCGCTG SEQ ID NO: 2. BoNT/A1 amino acid sequence.
MPFVNKQFNYKDPVNGVDIAYIKIPNAGQMQPVKA
FKIHNKIWVIPERDTFTNPEEGDLNPPPEAKQVP
VSYYDSTYLSTDNEKDNYLKGVTKLFERIYSTDLG
RMLLTSIVRGIPFWGGSTIDTELKVIDTNCINVI QPDGSYRSEELNLVIIGPSADIIQFECKSFGHEVL
NLTRNGYGSTQYIRFSPDFTFGFEESLEVDTNPL
LGAGKFATDPAVTLAHELIHAGHRLYGIAINPNRV
FKVNTNAYYEMSGLEVSFEELRTFGGHDAKFIDS
LQENEFRLYYYNKFKDIASTLNKAKSIVGTTASLQ
YMKNVFKEKYLLSEDTSGKFSVDKLKFDKLYKML
TEIYTEDNFVKFFKVLNRKTYLNFDKAVFKINIVP
KVNYTIYDGFNLRNTNLAANFNGQNTEINNMNFT
KLKNFTGLFEFYKLLCVRGIITSKTKSLDKGYNKA
LNDLCIKVNNWDLFFSPSEDNFTNDLNKGEEITS
DTNIEAAEENISLDLIQQYYLTFNFDNEPENISIE
NLSSDIIGQLELMPNIERFPNGKKYELDKYTMFH
YLRAQEFEHGKSRIALTNSVNEALLNPSRVYTFES
SDYVKKVNKATEAAMFLGWVEQLVYDFTDETSEV
STTDKIADITIIIPYIGPALNIGNMLYKDDFVGAL
IFSGAVILLEFIPEIAIPVLGTFALVSYIANKVL
TVQTIDNALSKRNEKWDEVYKYIVTNWLAKVNTQI
DLIRKKMKEALENQAEATKAIINYQYNQYTEEEK
NNINFNIDDLSSKLNESINKAMININKFLNQCSVS
YLMNSMIPYGVKRLEDFDASLKDALLKYIYDNRG
TLIGQVDRLKDKVNNTLSTDIPFQLSKYVDNQRLL
STFTEYIKNIINTSILNLRYESNHLIDLSRYASK
INTGSKVNFDPIDKNQIQLFNLESSKIEVILKNAI
VYNSMYENFSTSFWIRIPKYFNSISLNNEYTIIN
CMENNSGWKVSLNYGEIIWTLQDTQEIKQRVVFKY
SQMINISDYINRWIFVTITNNRLNNSKIYINGRL
IDQKPISNLGNIHASNNIMFKLDGCRDTHRYIWIK
YFNLFDKELNEKEIKDLYDNQSNSGILKDFWGDY
LQYDKPYYMLNLYDPNKYVDVNNVGIRGYMYLKGP
RGSVMTTNIYLNSSLYRGTKFIIKKYASGNKDNI
VRNNDRVYINVVVKNKEYRLATNASQAGVEKILSA
LEIPDVGNLSQVVVMKSKNDQGITNKCKMNLQDN
NGNDIGFIGFHQFNNIAKLVASNWYNRQIERSSRT
LGCSWEFIPVDDGWGERPL SEQ ID NO: 3. Engineered BoNT/A1 "Cat-A" nucleic acid sequence.
ATGCCATTCGTCAACAAGCAATTCAACTACAAAGA
CCCAGTCAACGGCGTCGACATCGCATACATCAAG
ATTCCGAACGCCGGTCAAATGCAGCCGGTTAAGGC
TTTTAAGATCCACAACAAGATTTGGGTTATCCCG
GAGCGTGACACCTTCACGAACCCGGAAGAAGGCGA
TCTGAACCCGCCACCGGAAGCGAAGCAAGTCCCT GTCAGCTACTACGATTCGACGTACCTGAGCACGGA
TAACGAAAAAGATAACTACCTGAAAGGTGTGACC
AAGCTGTTCGAACGTATCTACAGCACGGATCTGGG
TCGCATGCTGCTGACTAGCATTGTTCGCGGTATC
CCGTTCTGGGGTGGTAGCACGATTGACACCGAACT
GAAGGTTATCGACACTAACTGCATTAACGTTATT
CAACCGGATGGTAGCTATCGTAGCGAAGAGCTGAA
TCTGGTCATCATTGGCCCGAGCGCAGACATTATC
CAATTCGAGTGCAAGAGCTTTGGTCACGAGGTTCT
GAATCTGACCCGCAATGGCTATGGTAGCACCCAG
TACATTCGTTTTTCGCCGGATTTTACCTTCGGCTT
TGAAGAGAGCCTGGAGGTTGATACCAATCCGTTG
CTGGGTGCGGGCAAATTCGCTACCGATCCGGCTGT
CACGCTGGCCCATGAACTGATCCACGCAGGCCAC
CGCCTGTACGGCATTGCCATCAACCCAAACCGTGT
GTTCAAGGTTAATACGAATGCATACTACGAGATG
AGCGGCCTGGAAGTCAGCTTCGAAGAACTGCGCAC
CTTCGGTGGCCATGACGCTAAATTCATTGACAGC
TTGCAAGAGAATGAGTTCCGTCTGTACTACTATAA
CAAATTCAAAGACATTGCAAGCACGTTGAACAAG
GCCAAAAGCATCGTTGGTACTACCGCGTCGTTGCA
GTATATGAAGAATGTGTTTAAAGAGAAGTACCTG
CTGTCCGAGGATACCTCCGGCAAGTTTAGCGTTGA
TAAGCTGAAGTTTGACAAACTGTACAAGATGCTG
ACCGAGATTTACACCGAGGACAACTTTGTGAAATT
CTTCAAAGTGTTGAATCGTAAAACCTATCTGAAT
TTTGACAAAGCGGTTTTCAAGATTAACATCGTGCC
GAAGGTGAACTACACCATCTATGACGGTTTTAAC
CTGCGTAACACCAACCTGGCGGCGAACTTTAACGG
TCAGAATACGGAAATCAACAACATGAATTTCACG
AAGTTGAAGAACTTCACGGGTCTGTTCGAGTTCTA
TAAGCTGCTGTGCGTGCGCGGTATCATCACCAGC
AAAACCAAAAGCCTGGACAAAGGCTACAACAAGGC
GCTGAATGACCTGTGCATTAAGGTAAACAATTGG
GATCTGTTCTTTTCGCCATCCGAAGATAATTTTAC
CAACGACCTGAACAAGGGTGAAGAAATCACCAGC
GATACGAATATTGAAGCAGCGGAAGAGAATATCAG
CCTGGATCTGATCCAGCAGTACTATCTGACCTTT
AACTTCGACAATGAACCGGAGAACATTAGCATTGA
GAATCTGAGCAGCGACATTATCGGTCAGCTGGAA CTGATGCCGAATATCGAACGTTTCCCGAACGGCAA
AAAGTACGAGCTGGACAAGTACACTATGTTCCAT
TACCTGCGTGCACAGGAGTTTGAACACGGTAAAAG
CCGTATCGCGCTGACCAACAGCGTTAACGAGGCC
CTGCTGAACCCGAGCCGTGTCTATACCTTCTTCAG
CAGCGACTATGTTAAGAAAGTGAACAAAGCCACT
GAGGCCGCGATGTTCCTGGGCTGGGTGGAACAGCT
GGTATATGACTTCACGGACGAGACGAGCGAAGTG
AGCACTACCGACAAAATTGCTGATATTACCATCAT
TATCCCGTATATTGGTCCGGCACTGAACATTGGC
AACATGCTGTACAAAGACGATTTTGTGGGTGCCCT
GATCTTCTCCGGTGCCGTGATTCTGCTGGAGTTC
ATTCCGGAGATTGCGATCCCGGTGTTGGGTACCTT
CGCGCTGGTGTCCTACATCGCGAATAAGGTTCTG
ACGGTTCAGACCATCGATAACGCGCTGTCGAAACG
TAATGAAAAATGGGACGAGGTTTACAAATACATT
GTTACGAATTGGCTGGCGAAAGTCAATACCCAGAT
CGACCTGATCCGTAAGAAAATGAAAGAGGCGCTG
GAGAATCAGGCGGAGGCCACCAAAGCAATTATCAA
CTACCAATACAACCAGTACACGGAAGAAGAGAAG
AATAACATTAACTTCAATATCGATGATTTGAGCAG
CAAGCTGAATGAATCTATCAACAAAGCGATGATC
AATATCAACAAGTTTTTGAATCAGTGTAGCGTTTC
GTACCTGATGAATAGCATGATTCCGTATGGCGTC
AAACGTCTGGAGGACTTCGACGCCAGCCTGAAAGA
TGCGTTGCTGAAATACATTTACGACAATCGTGGT
ACGCTGATTGGCCAAGTTGACCGCTTGAAAGACAA
AGTTAACAATACCCTGAGCACCGACATCCCATTT
CAACTGAGCAAGTATGTTGATAATCAACGTCTGTT
GAGCACTTTCACCGAGTATATCAAAAACATCATC
AATACTAGCATTCTGAACCTGCGTTACGAGAGCAA
GCATCTGATTGATCTGAGCCGTTATGCTAGCAAG
ATCAACATCGGTAGCAAGGTCAATTTTGACCCGAT
CGATAAGAACCAGATCCAGCTGTTTAATCTGGAA
TCGAGCAAAATTGAGGTTATCCTGAAAAAGGCCAT
TGTCTACAACTCCATGTACGAGAATTTCTCCACC
AGCTTCTGGATTCGCATCCCGAAATACTTCAACAA
GATTAGCCTGAACAACGAGTATACTATCATCAAC
TGTATGGAGAACAACAGCGGTTGGAAGGTGTCTCT
GAACTATGGTGAGATCATTTGGACCTTGCAGGAC
ACCAAAGAGATCAAGCAGCGCGTCGTGTTCAAGTA -continued
CTCTCAAATGATCAACATTTCCGATTACATTAAT
CGTTGGATCTTCGTGACCATTACGAATAACCGTCT
GAATAAGAGCAAGATTTACATCAATGGTCGCTTG
ATCGATCAGAAACCGATTAGCAACCTGGGTAATAT
CCACGCAAGCAACAAGATTATGTTCAAATTGGAC
GGTTGCCGCGATACCCATCGTTATATCTGGATCAA
GTATTTCAACCTGTTTGATAAAGAACTGAATGAG
AAGGAGATCAAAGATTTGTATGACAACCAATCTAA
CAGCGGCATTTTGAAGGACTTCTGGGGCGATTAT
CTGCAATACGATAAGCCGTACTATATGCTGAACCT
GTATGATCCGAACAAATATGTGGATGTCAATAAT
GTGGGTATTCGTGGTTACATGTATTTGAAGGGTCC
GCGTGGCAGCGTTATGACGACCAACATTTACCTG
AACTCTAGCCTGTACCGTGGTACGAAATTCATCAT
TAAGAAATATGCCAGCGGCAACAAAGATAACATT
GTGCGTAATAACGATCGTGTCTACATCAACGTGGT
CGTGAAGAATAAAGAGTACCGTCTGGCGACCAAC
GCTTCGCAGGCGGGTGTTGAGAAAATTCTGAGCGC
GTTGGAGATCCCTGATGTCGGTAATCTGAGCCAA
GTCGTGGTTATGAAGAGCAAGAACGACAAGGGTAT
CACTAACAAGTGCAAGATGAACCTGCAAGACAAC
AATGGTAACGACATCGGCTTTATTGGTTTCCACCA
GTTCAACAATATTGCTAAACTGGTAGCGAGCAAT
TGGTACAATCGTCAGATTGAGCGCAGCAGCcGTAC
TTTGGGCTGTAGCTGGGAGTTTATCCCGGTCGAT
GATGGTTGGGGCGAACGTCCGCTG SEQ ID NO: 4. Engineered BoNT/A1 "Cat-A" amino acid sequence.
MPFVNKQFNYKDPVNGVDIAYIKIPNAGQMQPVKA
FKIHNKIWVIPERDTFTNPEEGDLNPPPEAKQVP
VSYYDSTYLSTDNEKDNYLKGVTKLFERIYSTDLG
RMLLTSIVRGIPFWGGSTIDTELKVIDTNCINVI
QPDGSYRSEELNLVIIGPSADITQFECKSFGHEVL
NLTRNGYGSTQYIRFSPDFTEGFEESLEVDTNPL
LGAGKFATDPAVTLAHELIHAGHRLYGIAINPNRV
FKVNTNAYYEMSGLEVSFEELRTFGGHDAKFIDS
LQENEFRLYYYNKFKDIASTLNKAKSIVGTTASLQ
YMKNVFKEKYLLSEDTSGKESVDKLKEDKLYKML
TEIYTEDNEVKFEKVLNRKTYLNEDKAVFKINIVP
KVNYTIYDGENLRNTNLAANENGQNTEINNMNFT
KLKNFTGLFEFYKLLCVRGIITSKTKSLDKGYNKA LNDLCIKVNNWDLFESPSEDNFTNDLNKGEEITS
DTNIEAAEENISLDLIQQYYLTFNEDNEPENISIE
NLSSDIIGQLELMPNIERFPNGKKYELDKYTMFH
YLRAQEFEHGKSRIALTNSVNEALLNPSRVYTFES
SDYVKKVNKATEAAMFLGWVEQLVYDFTDETSEV
STTDKIADITIIIPYIGPALNIGNMLYKDDFVGAL
IFSGAVILLEFIPEIAIPVLGTFALVSYIANKVL
TVQTIDNALSKRNEKWDEVYKYIVTNWLAKVNTQI
DLIRKKMKEALENQAEATKAIINYQYNQYTEEEK
NNINFNIDDLSSKLNESINKAMININKFLNQCSVS
YLMNSMIPYGVKRLEDFDASLKDALLKYIYDNRG
TLIGQVDRLKDKVNNTLSTDIPFQLSKYVDNQRLL
STFTEYIKNIINTSILNLRYESKHLIDLSRYASK
INTGSKVNFDPIDKNQIQLFNLESSKIEVILKKAI
VYNSMYENFSTSFWIRIPKYFNKISLNNEYTIIN
CMENNSGWKVSLNYGEIIWTLQDTKEIKQRVVFKY
SQMINISDYINRWIFVTITNNRLNKSKIYINGRL
IDQKPISNLGNIHASNKIMFKLDGCRDTHRYIWIK
YFNLFDKELNEKEIKDLYDNQSNSGILKDFWGDY
LQYDKPYYMLNLYDPNKYVDVNNVGIRGYMYLKGP
RGSVMTTNIYLNSSLYRGTKFIIKKYASGNKDNI
VRNNDRVYINVVVKNKEYRLATNASQAGVEKILSA
LEIPDVGNLSQVVVMKSKNDKGITNKCKMNLQDN
NGNDIGFIGFHQFNNIAKLVASNWYNRQIERSSRT
LGCSWEETPVDDGWGERPL SEQ ID NO: 5. Engineered BoNT/A1 "Cat-B" nucleic acid sequence.
ATGCCATTCGTCAACAAGCAATTCAACTACAAAGA
CCCAGTCAACGGCGTCGACATCGCATACATCAAG
ATTCCGAACGCCGGTCAAATGCAGCCGGTTAAGGC
TTTTAAGATCCACAACAAGATTTGGGTTATCCCG
GAGCGTGACACCTTCACGAACCCGGAAGAAGGCGA
TCTGAACCCGCCACCGGAAGCGAAGCAAGTCCCT
GTCAGCTACTACGATTCGACGTACCTGAGCACGGA
TAACGAAAAGATAACTACCTGAAAGGTGTGACC
AAGCTGTTCGAACGTATCTACAGCACGGATCTGGG
TCGCATGCTGCTGACTAGCATTGTTCGCGGTATC
CCGTTCTGGGGTGGTAGCACGATTGACACCGAACT
GAAGGTTATCGACACTAACTGCATTAACGTTATT
CAACCGGATGGTAGCTATCGTAGCGAAGAGCTGAA
TCTGGTCATCATTGGCCCGAGCGCAGACATTATC
CAATTCGAGTGCAAGAGCTTTGGTCACGAGGTTCT

```
GAATCTGACCCGCAATGGCTATGGTAGCACCCAG

TACATTCGTTTTTCGCCGGATTTTACCTTCGGCTT

TGAAGAGAGCCTGGAGGTTGATACCAATCCGTTG

CTGGGTGCGGGCAAATTCGCTACCGATCCGGCTGT

CACGCTGGCCCATGAACTGATCCACGCAGGCCAC

CGCCTGTACGGCATTGCCATCAACCCAAACCGTGT

GTTCAAGGTTAATACGAATGCATACTACGAGATG

AGCGGCCTGGAAGTCAGCTTCGAAGAACTGCGCAC

CTTCGGTGGCCATGACGCTAAATTCATTGACAGC

TTGCAAGAGAATGAGTTCCGTCTGTACTACTATAA

CAAATTCAAAGACATTGCAAGCACGTTGAACAAG

GCCAAAAGCATCGTTGGTACTACCGCGTCGTTGCA

GTATATGAAGAATGTGTTTAAAGAGAAGTACCTG

CTGTCCGAGGATACCTCCGGCAAGTTTAGCGTTGA

TAAGCTGAAGTTTGACAAACTGTACaAGATGCTG

ACCGAGATTTACACCGAGGACAACTTTGTGAAATT

CTTCAAAGTGTTGAATCGTAAAACCTATCTGAAT

TTTGACAAAGCGGTTTTCAAGATTAACATCGTGCC

GAAGGTGAACTACACCATCTATGACGGTTTTAAC

CTGCGTAACACCAACCTGGCGGCGAACTTTAACGG

TCAGAATACGGAAATCAACAACATGAATTTCACG

AAGTTGAAGAACTTCACGGGTCTGTTCGAGTTCTA

TAAGCTGCTGTGCGTGCGCGGTATCATCACCAGC

AAAACCAAAAGCCTGGACAAAGGCTACAACAAGGC

GCTGAATGACCTGTGCATTAAGGTAAACAATTGG

GATCTGTTCTTTTCGCCATCCGAAGATAATTTTAC

CAACGACCTGAACAAGGGTGAAGAAATCACCAGC

GATACGAATATTGAAGCAGCGGAAGAGAATATCAG

CCTGGATCTGATCCAGCAGTACTATCTGACCTTT

AACTTCGACAATGAACCGGAGAACATTAGCATTGA

GAATCTGAGCAGCGACATTATCGGTCAGCTGGAA

CTGATGCCGAATATCGAACGTTTCCCGAACGGCAA

AAAGTACGAGCTGGACAAGTACACTATGTTCCAT

TACCTGCGTGCACAGGAGTTTGAACACGGTAAAAG

CCGTATCGCGCTGACCAACAGCGTTAACGAGGCC

CTGCTGAACCCGAGCCGTGTCTATACCTTCTTCAG

CAGCGACTATGTTAAGAAAGTGAACAAAGCCACT

GAGGCCGCGATGTTCCTGGGCTGGGTGGAACAGCT

GGTATATGACTTCACGGACGAGACGAGCGAAGTG

AGCACTACCGACAAAATTGCTGATATTACCATCAT

TATCCCGTATATTGGTCCGGCACTGAACATTGGC

AACATGCTGTACAAAGACGATTTTGTGGGTGCCCT

GATCTTCTCCGGTGCCGTGATTCTGCTGGAGTTC

ATTCCGGAGATTGCGATCCCGGTGTTGGGTACCTT

CGCGCTGGTGTCCTACATCGCGAATAAGGTTCTG

ACGGTTCAGACCATCGATAACGCGCTGTCGAAACG

TAATGAAAAATGGGACGAGGTTTACAAATACATT

GTTACGAATTGGCTGGCGAAAGTCAATACCCAGAT

CGACCTGATCCGTAAGAAAATGAAAGAGGCGCTG

GAGAATCAGGCGGAGGCCACCAAAGCAATTATCAA

CTACCAATACAACCAGTACACGGAAGAAGAGAAG

AATAACATTAACTTCAATATCGATGATTTGAGCAG

CAAGCTGAATGAATCTATCAACAAAGCGATGATC

AATATCAACAAGTTTTTTGAATCAGTGTAGCGTTTC

GTACCTGATGAATAGCATGATTCCGTATGGCGTC

AAACGTCTGGAGGACTTCGACGCCAGCCTGAAAGA

TGCGTTGCTGAAATACATTTACGACAaTCGTGGT

ACGCTGATTGGCCAAGTTGACCGCTTGAAAGACAA

AGTTAACAATACCCTGAGCACCGACATCCCATTT

CAACTGAGCAAGTATGTTGATAATCAACGTCTGTT

GAGCACTTTCACCGAGTATATCAAAAACATCATC

AATACTAGCATTCTGAACCTGCGTTACGAGAGCAA

TCATCTGATTGATCTGAGCCGTTATGCTAGCAAG

ATCAACATCGGTAGCAAGGTCAATTTTGACCCGAT

CGATAAGAACCAGATCCAGCTGTTTAATCTGGAA

TCGAGCAAAATTGAGGTTATCCTGAAAAAGGCCAT

TGTCTACAACTCCATGTACGAGAATTTCTCCACC

AGCTTCTGGATTCGCATCCCGAAATACTTCAAGAA

GATTAGCCTGAACAACGAGTATACTATCATCAAC

TGTATGGAGAACAACAGCGGTTGGAAGGTGTCTCT

GAACTATGGTGAGATCATTTGGACCTTGCAGGAC

ACCAAAGAGATCAAGCAGCGCGTCGTGTTCAAGTA

CTCTCAAATGATCAACATTTCCGATTACATTAAT

CGTTGGATCTTCGTGACCATTACGAATAACCGTCT

GAATAAGAGCAAGATTTACATCAATGGTCGCTTG

ATCGATCAGAAACCGATTAGCAACCTGGGTAATAT

CCACGCAAGCAACAAGATTATGTTCAAATTGGAC

GGTTGCCGCGATACCCATCGTTATATCTGGATCAA

GTATTTCAACCTGTTTGATAAAGAACTGAATGAG

AAGGAGATCAAAGATTTGTATGACAACCAATCTAA

CAGCGGCATTTTGAAGGACTTCTGGGGCGATTAT
```

-continued

CTGCAATACGATAAGCCGTACTATATGCTGAACCT

GTATGATCCGAACAAATATGTGGATGTCAATAAT

GTGGGTATTCGTGGTTACATGTATTTGAAGGGTCC

GCGTGGCAGCGTTATGACGACCAACATTTACCTG

AACTCTAGCCTGTACCGTGGTACGAAATTCATCAT

TAAGAAATATGCCAGCGGCAACAAAGATAACATT

GTGCGTAATAACGATCGTGTCTACATCAACGTGGT

CGTGAAGAATAAAGAGTACCGTCTGGCGACCAAC

GCTTCGCAGGCGGGTGTTGAGAAAATTCTGAGCGC

GTTGGAGATCCCTGATGTCGGTAATCTGAGCCAA

GTCGTGGTTATGAAGAGCAAGAACGACAAGGGTAT

CACTAACAAGTGCAAGATGAACCTGCAAGACAAC

AATGGTAACGACATCGGCTTTATTGGTTTCCACCA

GTTCAACAATATTGCTAAACTGGTAGCGAGCAAT

TGGTACAATCGTCAGATTGAGCGCAGCAGCCGTAC

TTTGGGCTGTAGCTGGGAGTTTATCCCGGTCGAT

GATGGTTGGGGCGAACGTCCGCTG

SEQ ID NO: 6. Engineered BoNT/A1 "Cat-B" amino acid sequence.

MPFVNKQFNYKDPVNGVDIAYIKIPNAGQMQPVKA

FKIHNKIWVIPERDTFTNPEEGDLNPPPEAKQVP

VSYYDSTYLSTDNEKDNYLKGVTKLFERIYSTDLG

RMLLTSIVRGIPFWGGSTIDTELKVIDTNCINVI

QPDGSYRSEELNLVIIGPSADITQFECKSFGHEVL

NLTRNGYGSTQYIRFSPDFTEGFEESLEVDTNPL

LGAGKFATDPAVTLAHELIHAGHRLYGIAINPNRV

FKVNTNAYYEMSGLEVSFEELRTFGGHDAKFIDS

LQENEFRLYYYNKFKDIASTLNKAKSIVGTTASLQ

YMKNVFKEKYLLSEDTSGKESVDKLKEDKLYKML

TETYTEDNEVKFFKVLNRKTYLNEDKAVFKINIVP

KVNYTIYDGENLRNTNLAANENGQNTEINNMNFT

KLKNFTGLFEFYKLLCVRGIITSKTKSLDKGYNKA

LNDLCIKVNNWDLFFSPSEDNFTNDLNKGEEITS

DTNIEAAEENISLDLIQQYYLTFNEDNEPENISIE

NLSSDIIGQLELMPNIERFPNGKKYELDKYTMFH

YLRAQEFEHGKSRIALTNSVNEALLNPSRVYTFES

SDYVKKVNKATEAAMFLGWVEQLVYDFTDETSEV

STTDKIADITIIIPYIGPALNIGNMLYKDDFVGAL

IFSGAVILLEFIPEIAIPVLGTFALVSYIANKVL

TVQTIDNALSKRNEKWDEVYKYIVTNWLAKVNTQI

DLIRKKMKEALENQAEATKAIINYQYNQYTEEEK

-continued

NNINFNIDDLSSKLNESINKAMININKFLNQCSVS

YLMNSMIPYGVKRLEDFDASLKDALLKYIYDNRG

TLIGQVDRLKDKVNNTLSTDIPFQLSKYVDNQRLL

STFTEYIKNIINTSILNLRYESNHLIDLSRYASK

INTGSKVNFDPIDKNQIQLFNLESSKIEVILKKAI

VYNSMYENFSTSFWIRIPKYFKKISLNNEYTIIN

CMENNSGWKVSLNYGEIIWTLQDTKEIKQRVVFKY

SQMINISDYINRWIFVTITNNRLNKSKIYINGRL

IDQKPISNLGNIHASNKIMFKLDGCRDTHRYIWIK

YFNLFDKELNEKEIKDLYDNQSNSGILKDFWGDY

LQYDKPYYMLNLYDPNKYVDVNNVGIRGYMYLKGP

RGSVMTTNIYLNSSLYRGTKFIIKKYASGNKDNI

VRNNDRVYINVVVKNKEYRLATNASQAGVEKILSA

LEIPDVGNLSQVVVMKSKNDKGITNKCKMNLQDN

NGNDIGFIGFHQFNNIAKLVASNWYNRQIERSSRT

LGCSWEFIPVDDGWGERPL

SEQ ID NO: 7. Engineered BoNT/A1 "Cat-C" nucleic acid sequence.

ATGCCATTCGTCAACAAGCAATTCAACTACAAAGA

CCCAGTCAACGGCGTCGACATCGCATACATCAAG

ATTCCGAACGCCGGTCAAATGCAGCCGGTTAAGGC

TTTTAAGATCCACAACAAGATTTGGGTTATCCCG

GAGCGTGACACCTTCACGAACCCGGAAGAAGGCGA

TCTGAACCCGCCACCGGAAGCGAAGCAAGTCCCT

GTCAGCTACTACGATTCGACGTACCTGAGCACGGA

TAACGAAAAAGATAACTACCTGAAAGGTGTGACC

AAGCTGTTCGAACGTATCTACAGCACGGATCTGGG

TCGCATGCTGCTGACTAGCATTGTTCGCGGTATC

CCGTTCTGGGGTGGTAGCACGATTGACACCGAACT

GAAGGTTATCGACACTAACTGCATTAACGTTATT

CAACCGGATGGTAGCTATCGTAGCGAAGAGCTGAA

TCTGGTCATCATTGGCCCGAGCGCAGACATTATC

CAATTCGAGTGCAAGAGCTTTGGTCACGAGGTTCT

GAATCTGACCCGCAATGGCTATGGTAGCACCCAG

TACATTCGTTTTTCGCCGGATTTTACCTTCGGCTT

TGAAGAGAGCCTGGAGGTTGATACCAATCCGTTG

CTGGGTGCGGGCAAATTCGCTACCGATCCGGCTGT

CACGCTGGCCCATGAACTGATCCACGCAGGCCAC

CGCCTGTACGGCATTGCCATCAACCCAAACCGTGT

GTTCAAGGTTAATACGAATGCATACTACGAGATG

AGCGGCCTGGAAGTCAGCTTCGAAGAACTGCGCAC

CTTCGGTGGCCATGACGCTAAATTCATTGACAGC

TTGCAAGAGAATGAGTTCCGTCTGTACTACTATAA
CAAATTCAAAGACATTGCAAGCACGTTGAACAAG
GCCAAAAGCATCGTTGGTACTACCGCGTCGTTGCA
GTATATGAAGAATGTGTTTAAAGAGAAGTACCTG
CTGTCCGAGGATACCTCCGGCAAGTTTAGCGTTGA
TAAGCTGAAGTTTGACAAACTGTACAAGATGCTG
ACCGAGATTTACACCGAGGACAACTTTGTGAAATT
CTTCAAAGTGTTGAATCGTAAAACCTATCTGAAT
TTTGACAAAGCGGTTTTCAAGATTAACATCGTGCC
GAAGGTGAACTACACCATCTATGACGGTTTTAAC
CTGCGTAACACCAACCTGGCGGCGAACTTTAACGG
TCAGAATACGGAAATCAACAACATGAATTTCACG
AAGTTGAAGAACTTCACGGGTCTGTTCGAGTTCTA
TAAGCTGCTGTGCGTGCGCGGTATCATCACCAGC
AAAACCAAAAGCCTGGACAAAGGCTACAACAAGGC
GCTGAATGACCTGTGCATTAAGGTAAACAATTGG
GATCTGTTCTTTTCGCCATCCGAAGATAATTTTAC
CAACGACCTGAACAAGGGTGAAGAAATCACCAGC
GATACGAATATTGAAGCAGCGGAAGAGAATATCAG
CCTGGATCTGATCCAGCAGTACTATCTGACCTTT
AACTTCGACAATGAACCGGAGAACATTAGCATTGA
GAATCTGAGCAGCGACATTATCGGTCAGCTGGAA
CTGATGCCGAATATCGAACGTTTCCCGAACGGCAA
AAAGTACGAGCTGGACAAGTACACTATGTTCCAT
TACCTGCGTGCACAGGAGTTTGAACACGGTAAAAG
CCGTATCGCGCTGACCAACAGCGTTAACGAGGCC
CTGCTGAACCCGAGCCGTGTCTATACCTTCTTCAG
CAGCGACTATGTTAAGAAAGTGAACAAAGCCACT
GAGGCCGCGATGTTCCTGGGCTGGGTGGAACAGCT
GGTATATGACTTCACGGACGAGACGAGCGAAGTG
AGCACTACCGACAAAATTGCTGATATTACCATCAT
TATCCCGTATATTGGTCCGGCACTGAACATTGGC
AACATGCTGTACAAAGACGATTTTGTGGGTGCCCT
GATCTTCTCCGGTGCCGTGATTCTGCTGGAGTTC
ATTCCGGAGATTGCGATCCCGGTGTTGGGTACCTT
CGCGCTGGTGTCCTACATCGCGAATAAGGTTCTG
ACGGTTCAGACCATCGATAACGCGCTGTCGAAACG
TAATGAAAAATGGGACGAGGTTTACAAATACATT
GTTACGAATTGGCTGGCGAAAGTCAATACCCAGAT
CGACCTGATCCGTAAGAAAATGAAAGAGGCGCTG GAGAATCAGGCGGAGGCCACCAAAGCAATTATCAA
CTACCAATACAACCAGTACACGGAAGAAGAGAAG
AATAACATTAACTTCAATATCGATGATTTGAGCAG
CAAGCTGAATGAATCTATCAACAAAGCGATGATC
AATATCAACAAGTTTTTGAATCAGTGTAGCGTTTC
GTACCTGATGAATAGCATGATTCCGTATGGCGTC
AAACGTCTGGAGGACTTCGACGCCAGCCTGAAAGA
TGCGTTGCTGAAATACATTTACGACAATCGTGGT
ACGCTGATTGGCCAAGTTGACCGCTTGAAAGACAA
AGTTAACAATACCCTGAGCACCGACATCCCATTT
CAACTGAGCAAGTATGTTGATAATCAACGTCTGTT
GAGCACTTTCACCGAGTATATCAAAAACATCATC
AATACTAGCATTCTGAACCTGCGTTACGAGAGCAA
TCATCTGATTGATCTGAGCCGTTATGCTAGCAAG
ATCAACATCGGTAGCAAGGTCAATTTTGACCCGAT
CGATAAGAACCAGATCCAGCTGTTTAATCTGGAA
TCGAGCAAAATTGAGGTTATCCTGAAAAAGGCCAT
TGTCTACAACTCCATGTACGAGAATTTCTCCACC
AGCTTCTGGATTCGCATCCCGAAATACTTCAACAA
GATTAGCCTGAACAACGAGTATACTATCATCAAC
TGTATGGAGAACAACAGCGGTTGGAAGGTGTCTCT
GAACTATGGTGAGATCATTTGGACCTTGCAGGAC
ACCAAAGAGATCAAGCAGCGCGTCGTGTTCAAGTA
CTCTCAAATGATCAACATTTCCGATTACATTAAT
CGTTGGATCTTCGTGACCATTACGAATAACCGTCT
GAAGAAGAGCAAGATTTACATCAATGGTCGCTTG
ATCGATCAGAAACCGATTAGCAACCTGGGTAATAT
CCACGCAAGCAACAAGATTATGTTCAAATTGGAC
GGTTGCCGCGATACCCATCGTTATATCTGGATCAA
GTATTTCAACCTGTTTGATAAAGAACTGAATGAG
AAGGAGATCAAAGATTTGTATGACAACCAATCTAA
CAGCGGCATTTTGAAGGACTTCTGGGGCGATTAT
CTGCAATACGATAAGCCGTACTATATGCTGAACCT
GTATGATCCGAACAAATATGTGGATGTCAATAAT
GTGGGTATTCGTGGTTACATGTATTTGAAGGGTCC
GCGTGGCAGCGTTATGACGACCAACATTTACCTG
AACTCTAGCCTGTACCGTGGTACGAAATTCATCAT
TAAGAAATATGCCAGCGGCAACAAAGATAACATT
GTGCGTAATAACGATCGTGTCTACATCAACGTGGT
CGTGAAGAATAAAGAGTACCGTCTGGCGACCAAC
GCTTCGCAGGCGGGTGTTGAGAAAATTCTGAGCGC

```
GTTGGAGATCCCTGATGTCGGTAATCTGAGCCAA

GTCGTGGTTATGAAGAGCAAGAACGACAAGGGTAT

CACTAACAAGTGCAAGATGAACCTGCAAGACAAC

AATGGTAACGACATCGGCTTTATTGGTTTCCACCA

GTTCAACAATATTGCTAAACTGGTAGCGAGCAAT

TGGTACAATCGTCAGATTGAGCGCAGCAGCCGTAC

TTTGGGCTGTAGCTGGGAGTTTATCCCGGTCGAT

GATGGTTGGGGCGAACGTCCGCTG
```

SEQ ID NO: 8. Engineered BoNT/A1 "Cat-C" amino acid sequence.
```
MPFVNKQFNYKDPVNGVDIAYIKIPNAGQMQPVKA

FKIHNKIWVIPERDTFTNPEEGDLNPPPEAKQVP

VSYYDSTYLSTDNEKDNYLKGVTKLFERIYSTDLG

RMLLTSIVRGIPFWGGSTIDTELKVIDTNCINVI

QPDGSYRSEELNLVIIGPSADIIQFECKSFGHEVL

NLTRNGYGSTQYIRFSPDFTFGFEESLEVDTNPL

LGAGKFATDPAVTLAHELIHAGHRLYGIAINPNRV

FKVNTNAYYEMSGLEVSFEELRTFGGHDAKFIDS

LQENEFRLYYYNKFKDIASTLNKAKSIVGTTASLQ

YMKNVFKEKYLLSEDTSGKESVDKLKEDKLYKML

TEIYTEDNEVKFEKVLNRKTYLNEDKAVFKINIVP

KVNYTIYDGENLRNTNLAANENGQNTEINNMNFT

KLKNFTGLFEFYKLLCVRGIITSKTKSLDKGYNKA

LNDLCIKVNNWDLFESPSEDNFTNDLNKGEEITS

DTNIEAAEENISLDLIQQYYLTFNEDNEPENISIE

NLSSDIIGQLELMPNIERFPNGKKYELDKYTMFH

YLRAQEFEHGKSRIALTNSVNEALLNPSRVYTFES

SDYVKKVNKATEAAMFLGWVEQLVYDFTDETSEV

STTDKIADITIIIPYIGPALNIGNMLYKDDFVGAL

IFSGAVILLEFIPEIAIPVLGTFALVSYIANKVL

TVQTIDNALSKRNEKWDEVYKYIVTNWLAKVNTQI

DLIRKKMKEALENQAEATKAIINYQYNQYTEEEK

NNINFNIDDLSSKLNESINKAMININKFLNQCSVS

YLMNSMIPYGVKRLEDFDASLKDALLKYIYDNRG

TLIGQVDRLKDKVNNTLSTDIPFQLSKYVDNQRLL

STFTEYIKNIINTSILNLRYESNHLIDLSRYASK

INTGSKVNFDPIDKNQIQLFNLESSKIEVILKKAI

VYNSMYENFSTSFWIRIPKYFNKISLNNEYTIIN

CMENNSGWKVSLNYGEIIWTLQDTKEIKQRVVFKY

SQMINISDYINRWIFVTITNNRLKKSKIYINGRL

IDQKPISNLGNIHASNKIMFKLDGCRDTHRYIWIK

YFNLFDKELNEKEIKDLYDNQSNSGILKDFWGDY

LQYDKPYYMLNLYDPNKYVDVNNVGIRGYMYLKGP

RGSVMTTNIYLNSSLYRGTKFIIKKYASGNKDNI

VRNNDRVYINVVVKNKEYRLATNASQAGVEKILSA

LEIPDVGNLSQVVVMKSKNDKGITNKCKMNLQDN

NGNDIGFIGFHQFNNIAKLVASNWYNRQIERSSR

TLGCSWEETPVDDGWGERPL
```

SEQ ID NO: 9. Engineered BoNT/A1 "Cat-D" nucleic acid sequence.
```
ATGCCATTCGTCAACAAGCAATTCAACTACAAAGA

CCCAGTCAACGGCGTCGACATCGCATACATCAAG

ATTCCGAACGCCGGTCAAATGCAGCCGGTTAAGGC

TTTTAAGATCCACAACAAGATTTGGGTTATCCCG

GAGCGTGACACCTTCACGAACCCGGAAGAAGGCGA

TCTGAACCCGCCACCGGAAGCGAAGCAAGTCCCT

GTCAGCTACTACGATTCGACGTACCTGAGCACGGA

TAACGAAAAAGATAACTACCTGAAAGGTGTGACC

AAGCTGTTCGAACGTATCTACAGCACGGATCTGGG

TCGCATGCTGCTGACTAGCATTGTTCGCGGTATC

CCGTTCTGGGGTGGTAGCACGATTGACACCGAACT

GAAGGTTATCGACACTAACTGCATTAACGTTATT

CAACCGGATGGTAGCTATCGTAGCGAAGAGCTGAA

TCTGGTCATCATTGGCCCGAGCGCAGACATTATC

CAATTCGAGTGCAAGAGCTTTGGTCACGAGGTTCT

GAATCTGACCCGCAATGGCTATGGTAGCACCCAG

TACATTCGTTTTTCGCCGGATTTTACCTTCGGCTT

TGAAGAGAGCCTGGAGGTTGATACCAATCCGTTG

CTGGGTGCGGGCAAATTCGCTACCGATCCGGCTGT

CACGCTGGCCCATGAACTGATCCACGCAGGCCAC

CGCCTGTACGGCATTGCCATCAACCCAAACCGTGT

GTTCAAGGTTAATACGAATGCATACTACGAGATG

AGCGGCCTgGAAGTCAGCTTCGAAGAACTGCGCAC

CTTCGGTGGCCATGACGCTAAATTCATTGACAGC

TTGCAAGAGAATGAGTTCCGTCTGTACTACTATAA

CAAATTCAAAGACATTGCAAGCACGTTGAACAAG

GCCAAAAGCATCGTTGGTACTACCGCGTCGTTGCA

GTATATGAAGAATGTGTTTAAAGAGAAGTACCTG

CTGTCCGAGGATACCTCCGGCAAGTTTAGCGTTGA
```

-continued
```
TAAGCTGAAGTTTGACAAACTGTACAAGATGCTG
ACCGAGATTTACACCGAGGACAACTTTGTGAAATT
CTTCAAaGTGTTGAATCGTAAAACCTATCTGAAT
TTTGACAAAGCGGTTTTCaAGATTAACATCGTGCC
GAAGGTGAACTACACCATCTATGACGGTTTTAAC
CTGCGTAACACCAACCTGGCGGCGAACTTTAACGG
TCAGAATACGGAAATCAACAACATGAATTTCACG
AAGTTGAAGAACTTCACGGGTCTGTTCGAGTTCTA
TAAGCTGCTGTGCGTGCGCGGTATCATCACCAGC
AAAACCAAAAGCCTGGACAAAGGCTACAACAAGGC
GCTGAATGACCTGTGCATTAAGGTAAACAATTGG
GATCTGTTCTTTTCGCCATCCGAAGATAATTTTAC
CAACGACCTGAACAAGGGTGAAGAAATCACCAGC
GATACGAATATTGAAGCAGCGGAAGAGAATATCAG
CCTGGATCTGATCCAGCAGTACTATCTGACCTTT
AACTTCGACAATGAACCGGAGAACATTAGCATTGA
GAATCTGAGCAGCGACATTATCGGTCAGCTGGAA
CTGATGCCGAATATCGAACGTTTCCCGAACGGCAA
AAAGTACGAGCTGGACAAGTACACTATGTTCCAT
TACCTGCGTGCACAGGAGTTTGAACACGGTAAAAG
CCGTATCGCGCTGACCAACAGCGTTAACGAGGCC
CTGCTGAACCCGAGCCGTGTCTATACCTTCTTCAG
CAGCGACTATGTTAAGAAAGTGAACAAAGCCACT
GAGGCCGCGATGTTCCTGGGCTGGTGGAACAGCT
GGTATATGACTTCACGGACGAGACGAGCGAAGTG
AGCACTACCGACAAAaTTGCTGATaTTACCATCAT
TATCCCGTATATTGGTCCGGCACTGAACATTGGC
AACATGCTGTACAAAGACGATTTTGTGGGTGCCCT
GATCTTCTCCGGTGCCGTGATTCTGCTGGAGTTC
ATTCCGGAGATTGCGATCCCGGTGTTGGGTACCTT
CGCGCTGGTGTCCTACATCGCGAATAAGGTTCTG
ACGGTTCAGACCATCGATAACGCGCTGTCGAAACG
TAATGAAAAATGGGACGAGGTTTACAAATACATT
GTTACGAATTGGCTGGCGAAAGTCaATACCCAGAT
CGACCTGATCCGTAAGAAAATGAAAGAGGCGCTG
GAGAATCAGGCGGAGGCCACCAAAGCAATTATCAA
CTACCAATACAACCAGTACACGGAAGAAGAGAAG
AATAACATTAACTTCAATATCGATGATTTGAGCAG
CAAGCTGAATGAATCTATCAACAAAGCGATGATC
```

-continued
```
AATATCAACAAGTTTTTGAATCAGTGTAGCGTTTC
GTACCTGATGAATAGCATGATTCCGTATGGCGTC
AAACGTCTGGAGGACTTCGACGCCAGCCTGAAAGA
TGCGTTGCTGAAATACATTTACGACAATCGTGGT
ACGCTGATTGGCCAAGTTGACCGCTTGAAAGACAA
AGTTAACAATACCCTGAGCACCGACATCCCATTT
CAACTGAGCAAGTATGTTGATAATCAACGTCTGTT
GAGCACTTTCACCGAGTATATCAAAAACATCATC
AATACTAGCATTCTGAACCTGCGTTACGAGAGCAA
TCATCTGATtGATCTGAGCCGTTATGCAAGCAAG
ATCAACATCGGTAGCAAGGTCAATTTTGACCCGAT
CGATAAGAACCAGATCCAGCTGTTTAATCTGGAA
TCGAGCAAAATTGAGGTTATCCTGAAAAACGCCAT
TGTCTACAACTCCATGTACGAGAATTTCTCCACC
AGCTTCTGGATTCGCATCCCGAAATACTTCAACAG
CATTAGCCTGAACAACGAGTATACTATCATCAAC
TGTATGGAGAACAACAGCGGTTGGAAGGTGTCTCT
GAACTATGGTGAGATCATTTGGACCTTGCAGGAC
ACCCAAGAGATCAAGCAGCGCGTCGTGTTCAAGTA
CTCTCAAATGATCAACATTTCCGATTACATTAAT
CGTTGGATCTTCGTGACCATTACGAATAACCGTCT
GAATAACAGCAAGATTTACATCAATGGTCGCTTG
ATCGATCAGAAACCGATTAGCAACCTGGGTAATAT
CCACGCAAGCAACAACATTATGTTCAAATTGGAC
GGTTGCCGCGATACCCATCGTTATATCTGGATCAA
GTATTTCAACCTGTTTGATAAAGAACTGAATGAG
AAGGAGATCAAAGATTTGTATGACAACCAATCTAA
CAGCGGCATTTTGAAGGACTTCTGGGGCGATTAT
CTGCAATACGATAAGCCGTACTATATGCTGAACCT
GTATGATCCGAACAAATATGTGGATGTCAATAAT
GTGGGTATTCGTGGTTACATGTATTTGAAGGGTCC
GCGTGGCAGCGTTATGACGACCAACATTTACCTG
AACTCTAGCCTGTACCGTGGTACGAAATTCATCAT
TAAGAAATATGCCAGCGGCAACAAAGATAACATT
GTGCGTAATAACGATCGTGTCTACATCAACGTGGT
CGTGAAGCGTAAAGAGTACCGTCTGGCGACCAAC
GCTTCGCAGGCGGGTGTTGAGAAAATTCTGAGCGC
GTTGGAGATCCCTCGTGTCCGTCGTCTGAGCCAA
```

-continued
GTCGTGGTTATGAAGAGCAAGAACGACCAGGGTAT

CACTAACAAGTGCAAGATGAACCTGCAAGACCGT

CGTGGTAACGACATCGGCTTTATTGGTTTCCACCA

GTTCAACAATATTGCTAAACTGGTAGCGAGCAAT

TGGTACAATCGTCAGATTGAGCGCCGTAGCCGTCG

TTTGGGCTGTAGCTGGGAGTTTATCCCGGTCGAT

GATGGTTGGGGCGAACGTCCGCTG

SEQ ID NO: 10. Engineered BoNT/A1 "Cat-D" amino acid sequence.
MPFVNKQFNYKDPVNGVDIAYIKIPNAGQMQPVKA

FKIHNKIWVIPERDTFTNPEEGDLNPPPEAKQVP

VSYYDSTYLSTDNEKDNYLKGVTKLFERIYSTDLG

RMLLTSIVRGIPFWGGSTIDTELKVIDTNCINVI

QPDGSYRSEELNLVIIGPSADIIQFECKSFGHEVL

NLTRNGYGSTQYIRFSPDFTFGFEESLEVDTNPL

LGAGKFATDPAVTLAHELIHAGHRLYGIAINPNRV

FKVNTNAYYEMSGLEVSFEELRTFGGHDAKFIDS

LQENEFRLYYYNKFKDIASTLNKAKSIVGTTASLQ

YMKNVFKEKYLLSEDTSGKESVDKLKEDKLYKML

TEIYTEDNEVKFEKVLNRKTYLNEDKAVFKINIVP

KVNYTIYDGENLRNTNLAANENGQNTEINNMNFT

KLKNFTGLFEFYKLLCVRGIITSKTKSLDKGYNKA

LNDLCIKVNNWDLFESPSEDNFTNDLNKGEEITS

DTNIEAAEENISLDLIQQYYLTFNEDNEPENISIE

NLSSDIIGQLELMPNIERFPNGKKYELDKYTMFH

YLRAQEFEHGKSRIALTNSVNEALLNPSRVYTFES

SDYVKKVNKATEAAMFLGWVEQLVYDFTDETSEV

STTDKIADITIIPYIGPALNIGNMLYKDDFVGAL

IFSGAVILLEFIPEIAIPVLGTFALVSYIANKVL

TVQTIDNALSKRNEKWDEVYKYIVTNWLAKVNTQI

DLIRKKMKEALENQAEATKAIINYQYNQYTEEEK

NNINFNIDDLSSKLNESINKAMININKFLNQCSVS

YLMNSMIPYGVKRLEDFDASLKDALLKYIYDNRG

TLIGQVDRLKDKVNNTLSTDIPFQLSKYVDNQRLL

STFTEYIKNIINTSILNLRYESNHLIDLSRYASK

INTGSKVNFDPIDKNQIQLFNLESSKIEVILKNAI

VYNSMYENFSTSFWIRIPKYFNSISLNNEYTIIN

CMENNSGWKVSLNYGEIIWTLQDTQEIKQRVVFKY

SQMINISDYINRWIFVTITNNRLNNSKIYINGRL

IDQKPISNLGNIHASNNIMFKLDGCRDTHRYIWIK

YFNLFDKELNEKEIKDLYDNQSNSGILKDFWGDY

-continued
LQYDKPYYMLNLYDPNKYVDVNNVGIRGYMYLKGP

RGSVMTTNIYLNSSLYRGTKFIIKKYASGNKDNI

VRNNDRVYINVVVKRKEYRLATNASQAGVEKILSA

LEIPRVRRLSQVVVMKSKNDQGITNKCKMNLQDR

RGNDIGFIGFHQFNNIAKLVASNWYNRQIERRSRR

LGCSWEETPVDDGWGERPL

EXAMPLES

The following Examples serve to illustrate particular embodiments of the invention, and do not limit the scope of the invention defined in the claims in any way.

Example 1

Three different examples of an engineered BoNT/A1 molecule according to the present invention were produced.
The amino acids chosen for modification (mutation sites) were selected using a number of different criteria.
The criteria for residue replacement were as follows:
1. Type of residue;
2. Degree of surface exposure;
3. Location with regard to secondary/tertiary structure;
4. Location with regard to the known functional domains of BoNT;
5. Degree of sequence conservation across the BoNT/A or BoNT/E subtypes;
6. Probability of introducing an additional ubiquitination site.

In this example, asparagine (Asn, N) and glutamine (Gln, Q), were selected for mutation because they are polar, are similar in size to Lys, only form weaker dipole interactions with other residues, and 14% of the molecule is composed of these two residues.

Asn and Gln residues visible at the surface of the molecule were identified from the crystal structure of BoNT/A1 (PDB ID: 3BTA). This ensures that all replaced residues will be able to display their charge externally. From this list, it was possible to rule out those less suitable for replacement by applying points 3-5 of the selection criteria above (a reiterative process).

Non-conserved residues within BoNT/A1 were identified from alignments with other subtypes of BoNT/A and of the functionally similar BoNT/E serotype. Those that appeared as a basic residue in the other sequences were selected as top candidates for replacement.

After successive iterative rounds through the selection criteria mentioned in the sections above, a final list of candidate residues was identified. These were screened for the potential generation of additional ubiquitination consensus sequences (using the CKSAAP_UbSite server). The few that were identified were removed by changing the replacement lysine to an arginine.

The final example cationic constructs synthesised for BoNT/A1 sequence are listed below, named Cat-A, Cat-B and Cat-C. Each construct had a molecular weight of 149,637 Daltons.
Cat-A: N930K, S955K, Q991K, N1026K, N1052K, Q1229K, N886K.

Cat-B: N930K, S955K, Q991K, N1026K, N1052K, Q1229K, N954K.
Cat-C: N930K, S955K, Q991K, N1026K, N1052K, Q1229K, N1025K.

Example 2

The BoNT/B, F and E amino acid sequences were assessed for potential residues that could be substituted with Lys or Arg. This initial assessment identified residues that could be substituted to yield a BoNT/B, E or F protein with an increased pI.

The primary sequence of BoNT/B (Ac: P10844), BoNT/E (Ac: Q00496), and BoNT/F (Ac: P30996) was analysed, and the amino acid composition summarised in the table below:

TABLE 3

| Serotype | Theoretical pI | Net charge at pH 7.4 | No. Asn & Gln | No. Asp & Glu |
| --- | --- | --- | --- | --- |
| BoNT/B | 5.3 | −23 | 179 | 156 |
| BoNT/E | 6.2 | −7 | 160 | 132 |
| BoNT/F | 5.4 | −22 | 169 | 161 |

From the table, a similarly large number of polar Asn/Gln residues were present in the amino acid sequence as observed for BoNT/A1. There were also a relatively large number of acidic (Asp/Glu) residues which could potentially be changed to either their corresponding neutral residues (Asn/Gln) or to basic residues (Lys or Arg).

Example 3

Identification of Preferred Clostridial Toxin Amino Acids for Modification

Full-length structural data was available for BoNT/A, BoNT/B, and BoNT/E;

however, for the remaining four serotypes, a theoretical model was generated based on sequence and associated structural homology using the LOOPP computer program.

Each structure was analysed by AreaIMol (CCP4 suite), and exposed residues were identified as having a sum value greater than 40. Residues with polar-side chains were selected from this list, and from this preference was placed on residues that were either acidic (Asp & Glu) or had an H-bond acceptor side chain (Asn & Gln). The final computational step involved selecting residues in between α-helices and β-strands based on analytical data from the Stride server. The structure of each molecule was visually inspected to identify residues located within interface regions—these were avoided.

For BoNT/A1, the list of preferred residues was supplemented with functionally non-conserved residues in at least 90% of all aligned sequences [large non-polar side chains (Met, Pro, Phe, Trp) were considered to be equivalent, small non-polar side chains (Gly, Ala, Val, Leu, Ile) were considered to be equivalent, acidic side chains (Asp, Glu) were considered to be equivalent, and basic side chains (Arg, Lys) were considered to be equivalent]. More specifically, those non-conserved residues that appeared as basic residues in at least 10% of the sequences and non-conserved Asn, Gln, Asp or Glu in the reference sequence, were selected as candidates.

For the remaining serotypes, multiple sequence alignments between subtypes was performed to identify functionally non-conserved residues that appeared as basic residues in at least 10% of the sequences.

Preferred clostridial toxin amino acids for modification:
BoNT/A:
ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086.
BoNT/B:
ASN 873, ASN 874, GLU 892, ASP 895, ASN 906, ASP 940, ASN 948, GLU 949, ASN 958, ASN 959, ASN 979, ASN 990, GLU 993, ASP 994, GLU 997, ASN 1012, ASN 1019, ASP 1030, ASP 1047, ASP 1049, GLU 1065, GLU 1072, GLN 1176, GLU 1189, GLU 1252, ASN 1273.
BoNT/$C_1$:
ASN 881, ASP 898, GLU 916, GLU 927, ASN 952, ASN 964, ASN 965, ASN 984, GLU 985, ASP 986, ASP 996, ASN 1000, GLU 1036, ASN 1041, ASP 1062, ASP 1064, GLU 1079, ASP 1081.
BoNT/D:
ASN 877, ASP 893, ASN 894, ASN 898, ASN 920, ASN 945, ASN 948, GLU 957, GLN 958, ASN 959, ASN 968, ASN 979, GLU 1030, ASP 1031, ASP 1033, GLU 1047, GLU 1051, ASN 1052, GLU 1066, GLN 1122.
BoNT/E:
ASN 859, ASP 860, ASN 892, ASP 893, ASP 904, ASP 909, ASN 928, ASN 932, ASN 934, ASN 935, GLU 936, ASP 945, ASN 946, ASN 947, ASN 966, ASN 976, ASN 979, ASN 981, ASP 985, GLN 1014, ASN 1019, ASN 1022, ASP 1027, ASN 1035, and ASN 1140.
BoNT/F:
ASN 879, ASP 896, ASN 922, ASN 923, ASN 928, ASN 947, ASN 950, ASN 952, ASN 953, GLU 954, ASN 963, ASN 964, ASN 965, ASN 987, GLN 997, ASN 1037, ASP 1040, ASP 1045, ASN 1055, ASP 1056.
BoNT/G:
ASP 900, ASN 909, ASN 910, GLU 912, ASN 913, ASN 945, ASN 947, GLU 956, ASN 965, ASP 966, ASN 986, ASN 1001, ASN 1038, ASP 1040, ASN 1046, ASP 1057, GLU 1073, ASN 1075, ASN 1090.
TeNT:
ASN 893, ASP 894, ASP 911, ASN 919, ASN 927, ASN 928, GLU 929, GLN 968, ASN 972, GLU 973, GLU 1010, ASP 1018, ASN 1079, ASN 1080, ASN 1081, ASN 1097.

Sequences Used
Accession Numbers:
BoNT/A: P10845
BoNT/B: P10844
BoNT/$C_1$: P18640
BoNT/D: P19321
BoNT/E: Q00496
BoNT/F: YP_001390123
BoNT/G: Q60393
TeNT: P04958

Structural Data Source

Crystal structures of BoNT/A (3BTA.pdb), BoNT/B (1EPW), and BoNT/E (3FFZ.pdb) obtained from RCSB.

Homology modelling of BoNT/$C_1$, BoNT/D, BoNT/F, BoNT/G, and TeNT performed using LOOPP and the following sequences, respectively: P18640, P19321, YP_001390123, Q60393, and P04958.

Structural Analysis
Exposed residues determined using AreaIMol from the CCP4 suite.
Secondary structure assignments determined using Stride.
Interface residues determined by visual inspection with RasMol.
Sequence Analysis
Full-length BoNT sequences obtained from NCBI.
Alignments performed with ClustalX.

Example 4

Cloning, Expression and Purification

DNA constructs encoding the engineered BoNT/A molecules described in Example 1 were synthesised, cloned into the pJ401 expression vector and then transformed into BL21 (DE3) *E. coli*. This allowed for soluble over-expression of the recombinant Cat-A, Cat-B and Cat-C proteins in BL21 (DE3) *E. coli*.

The recombinant engineered BoNTs were purified using classical chromatography techniques from the *E. coli* lysates. An initial purification step using a cation-exchange resin was employed, followed by an intermediate purification step using a hydrophobic interaction resin. The recombinant engineered BoNT single-chain was then cleaved by proteolysis, resulting in the activated di-chain engineered BoNT. A final purification step was then employed to remove remaining contaminants.

Example 5

Characterization of Purified Engineered BoNTs

The engineered BoNTs described in Example 1 above were characterised experimentally as follows.

Measurement of the pI showed that the engineered BoNTs had an isoelectric point greater than that of unmodified (native) BoNT/A1—see FIG. 1 and Table below.

TABLE 4

| BoNT/A1 molecule | pI (calculated) | pI (observed) |
| --- | --- | --- |
| Engineered, "Cat-A" [Cat5v2(K1064H/N886K)] | 6.9 | ~8.0 |
| Engineered, "Cat-B" [Cat5v2(K1064H/N954K)] | 6.9 | ~8.0 |
| Engineered, "Cat-C" [Cat5v2(K1064H/N1025K)] | 6.9 | 7.8-8.0 |
| Native BoNT/A1 [rBoNT/A1] | 6.05 | ~7.4 |

The ability of the engineered BoNTs to enter neurons and cleave SNAP-25 (the target of BoNT/A1) was assessed using rat embryonic spinal cord neurons (eSCN). FIG. 2 shows that the engineered BoNTs retained the same ability to enter the neuron and cleave SNAP-25 as native BoNT/A1.

Potency of the engineered BoNTs was further assessed using the mouse phrenic nerve hemi-diaphragm assay (mP-NHD). FIG. 3 shows that the engineered BoNTs retained the same ability to inhibit the contractile abilities of the mouse hemi-diaphragm as native BoNT/A1.

The in vivo mouse Digital Abduction Score (DAS) assay was used to assess potency as well as safety relative to native BoNT/A1. Both molecules displayed a higher safety ratio relative to native BoNT/A1 and were slightly more potent. These data are presented below (Table 4).

TABLE 4

| Molecule | DAS $ED_{50}$ (pg/mouse) | Dose DAS 4 (pg/mouse) | Dose for −10% ΔBW (pg/mouse) | Safety Ratio |
| --- | --- | --- | --- | --- |
| Native BoNT/A1 (n = 5) | 2 | 10-20 | 9.9-14.5 | 7 |
| Engineered, "Cat-A" | 1.16 | 10-20 | 27.4 | 24 |
| Engineered, "Cat-B" | 1.79 | 25 | 47.6 | 27 |

DAS $ED_{50}$: Calculated dose inducing a DAS 2
Dose DAS 4: Experimental dose inducing a DAS 4
BW: Body weight
Dose for −10% ΔBW: Calculated dose inducing a decrease of 10% on BW in comparison to BW at D0
Safety Ratio: Dose for −10% ΔBW/DAS $ED_{50}$ The Safety Ratio is a measure of a negative effect of BoNT treatment (weight loss) with respect to potency (half maximal digital abduction score (DAS)). It is calculated as the ratio between −10% Body Weight (BW) and the DAS $ED_{50}$, where −10% BW refers to the amount of BoNT (pg/animal) required for a 10% decrease in body weight, and $ED_{50}$ refers to the amount of BoNT (pg/animal) that will produce a DAS of 2.

The DAS assay is performed by injection of 20 μl of engineered clostridial toxin, formulated in Gelatin Phosphate Buffer, into the mouse gastrocnemius/soleus complex, followed by assessment of Digit Abduction as previously reported by Aoki (Aoki K R, Toxicon 39: 1815-1820; 2001).

Example 6

A further engineered clostridial toxin according to the present invention was designed using the criteria as set out in Example 1 above.

This cationic construct was also derived from BoNT/A1 and had a calculated pI of 7.4, and a molecular weight of 149,859. The construct was named Cat-D. While constructs Cat-A, Cat-B and Cat-C comprised residues mutated to lysine, Cat-D comprised residues mutated to arginine.

Cat-D: N1188R, D1213R, G1215R, N1216R, N1242R, N1243R, S1274R, T1277R.

Example 7

Treatment of a Patient Suffering from Cervical Dystonia

A 50 year old female suffering from spasmodic torticollis presents in the clinic, having previously been treated with a therapeutically effective amount of a standard BoNT/A preparation into the neck muscle; however, the patient experienced dysphagia due to spread of the toxin into the oropharynx. The patient is treated with an injection in the neck muscles of approximately 1.5 ng (or more) of an engineered BoNT/A of the present invention. The patient's torticollis is significantly improved after 3-7 days, without the development of dysphagia, and the patient is able to hold her head and shoulder in a normal position for at least five months. Due to the engineered BoNT/A molecule's enhanced tissue retention and reduced spread, the physician is able to inject more product without fear of side effects; the enhanced dose leads to an extended duration of action.

Example 8

Treatment of a Patient Suffering from Blepharospasm

A 47 year old male presents in the clinic with blepharospasm. The patient is treated by injection of between 5 pg and 25 pg of an engineered BoNT/A of the present invention into the lateral pre-tarsal orbicularis oculi muscle of the upper lid and the later pre-tarsal orbicularis oculi of the lower lid. Alleviation of the patient's symptoms occur in about a week and last at least five months, without eye ptosis. The increased safety of the polypeptide of the present invention allows the physician to increase the dose and therefore extend the duration of the clinical effect.

Example 9

A 27 year old male suffering from cerebral palsy presents at the clinic with debilitating equinus foot and has difficulty walking. The patient had previously been treated with a therapeutically effective amount of BoNT/A, where alleviation improvement in his gait was accompanied by muscle weakness and pain in his extremities. The patient is treated by injection of about 20 pg/kg of an engineered BoNT/A of the present invention into each of two sites in the medial and lateral heads of the gastrocnemius muscle of the affected lower limb(s). Within a week, the patient's gait improves without previously seen side effects and the symptomatic relief lasts for at least four months. The ability to dose higher amounts of drug product leads to treatments which result in an extended duration of action.

The invention claimed is:

1. An engineered clostridial toxin comprising at least one amino acid modification, wherein said at least one amino acid modification increases the isoelectric point (pI) of the engineered clostridial toxin to a value that is at least 0.2 pI units higher than the pI of an otherwise identical clostridial toxin lacking said at least one amino acid modification; and wherein said at least one amino acid modification is located in the clostridial toxin receptor binding domain ($H_C$ domain).

2. The engineered clostridial toxin of claim 1, wherein said at least one amino acid modification increases the isoelectric point (pI) of the engineered clostridial toxin to a value that is at least 0.5 pI units higher than the pI of an otherwise identical clostridial toxin lacking said at least one amino acid modification.

3. The engineered clostridial toxin of claim 1, wherein said at least one amino acid modification increases the isoelectric point (pI) of the engineered clostridial toxin to a value that is at least one pI unit higher than the pI of an otherwise identical clostridial toxin lacking said at least one amino acid modification.

4. The engineered clostridial toxin of claim 1, wherein said at least one amino acid modification increases the isoelectric point (pI) of the engineered clostridial toxin to a value that is at least two pI units higher than the pI of an otherwise identical clostridial toxin lacking said at least one amino acid modification.

5. The engineered clostridial toxin of claim 1, wherein said at least one amino acid modification increases the isoelectric point (pI) of the engineered clostridial toxin to a value that is between 2 and 5 pI units higher than the pI of an otherwise identical clostridial toxin lacking said at least one amino acid modification.

6. The engineered clostridial toxin according to claim 1, wherein the engineered clostridial toxin has a pI of at least 6.

7. The engineered clostridial toxin according to claim 1, wherein the engineered clostridial toxin has a pI of between 6 and 10.

8. The engineered clostridial toxin according to claim 7, wherein the engineered clostridial toxin has a pI of between 7 and 9.

9. The engineered clostridial toxin according to claim 1, wherein the at least one amino acid modification is selected from the group consisting of: an amino acid substitution, an amino acid insertion, and an amino acid deletion.

10. The engineered clostridial toxin according to claim 9, wherein the at least one amino acid substitution is selected from the group consisting of: substitution of an acidic amino acid residue with a basic amino acid residue, substitution of an acidic amino acid residue with an uncharged amino acid residue, and substitution of an uncharged amino acid residue with a basic amino acid residue.

11. The engineered clostridial toxin according to claim 1, wherein the engineered clostridial toxin comprises between 1 and 80 amino acid modifications.

12. The engineered clostridial toxin according to claim 11, wherein the engineered clostridial toxin comprises between 4 and 40 amino acid modifications.

13. The engineered clostridial toxin according to claim 1, wherein the at least one amino acid modification is located in the clostridial toxin $H_{CN}$ domain.

14. The engineered clostridial toxin according to claim 1, wherein the at least one amino acid modification is a modification of a surface exposed amino acid residue.

15. The engineered clostridial toxin according to claim 1, wherein the at least one amino acid modification comprises modification of an amino acid residue selected from the group consisting of: an aspartic acid residue, a glutamic acid residue, a histidine residue, a serine residue, a threonine residue, an asparagine residue, a glutamine residue, a cysteine residue, and a tyrosine residue.

16. The engineered clostridial toxin according to claim 15, wherein the amino acid residue is substituted with a lysine residue or an arginine residue.

17. A nucleic acid comprising a nucleic acid sequence encoding an engineered clostridial toxin or the engineered clostridial toxin for use according to claim 1.

18. A method of producing a single-chain engineered clostridial toxin protein having a light chain and a heavy chain, the method comprising expressing a nucleic acid according to claim 17 in a suitable host cell, lysing the host cell to provide a host cell homogenate containing the single-chain engineered clostridial toxin protein, and isolating the single-chain engineered clostridial toxin protein.

19. A method of activating an engineered clostridial toxin, the method comprising:
   providing a single-chain engineered clostridial toxin protein obtained by the method of claim 18;
   contacting the protein with a protease that cleaves the protein at a recognition site located between the light chain and heavy chain; and
   converting the protein into a di-chain polypeptide wherein the light chain and heavy chain are joined together by a disulphide bond.

\* \* \* \* \*

UNITED STATES PATENT AND TRADEMARK OFFICE
CERTIFICATE OF CORRECTION

| | | |
|---|---|---|
| PATENT NO. | : 9,920,310 B2 | Page 1 of 1 |
| APPLICATION NO. | : 14/903458 | |
| DATED | : March 20, 2018 | |
| INVENTOR(S) | : Dina Brady Anderson et al. | |

It is certified that error appears in the above-identified patent and that said Letters Patent is hereby corrected as shown below:

In the Drawings

On Sheet 3, replace "Cat5v2 (K1064N/K1025K)" with --Cat5v2 (K1064H/N1025K)--.

In the Specification

At Column 34, Line 35, replace "K106411" with --K1064H--.

At Column 34, Line 44, replace "K106411" with --K1064H--.

At Column 34, Line 45, replace "K0125K" with --N1025K--.

At Column 34, Line 62, replace "K106411" with --K1064H--.

Signed and Sealed this
Twenty-third Day of October, 2018

Andrei Iancu
*Director of the United States Patent and Trademark Office*

SEQUENCE LISTING

<160> NUMBER OF SEQ ID NOS: 15

<210> SEQ ID NO 1
<211> LENGTH: 3888
<212> TYPE: DNA
<213> ORGANISM: Clostridium botulinum

<400> SEQUENCE: 1

```
atgccattcg tcaacaagca attcaactac aaagacccag tcaacggcgt cgacatcgca    60
tacatcaaga ttccgaacgc cggtcaaatg cagccggtta aggcttttaa gatccacaac   120
aagatttggg ttatcccgga gcgtgacacc ttcacgaacc cggaagaagg cgatctgaac   180
ccgccaccgg aagcgaagca agtccctgtc agctactacg attcgacgta cctgagcacg   240
gataacgaaa aagataacta cctgaaaggt gtgaccaagc tgttcgaacg tatctacagc   300
acggatctgg gtcgcatgct gctgactagc attgttcgcg gtatcccgtt ctggggtggt   360
agcacgattg acaccgaact gaaggttatc gacactaact gcattaacgt tattcaaccg   420
gatggtagct atcgtagcga agagctgaat ctggtcatca ttggcccgag cgcagacatt   480
atccaattcg agtgcaagag ctttggtcac gaggttctga atctgacccg caatggctat   540
ggtagcaccc agtacattcg tttttcgccg gattttacct tcggctttga agagagcctg   600
gaggttgata ccaatccgtt gctgggtgcg ggcaaattcg ctaccgatcc ggctgtcacg   660
ctggcccatg aactgatcca cgcaggccac cgcctgtacg gcattgccat caacccaaac   720
cgtgtgttca aggttaatac gaatgcatac tacgagatga cggcctgga agtcagcttc   780 gaagaactgc gcaccttcgg tggccatgac gctaaattca ttgacagctt gcaagagaat   840
gagttccgtc tgtactacta taacaaattc aaagacattg caagcacgtt gaacaaggcc   900
aaaagcatcg ttggtactac cgcgtcgttg cagtatatga agaatgtgtt taaagagaag   960
tacctgctgt ccgaggatac ctccggcaag tttagcgttg ataagctgaa gtttgacaaa  1020
ctgtacaaga tgctgaccga gatttacacc gaggacaact ttgtgaaatt cttcaaagtg  1080
ttgaatcgta aaacctatct gaattttgac aaagcggttt tcaagattaa catcgtgccg  1140
aaggtgaact acaccatcta tgacggtttt aacctgcgta caccaacct ggcggcgaac  1200 tttaacggtc agaatacgga aatcaacaac atgaatttca cgaagttgaa gaacttcacg  1260
ggtctgttcg agttctataa gctgctgtgc gtgcgcggta tcatcaccag caaaaccaaa  1320
agcctggaca aaggctacaa caaggcgctg aatgacctgt gcattaaggt aaacaattgg  1380
```

```
gatctgttct tttcgccatc cgaagataat tttaccaacg acctgaacaa gggtgaagaa      1440
atcaccagcg atacgaatat tgaagcagcg gaagagaata tcagcctgga tctgatccag      1500
cagtactatc tgacctttaa cttcgacaat gaaccggaga acattagcat tgagaatctg      1560
agcagcgaca ttatcggtca gctggaactg atgccgaata tcgaacgttt cccgaacggc      1620
aaaaagtacg agctggacaa gtacactatg ttccattacc tgcgtgcaca ggagtttgaa      1680
cacggtaaaa gccgtatcgc gctgaccaac agcgttaacg aggccctgct gaacccgagc      1740
cgtgtctata ccttcttcag cagcgactat gttaagaaag tgaacaaagc cactgaggcc      1800
gcgatgttcc tgggctgggt ggaacagctg gtatatgact tcacggacga gacgagcgaa      1860
gtgagcacta ccgacaaaat tgctgatatt accatcatta tcccgtatat tggtccggca      1920
ctgaacattg gcaacatgct gtacaaagac gattttgtgg gtgccctgat cttctccggt      1980
gccgtgattc tgctggagtt cattccggag attgcgatcc cggtgttggg taccttcgcg      2040
ctggtgtcct acatcgcgaa taaggttctg acggttcaga ccatcgataa cgcgctgtcg      2100
aaacgtaatg aaaaatggga cgaggtttac aaatacattg ttacgaattg gctggcgaaa      2160
gtcaataccc agatcgacct gatccgtaag aaaatgaaag aggcgctgga gaatcaggcg      2220
gaggccacca aagcaattat caactaccaa tacaaccagt acacggaaga agagaagaat      2280
aacattaact tcaatatcga tgatttgagc agcaagctga tgaatctat caacaaagcg      2340 atgatcaata tcaacaagtt tttgaatcag tgtagcgttt cgtacctgat gaatagcatg      2400
attccgtatg gcgtcaaacg tctggaggac ttcgacgcca gcctgaaaga tgcgttgctg      2460
aaatacattt acgacaatcg tggtacgctg attggccaag ttgaccgctt gaaagacaaa      2520
gttaacaata ccctgagcac cgacatccca tttcaactga gcaagtatgt tgataatcaa      2580
cgtctgttga gcactttcac cgagtatatc aaaaacatca tcaatactag cattctgaac      2640
ctgcgttacg agagcaatca tctgattgat ctgagccgtt atgcaagcaa gatcaacatc      2700
ggtagcaagg tcaattttga cccgatcgat aagaaccaga tccagctgtt taatctggaa      2760
tcgagcaaaa ttgaggttat cctgaaaaac gccattgtct acaactccat gtacgagaat      2820
ttctccacca gcttctggat tcgcatcccg aaatacttca acagcattag cctgaacaac      2880
gagtatacta tcatcaactg tatggagaac aacagcggtt ggaaggtgtc tctgaactat      2940
ggtgagatca tttggacctt gcaggacacc caagagatca agcagcgcgt cgtgttcaag      3000
tactctcaaa tgatcaacat ttccgattac attaatcgtt ggatcttcgt gaccattacg      3060
aataaccgtc tgaataacag caagatttac atcaatggtc gcttgatcga tcagaaaccg      3120
attagcaacc tgggtaatat ccacgcaagc aacaacatta tgttcaaatt ggacggttgc      3180
cgcgatAccc atcgttatat ctggatcaag tatttcaacc tgtttgataa agaactgaat      3240
gagaaggaga tcaaagattt gtatgacaac caatctaaca gcggcatttt gaaggacttc      3300
tggggcgatt atctgcaata cgataagccg tactatatgc tgaacctgta tgatccgaac      3360
aaatatgtgg atgtcaataa tgtgggtatt cgtggttaca tgtatttgaa gggtccgcgt      3420
ggcagcgtta tgacgaccaa catttacctg aactctagcc tgtaccgtgg tacgaaattc      3480
atcattaaga aatatgccag cggcaacaaa gataacattg tgcgtaataa cgatcgtgtc      3540
tacatcaacg tggtcgtgaa gaataaagag taccgtctgg cgaccaacgc ttcgcaggcg      3600
ggtgttgaga aaattctgag cgcgttggag atccctgatg tcggtaatct gagccaagtc      3660 gtggtttatga agagcaagaa cgaccagggt atcactaaca agtgcaagat gaacctgcaa      3720
gacaacaatg gtaacgacat cggctttatt ggtttccacc agttcaacaa tattgctaaa      3780
```

-continued

```
ctggtagcga gcaattggta caatcgtcag attgagcgca gcagccgtac tttgggctgt    3840
agctgggagt ttatcccggt cgatgatggt tggggcgaac gtccgctg                 3888
```

<210> SEQ ID NO 2
<211> LENGTH: 1296
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350
```

```
Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
```

```
            770             775             780
Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185
```

| | | | | | | | | | | |
|---|---|---|---|---|---|---|---|---|---|---|
| Lys | Glu | Tyr | Arg | Leu | Ala | Thr | Asn | Ala | Ser | Gln | Ala | Gly | Val | Glu |
| | 1190 | | | | 1195 | | | | 1200 | |

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 3
<211> LENGTH: 3888
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Engineered BoNT/A1

<400> SEQUENCE: 3

```
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca gtccctgtca gctactacg attcgacgta cctgagcacg     240
gataacgaaa agataacta cctgaaaggt gtgaccaagc tgttcgaacg tatctacagc     300
acggatctgg tcgcatgct gctgactagc attgttcgcg gtatcccgtt ctggggtggt     360
agcacgattg acaccgaact gaaggttatc gacactaact gcattaacgt tattcaaccg     420
gatggtagct atcgtagcga agagctgaat ctggtcatca ttggcccgag cgcagacatt     480
atccaattcg agtgcaagag ctttggtcac gaggttctga atctgacccg caatggctat     540
ggtagcaccc agtacattcg tttttcgccg gattttacct tcggctttga agagagcctg     600
gaggttgata ccaatccgtt gctgggtgcg ggcaaattcg ctaccgatcc ggctgtcacg     660
ctggcccatg aactgatcca cgcaggccac cgcctgtacg gcattgccat caacccaaac     720
cgtgtgttca aggttaatac gaatgcatac tacgagatga cggcctggga agtcagcttc     780
gaagaactgc gcaccttcgg tggccatgac gctaaattca ttgacagctt gcaagagaat     840
gagttccgtc tgtactacta taacaaattc aaagacattg caagcacgtt gaacaaggcc     900
aaaagcatcg ttggtactac cgcgtcgttg cagtatatga agaatgtgtt taagagaag     960
tacctgctgt ccgaggatac ctccggcaag tttagcgttg ataagctgaa gtttgacaaa    1020
ctgtacaaga tgctgaccga gatttacacc gaggacaact tgtgaaatt cttcaaagtg    1080
ttgaatcgta aacctatct gaattttgac aaagcggttt tcaagattaa catcgtgccg    1140
aaggtgaact acaccatcta tgacggtttt aacctgcgta acaccaacct ggcggcgaac    1200
tttaacggtc agaatacgga aatcaacaac atgaatttca cgaagttgaa gaacttcacg    1260
```

```
ggtctgttcg agttctataa gctgctgtgc gtgcgcggta tcatcaccag caaaaccaaa    1320
agcctggaca aaggctacaa caaggcgctg aatgacctgt gcattaaggt aaacaattgg    1380
gatctgttct tttcgccatc cgaagataat tttaccaacg acctgaacaa gggtgaagaa    1440
atcaccagcg atacgaatat tgaagcagcg aagagaata tcagcctgga tctgatccag     1500
cagtactatc tgacctttaa cttcgacaat gaaccggaga acattagcat tgagaatctg    1560
agcagcgaca ttatcggtca gctggaactg atgccgaata tcgaacgttt cccgaacggc    1620
aaaaagtacg agctggacaa gtacactatg ttccattacc tgcgtgcaca ggagtttgaa    1680
cacggtaaaa gccgtatcgc gctgaccaac agcgttaacg aggccctgct gaacccgagc    1740
cgtgtctata ccttcttcag cagcgactat gttaagaaag tgaacaaagc cactgaggcc    1800
gcgatgttcc tgggctgggt ggaacagctg gtatatgact tcacggacga gacgagcgaa    1860
gtgagcacta ccgacaaaat tgctgatatt accatcatta tcccgtatat tggtccggca    1920
ctgaacattg gcaacatgct gtacaaagac gattttgtgg gtgccctgat cttctccggt    1980
gccgtgattc tgctggagtt cattccggag attgcgatcc cggtgttggg taccttcgcg    2040
ctggtgtcct acatcgcgaa taaggttctg acggttcaga ccatcgataa cgcgctgtcg    2100
aaacgtaatg aaaaatggga cgaggtttac aaatacattg ttacgaattg gctggcgaaa    2160
gtcaataccc agatcgacct gatccgtaag aaaatgaaag aggcgctgga gaatcaggcg    2220
gaggccacca agcaattat caactaccaa tacaaccagt acacggaaga agagaagaat     2280
aacattaact tcaatatcga tgatttgagc agcaagctga atgaatctat caacaaagcg    2340
atgatcaata tcaacaagtt tttgaatcag tgtagcgttt cgtacctgat gaatagcatg    2400
attccgtatg gcgtcaaacg tctggaggac ttcgacgcca gcctgaaaga tgcgttgctg    2460
aaatacattt acgacaatcg tggtacgctg attggccaag ttgaccgctt gaaagacaaa    2520
gttaacaata ccctgagcac cgacatccca tttcaactga gcaagtatgt tgataatcaa    2580
cgtctgttga gcactttcac cgagtatatc aaaaacatca tcaatactag cattctgaac    2640
ctgcgttacg agagcaagca tctgattgat ctgagccgtt atgctagcaa gatcaacatc    2700
ggtagcaagg tcaattttga cccgatcgat aagaaccaga tccagctgtt taatctggaa    2760
tcgagcaaaa ttgaggttat cctgaaaaag gccattgtct acaactccat gtacgagaat    2820
ttctccacca gcttctggat tcgcatcccg aaatacttca acaagattag cctgaacaac    2880
gagtatacta tcatcaactg tatggagaac aacagcggtt ggaaggtgtc tctgaactat    2940
ggtgagatca tttggacctt gcaggacacc aaagagatca agcagcgcgt cgtgttcaag    3000
tactctcaaa tgatcaacat ttccgattac attaatcgtt ggatcttcgt gaccattacg    3060
aataaccgtc tgaataagag caagatttac atcaatggtc gcttgatcga tcagaaaccg    3120
attagcaacc tgggtaatat ccacgcaagc aacaagatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
```

-continued

```
ggtgttgaga aaattctgag cgcgttggag atccctgatg tcggtaatct gagccaagtc    3660
gtggttatga agagcaagaa cgacaagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg                 3888
```

<210> SEQ ID NO 4
<211> LENGTH: 1296
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Engineered BoNT/A1

<400> SEQUENCE: 4

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300
```

```
Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
        340                 345                 350

Asn Phe Val Lys Phe Lys Val Leu Asn Arg Lys Thr Tyr Leu Asn
    355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
        420                 425                 430

Gly Ile Ile Thr Ser Lys Thr Lys Ser Leu Asp Lys Gly Tyr Asn Lys
    435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
            485                 490                 495

Asp Leu Ile Gln Gln Tyr Tyr Leu Thr Phe Asn Phe Asp Asn Glu Pro
        500                 505                 510

Glu Asn Ile Ser Ile Glu Asn Leu Ser Ser Asp Ile Ile Gly Gln Leu
    515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
        580                 585                 590

Lys Val Asn Lys Ala Thr Glu Ala Met Phe Leu Gly Trp Val Glu
    595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
        660                 665                 670

Ile Pro Val Leu Gly Thr Phe Ala Leu Val Ser Tyr Ile Ala Asn Lys
    675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720
```

-continued

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Lys His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Lys Ala Ile Val Tyr Asn Ser Met Tyr Glu Asn Phe Ser Thr Ser
    930                 935                 940

Phe Trp Ile Arg Ile Pro Lys Tyr Phe Asn Lys Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Lys Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
        1010                1015                1020

Leu Asn Lys Ser Lys Ile Tyr Ile Asn Gly Arg Leu Ile Asp Gln
        1025                1030                1035

Lys Pro Ile Ser Asn Leu Gly Asn Ile His Ala Ser Asn Lys Ile
        1040                1045                1050

Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080

Ile Lys Asp Leu Tyr Asp Asn Gln Ser Asn Ser Gly Ile Leu Lys
        1085                1090                1095

Asp Phe Trp Gly Asp Tyr Leu Gln Tyr Asp Lys Pro Tyr Tyr Met
        1100                1105                1110

Leu Asn Leu Tyr Asp Pro Asn Lys Tyr Val Asp Val Asn Asn Val
        1115                1120                1125

Gly Ile Arg Gly Tyr Met Tyr Leu Lys Gly Pro Arg Gly Ser Val

-continued

```
        1130                1135                1140
Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Lys Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295
```

<210> SEQ ID NO 5
<211> LENGTH: 3888
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Engineered BoNT/A1

<400> SEQUENCE: 5

```
atgccattcg tcaacaagca attcaactac aaagacccag tcaacggcgt cgacatcgca    60
tacatcaaga ttccgaacgc cggtcaaatg cagccggtta aggcttttaa gatccacaac   120
aagatttggg ttatcccgga gcgtgacacc ttcacgaacc cggaagaagg cgatctgaac   180
ccgccaccgg aagcgaagca agtccctgtc agctactacg attcgacgta cctgagcacg   240
gataacgaaa aagataacta cctgaaaggt gtgaccaagc tgttcgaacg tatctacagc   300
acggatctgg gtcgcatgct gctgactagc attgttcgcg gtatcccgtt ctggggtggt   360
agcacgattg acaccgaact gaaggttatc gacactaact gcattaacgt tattcaaccg   420
gatggtagct atcgtagcga agagctgaat ctggtcatca ttggcccgag cgcagacatt   480
atccaattcg agtgcaagag ctttggtcac gaggttctga atctgacccg caatggctat   540
ggtagcaccc agtacattcg ttttcgccg gattttacct tcggctttga agagagcctg   600
gaggttgata ccaatccgtt gctgggtgcg ggcaaattcg ctaccgatcc ggctgtcacg   660
ctggcccatg aactgatcca cgcaggccac cgcctgtacg gcattgccat caacccaaac   720
cgtgtgttca aggttaatac gaatgcatac tacgagatga cggcctgga agtcagcttc   780
gaagaactgc gcaccttcgg tggccatgac gctaaattca ttgacagctt gcaagagaat   840
gagttccgtc tgtactacta taacaaattc aaagacattg caagcacgtt gaacaaggcc   900
aaaagcatcg ttggtactac cgcgtcgttg cagtatatga agaatgtgtt taaagagaag   960
```

```
tacctgctgt ccgaggatac ctccggcaag tttagcgttg ataagctgaa gtttgacaaa   1020
ctgtacaaga tgctgaccga gatttacacc gaggacaact tgtgaaatt cttcaaagtg   1080 ttgaatcgta aacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaacaa gggtgaagaa   1440
atcaccagcg atacgaatat tgaagcagcg aagagaata tcagcctgga tctgatccag   1500
cagtactatc tgaccttaa cttcgacaat gaaccggaga acattagcat gagaatctg   1560 agcagcgaca ttatcggtca gctggaactg atgccgaata tcgaacgttt cccgaacggc   1620
aaaaagtacg agctggacaa gtacactatg ttccattacc tgcgtgcaca ggagtttgaa   1680
cacggtaaaa gccgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg caacatgct gtacaaagac gatttgtgg gtgccctgat cttctccggt   1980
gccgtgattc tgctggagtt cattccggag attgcgatcc cggtgttggg taccttcgcg   2040
ctggtgtcct acatcgcgaa taaggttctg acggttcaga ccatcgataa cgcgctgtcg   2100
aaacgtaatg aaaatggga cgaggtttac aaatacattg ttacgaattg ctggcgaaa   2160 gtcaataccc agatcgacct gatccgtaag aaaatgaaag aggcgctgga gaatcaggcg   2220
gaggccacca agcaattat caactaccaa tacaaccagt acacggaaga agagaagaat   2280
aacattaact tcaatatcga tgatttgagc agcaagctga tgaatctat caacaaagcg   2340 atgatcaata tcaacaagtt tttgaatcag tgtagcgttt cgtacctgat gaatagcatg   2400
attccgtatg gcgtcaaacg tctggaggac ttcgacgcca gctgaaaga tgcgttgctg   2460 aaatacattt acgacaatcg tggtacgctg attggccaag ttgaccgctt gaaagacaaa   2520
gttaacaata ccctgagcac cgacatccca tttcaactga gcaagtatgt tgataatcaa   2580
cgtctgttga gcactttcac cgagtatatc aaaaacatca tcaatactag cattctgaac   2640
ctgcgttacg agagcaatca tctgattgat ctgagccgtt atgctagcaa gatcaacatc   2700
ggtagcaagg tcaattttga cccgatcgat aagaaccaga tccagctgtt taatctggaa   2760
tcgagcaaaa ttgaggttat cctgaaaaag gccattgtct acaactccat gtacgagaat   2820
ttctccacca gcttctggat tcgcatcccg aaatacttca agaagattag cctgaacaac   2880
gagtatacta tcatcaactg tatggagaac acagcggtt ggaaggtgtc tctgaactat   2940
ggtgagatca tttggacctt gcaggacacc aaagagatca gcagcgcgt cgtgttcaag   3000 tactctcaaa tgatcaacat ttccgattac attaatcgtt ggatcttcgt gaccattacg   3060
aataaccgtc tgaataagag caagatttac atcaatggtc gcttgatcga tcagaaaccg   3120
attagcaacc tgggtaatat ccacgcaagc aacaagatta tgttcaaatt ggacggttgc   3180
cgcgataccc atcgttatat ctggatcaag tatttcaacc tgtttgataa agaactgaat   3240
gagaaggaga tcaaagattt gtatgacaac caatctaaca gcggcatttt gaaggacttc   3300
```

| tggggcgatt atctgcaata cgataagccg tactatatgc tgaacctgta tgatccgaac | 3360 |
|---|---|
| aaatatgtgg atgtcaataa tgtgggtatt cgtggttaca tgtatttgaa gggtccgcgt | 3420 |
| ggcagcgtta tgacgaccaa catttacctg aactctagcc tgtaccgtgg tacgaaattc | 3480 |
| atcattaaga aatatgccag cggcaacaaa gataacattg tgcgtaataa cgatcgtgtc | 3540 |
| tacatcaacg tggtcgtgaa gaataaagag taccgtctgg cgaccaacgc ttcgcaggcg | 3600 |
| ggtgttgaga aaattctgag cgcgttggag atccctgatg tcggtaatct gagccaagtc | 3660 |
| gtggttatga agagcaagaa cgacaagggt atcactaaca agtgcaagat gaacctgcaa | 3720 |
| gacaacaatg gtaacgacat cggctttatt ggtttccacc agttcaacaa tattgctaaa | 3780 |
| ctggtagcga gcaattggta caatcgtcag attgagcgca gcagccgtac tttgggctgt | 3840 |
| agctgggagt ttatcccggt cgatgatggt tggggcgaac gtccgctg | 3888 |

```
<210> SEQ ID NO 6
<211> LENGTH: 1296
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Engineered BoNT/A1

<400> SEQUENCE: 6

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
```

```
                  245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
            595                 600                 605
Gln Leu Val Tyr Asp Phe Thr Asp Glu Thr Ser Glu Val Ser Thr Thr
            610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
```

```
Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
        850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
        915                 920                 925

Lys Lys Ala Ile Val Tyr Asn Ser Met Tyr Glu Asn Phe Ser Thr Ser
930                 935                 940

Phe Trp Ile Arg Ile Pro Lys Tyr Phe Lys Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
        1010                1015                1020

Leu Asn Lys Ser Lys Ile Tyr Ile Asn Gly Arg Leu Ile Asp Gln
        1025                1030                1035

Lys Pro Ile Ser Asn Leu Gly Asn Ile His Ala Ser Asn Lys Ile
        1040                1045                1050

Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080
```

```
Ile Lys  Asp Leu Tyr Asp Asn  Gln Ser Asn Ser Gly  Ile Leu Lys
    1085                 1090                 1095

Asp Phe  Trp Gly Asp Tyr Leu  Gln Tyr Asp Lys Pro  Tyr Tyr Met
    1100                 1105                 1110

Leu Asn  Leu Tyr Asp Pro Asn  Lys Tyr Val Asp Val  Asn Asn Val
    1115                 1120                 1125

Gly Ile  Arg Gly Tyr Met Tyr  Leu Lys Gly Pro Arg  Gly Ser Val
    1130                 1135                 1140

Met Thr  Thr Asn Ile Tyr Leu  Asn Ser Ser Leu Tyr  Arg Gly Thr
    1145                 1150                 1155

Lys Phe  Ile Ile Lys Lys Tyr  Ala Ser Gly Asn Lys  Asp Asn Ile
    1160                 1165                 1170

Val Arg  Asn Asn Asp Arg Val  Tyr Ile Asn Val Val  Val Lys Asn
    1175                 1180                 1185

Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215

Gln Val  Val Val Met Lys Ser  Lys Asn Asp Lys Gly  Ile Thr Asn
    1220                 1225                 1230

Lys Cys  Lys Met Asn Leu Gln  Asp Asn Asn Gly Asn  Asp Ile Gly
    1235                 1240                 1245

Phe Ile  Gly Phe His Gln Phe  Asn Asn Ile Ala Lys  Leu Val Ala
    1250                 1255                 1260

Ser Asn  Trp Tyr Asn Arg Gln  Ile Glu Arg Ser Ser  Arg Thr Leu
    1265                 1270                 1275

Gly Cys  Ser Trp Glu Phe Ile  Pro Val Asp Asp Gly  Trp Gly Glu
    1280                 1285                 1290

Arg Pro  Leu
    1295
```

<210> SEQ ID NO 7
<211> LENGTH: 3888
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Engineered BoNT/A1

<400> SEQUENCE: 7

```
atgccattcg tcaacaagca attcaactac aaagacccag tcaacggcgt cgacatcgca     60
tacatcaaga ttccgaacgc cggtcaaatg cagccggtta aggcttttaa gatccacaac    120
aagatttggg ttatcccgga gcgtgacacc ttcacgaacc cggaagaagg cgatctgaac    180
ccgccaccgg aagcgaagca agtccctgtc agctactacg attcgacgta cctgagcacg    240
gataacgaaa aagataacta cctgaaaggt gtgaccaagc tgttcgaacg tatctacagc    300
acggatctgg gtcgcatgct gctgactagc attgttcgcg gtatcccgtt ctggggtggt    360
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag ctttggtcac gaggttctga atctgacccg caatggctat    540
ggtagcaccc agtacattcg tttttcgccg gattttacct tcggctttga agagagcctg    600
gaggttgata ccaatccgtt gctgggtgcg ggcaaattcg ctaccgatcc ggctgtcacg    660
```

```
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta taacaaattc aaagacattg caagcacgtt gaacaaggcc    900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa   1020
ctgtacaaga tgctgaccga gatttacacc gaggacaact tgtgaaaatt cttcaaagtg   1080
ttgaatcgta aaacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaacaa gggtgaagaa   1440
atcaccagcg atacgaatat tgaagcagcg gaagagaata tcagcctgga tctgatccag   1500
cagtactatc tgacctttaa cttcgacaat gaaccggaga acattagcat tgagaatctg   1560
agcagcgaca ttatcggtca gctggaactg atgccgaata tcgaacgttt cccgaacggc   1620
aaaaagtacg agctggacaa gtacactatg ttccattacc tgcgtgcaca ggagtttgaa   1680
cacggtaaaa gccgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg gcaacatgct gtacaaagac gattttgtgg gtgccctgat cttctccggt   1980
gccgtgattc tgctggagtt cattccggag attgcgatcc cggtgttggg tacctttcgcg   2040 ctggtgtcct acatcgcgaa taaggttctg acggttcaga ccatcgataa cgcgctgtcg   2100
aaacgtaatg aaaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca agcaattat caactaccaa tacaaccagt acacgaaaga agagaagaat   2280
aacattaact tcaatatcga tgatttgagc agcaagctga tgaatctat caacaaagcg   2340 atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
aaatacattt acgacaatcg tggtacgctg attggccaag ttgaccgctt gaaagacaaa   2520
gttaacaata ccctgagcac cgacatccca tttcaactga gcaagtatgt tgataatcaa   2580
cgtctgttga gcactttcac cgagtatatc aaaaacatca tcaatactag cattctgaac   2640
ctgcgttacg agagcaatca tctgattgat ctgagccgtt atgctagcaa gatcaacatc   2700
ggtagcaagg tcaattttga cccgatcgat aagaaccaga tccagctgtt taatctggaa   2760
tcgagcaaaa ttgaggttat cctgaaaaag gccattgtct acaactccat gtacgagaat   2820
ttctccacca gcttctggat tcgcatcccg aaatacttca acaagattag cctgaacaac   2880
gagtatacta tcatcaactg tatggagaac aacagcggtt ggaaggtgtc tctgaactat   2940
ggtgagatca tttggacctt gcaggacacc aaagagatca agcagcgcgt cgtgttcaag   3000
```

-continued

```
tactctcaaa tgatcaacat ttccgattac attaatcgtt ggatcttcgt gaccattacg    3060
aataaccgtc tgaagaagag caagatttac atcaatggtc gcttgatcga tcagaaaccg    3120
attagcaacc tgggtaatat ccacgcaagc aacaagatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gaataaagag taccgtctgg cgaccaacgc ttcgcaggcg    3600
ggtgttgaga aaattctgag cgcgttggag atccctgatg tcggtaatct gagccaagtc    3660
gtggttatga gagcaagaa cgacaagggt atcactaaca agtgcaagat gaacctgcaa    3720
gacaacaatg gtaacgacat cggctttatt ggtttccacc agttcaacaa tattgctaaa    3780
ctggtagcga gcaattggta caatcgtcag attgagcgca gcagccgtac tttgggctgt    3840
agctgggagt ttatcccggt cgatgatggt tggggcgaac gtccgctg                 3888
```

<210> SEQ ID NO 8
<211> LENGTH: 1296
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Engineered BoNT/A1

<400> SEQUENCE: 8

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190
```

-continued

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Thr Phe Asn Phe Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr

```
                610                 615                 620
Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
                770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
                850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Lys Ala Ile Val Tyr Asn Ser Met Tyr Glu Asn Phe Ser Thr Ser
930                 935                 940

Phe Trp Ile Arg Ile Pro Lys Tyr Phe Asn Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
                980                 985                 990

Ile Lys Gln Arg Val Val Phe Lys  Tyr Ser Gln Met Ile  Asn Ile Ser
                995                 1000                1005

Asp Tyr  Ile Asn Arg Trp Ile  Phe Val Thr Ile Thr  Asn Asn Arg
                1010                1015                1020

Leu Lys  Lys Ser Lys Ile Tyr  Ile Asn Gly Arg Leu  Ile Asp Gln
                1025                1030                1035
```

```
Lys Pro Ile Ser Asn Leu Gly Asn Ile His Ala Ser Asn Lys Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Lys Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 9
<211> LENGTH: 3888
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Engineered BoNT/A1

<400> SEQUENCE: 9
atgccattcg tcaacaagca attcaactac aaagacccag tcaacggcgt cgacatcgca      60
tacatcaaga ttccgaacgc cggtcaaatg cagccggtta aggcttttaa gatccacaac     120
aagatttggg ttatcccgga gcgtgacacc ttcacgaacc cggaagaagg cgatctgaac     180
ccgccaccgg aagcgaagca agtccctgtc agctactacg attcgacgta cctgagcacg     240
gataacgaaa agataacta cctgaaaggt gtgaccaagt gttcgaacg tatctacagc      300 acggatctgg gtcgcatgct gctgactagc attgttcgcg gtatcccgtt ctgggggtggt     360
```

```
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag ctttggtcac gaggttctga atctgacccg caatggctat    540
ggtagcaccc agtacattcg tttttcgccg gattttacct tcggctttga agagagcctg    600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta taacaaattc aaagacattg caagcacgtt gaacaaggcc    900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa   1020
ctgtacaaga tgctgaccga gatttacacc gaggacaact ttgtgaaatt cttcaaagtg   1080
ttgaatcgta aaacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaacaa gggtgaagaa   1440
atcaccagcg atacgaatat tgaagcagcg gaagagaata tcagcctgga tctgatccag   1500
cagtactatc tgacctttaa cttcgacaat gaaccggaga acattagcat tgagaatctg   1560
agcagcgaca ttatcggtca gctggaactg atgccgaata tcgaacgttt cccgaacggc   1620
aaaaagtacg agctggacaa gtacactatg ttccattacc tgcgtgcaca ggagtttgaa   1680
cacggtaaaa gccgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg caacatgct gtacaaagac gattttgtgg gtgccctgat cttctccggt   1980
gccgtgattc tgctggagtt cattccggag attgcgatcc cggtgttggg taccttcgcg   2040
ctggtgtcct acatcgcgaa taaggttctg acgttcaga ccatcgataa cgcgctgtcg   2100
aaacgtaatg aaaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca agcaattat caactaccaa tacaaccagt acacggaaga agagaagaat   2280
aacattaact tcaatatcga tgatttgagc agcaagctga atgaatctat caacaaagcg   2340
atgatcaata tcaacaagtt tttgaatcag tgtagcgttt cgtacctgat gaatagcatg   2400
attccgtatg cgtcaaacg tctggaggac ttcgacgcca gcctgaaaga tgcgttgctg   2460
aaatacattt acgacaatcg tggtacgctg attggccaag ttgaccgctt gaaagacaaa   2520
gttaacaata ccctgagcac cgacatccca tttcaactga gcaagtatgt tgataatcaa   2580
cgtctgttga gcacttcac cgagtatatc aaaaacatca tcaatactag cattctgaac   2640
ctgcgttacg agagcaatca tctgattgat ctgagccgtt atgcaagcaa gatcaacatc   2700
```

-continued

```
ggtagcaagg tcaattttga cccgatcgat aagaaccaga tccagctgtt taatctggaa    2760
tcgagcaaaa ttgaggttat cctgaaaaac gccattgtct acaactccat gtacgagaat    2820
ttctccacca gcttctggat tcgcatcccg aaatacttca acagcattag cctgaacaac    2880
gagtatacta tcatcaactg tatggagaac aacagcggtt ggaaggtgtc tctgaactat    2940
ggtgagatca tttggacctt gcaggacacc caagagatca agcagcgcgt cgtgttcaag    3000
tactctcaaa tgatcaacat ttccgattac attaatcgtt ggatcttcgt gaccattacg    3060
aataaccgtc tgaataacag caagatttac atcaatggtc gcttgatcga tcagaaaccg    3120
attagcaacc tgggtaatat ccacgcaagc aacaacatta tgttcaaatt ggacggttgc    3180
cgcgataccc atcgttatat ctggatcaag tatttcaacc tgtttgataa agaactgaat    3240
gagaaggaga tcaaagattt gtatgacaac caatctaaca gcggcatttt gaaggacttc    3300
tggggcgatt atctgcaata cgataagccg tactatatgc tgaacctgta tgatccgaac    3360
aaatatgtgg atgtcaataa tgtgggtatt cgtggttaca tgtatttgaa gggtccgcgt    3420
ggcagcgtta tgacgaccaa catttacctg aactctagcc tgtaccgtgg tacgaaattc    3480
atcattaaga aatatgccag cggcaacaaa gataacattg tgcgtaataa cgatcgtgtc    3540
tacatcaacg tggtcgtgaa gcgtaaagag taccgtctgg cgaccaacgc ttcgcaggcg    3600
ggtgttgaga aaattctgag cgcgttggag atccctcgtg tccgtcgtct gagccaagtc    3660
gtggttatga gagcaagaa cgaccagggt atcactaaca agtgcaagat gaacctgcaa    3720
gaccgtcgtg gtaacgacat cggctttatt ggtttccacc agttcaacaa tattgctaaa    3780
ctggtagcga gcaattggta caatcgtcag attgagcgcc gtagccgtcg tttgggctgt    3840
agctgggagt ttatcccggt cgatgatggt tggggcgaac gtccgctg               3888
```

<210> SEQ ID NO 10
<211> LENGTH: 1296
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Engineered BoNT/A1

<400> SEQUENCE: 10

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140
```

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
            165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560
```

-continued

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Asp Tyr Val Lys
        580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
        850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu

```
                        980             985             990
Ile Lys Gln Arg Val Phe Lys Tyr Ser Gln Met Ile Asn Ile Ser
            995             1000            1005

Asp Tyr Ile Asn Arg Trp Ile Phe Val Thr Ile Thr Asn Asn Arg
    1010            1015            1020

Leu Asn Asn Ser Lys Ile Tyr Ile Asn Gly Arg Leu Ile Asp Gln
    1025            1030            1035

Lys Pro Ile Ser Asn Leu Gly Asn Ile His Ala Ser Asn Asn Ile
    1040            1045            1050

Met Phe Lys Leu Asp Gly Cys Arg Asp Thr His Arg Tyr Ile Trp
    1055            1060            1065

Ile Lys Tyr Phe Asn Leu Phe Asp Lys Glu Leu Asn Glu Lys Glu
    1070            1075            1080

Ile Lys Asp Leu Tyr Asp Asn Gln Ser Asn Ser Gly Ile Leu Lys
    1085            1090            1095

Asp Phe Trp Gly Asp Tyr Leu Gln Tyr Asp Lys Pro Tyr Tyr Met
    1100            1105            1110

Leu Asn Leu Tyr Asp Pro Asn Lys Tyr Val Asp Val Asn Asn Val
    1115            1120            1125

Gly Ile Arg Gly Tyr Met Tyr Leu Lys Gly Pro Arg Gly Ser Val
    1130            1135            1140

Met Thr Thr Asn Ile Tyr Leu Asn Ser Ser Leu Tyr Arg Gly Thr
    1145            1150            1155

Lys Phe Ile Ile Lys Lys Tyr Ala Ser Gly Asn Lys Asp Asn Ile
    1160            1165            1170

Val Arg Asn Asn Asp Arg Val Tyr Ile Asn Val Val Val Lys Arg
    1175            1180            1185

Lys Glu Tyr Arg Leu Ala Thr Asn Ala Ser Gln Ala Gly Val Glu
    1190            1195            1200

Lys Ile Leu Ser Ala Leu Glu Ile Pro Arg Val Arg Arg Leu Ser
    1205            1210            1215

Gln Val Val Val Met Lys Ser Lys Asn Asp Gln Gly Ile Thr Asn
    1220            1225            1230

Lys Cys Lys Met Asn Leu Gln Asp Arg Arg Gly Asn Asp Ile Gly
    1235            1240            1245

Phe Ile Gly Phe His Gln Phe Asn Asn Ile Ala Lys Leu Val Ala
    1250            1255            1260

Ser Asn Trp Tyr Asn Arg Gln Ile Glu Arg Arg Ser Arg Arg Leu
    1265            1270            1275

Gly Cys Ser Trp Glu Phe Ile Pro Val Asp Asp Gly Trp Gly Glu
    1280            1285            1290

Arg Pro Leu
    1295

<210> SEQ ID NO 11
<211> LENGTH: 5
<212> TYPE: PRT
<213> ORGANISM: Unknown
<220> FEATURE:
<223> OTHER INFORMATION: Description of Unknown:
      Enterokinase cleavage site

<400> SEQUENCE: 11

Asp Asp Asp Asp Lys
1               5
```

```
<210> SEQ ID NO 12
<211> LENGTH: 4
<212> TYPE: PRT
<213> ORGANISM: Unknown
<220> FEATURE:
<223> OTHER INFORMATION: Description of Unknown:
      Factor Xa cleavage site
<220> FEATURE:
<221> NAME/KEY: MOD_RES
<222> LOCATION: (2)..(2)
<223> OTHER INFORMATION: Glu or Asp

<400> SEQUENCE: 12

Ile Xaa Gly Arg
1

<210> SEQ ID NO 13
<211> LENGTH: 7
<212> TYPE: PRT
<213> ORGANISM: Tobacco etch virus

<400> SEQUENCE: 13

Glu Asn Leu Tyr Phe Gln Gly
1               5

<210> SEQ ID NO 14
<211> LENGTH: 6
<212> TYPE: PRT
<213> ORGANISM: Unknown
<220> FEATURE:
<223> OTHER INFORMATION: Description of Unknown:
      Thrombin cleavage site

<400> SEQUENCE: 14

Leu Val Pro Arg Gly Ser
1               5

<210> SEQ ID NO 15
<211> LENGTH: 8
<212> TYPE: PRT
<213> ORGANISM: Unknown
<220> FEATURE:
<223> OTHER INFORMATION: Description of Unknown:
      PreScission cleavage site

<400> SEQUENCE: 15

Leu Glu Val Leu Phe Gln Gly Pro
1               5
```